(12) United States Patent
Nowotnik et al.

(10) Patent No.: US 7,166,733 B2
(45) Date of Patent: *Jan. 23, 2007

(54) O,O'-AMIDOMALONATE AND N,O-AMIDOMALONATE PLATINUM COMPLEXES

(75) Inventors: David P. Nowotnik, Colleyville, TX (US); Donald R. Stewart, Fort Worth, TX (US); Paul Sood, Dallas, TX (US); Sergiy Victorovych Shevchuk, Carrollton, TX (US); Kenneth Bruce Thurmond, II, Plano, TX (US)

(73) Assignee: Access Pharmaceuticals, Inc., Dallas, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/779,186

(22) Filed: Feb. 13, 2004

(65) Prior Publication Data

US 2004/0175387 A1    Sep. 9, 2004

Related U.S. Application Data

(63) Continuation-in-part of application No. 09/755,220, filed on Jan. 4, 2001, now Pat. No. 6,692,734.

(60) Provisional application No. 60/174,435, filed on Jan. 4, 2000.

(51) Int. Cl.
*C07F 15/00* (2006.01)
*A61K 31/28* (2006.01)
*A61K 31/74* (2006.01)

(52) U.S. Cl. .................... 556/137; 514/492; 424/78.08

(58) Field of Classification Search ................ 556/137; 514/492; 424/78.08

See application file for complete search history.

(56) References Cited

U.S. PATENT DOCUMENTS

| 4,946,954 | A | 8/1990 | Talebian et al. |
| 5,965,118 | A | 10/1999 | Duncan et al. |
| 6,692,734 | B1 * | 2/2004 | Stewart et al. ........... 424/78.27 |

FOREIGN PATENT DOCUMENTS

| EP | 0 281 412 A | 9/1988 |
| EP | 0 284 197 A | 9/1988 |

OTHER PUBLICATIONS

Talebian et al., Anti-Cancer Drug Design, vol. 5, No. 4, Nov. 1990, pp. 371-380.*
Tibben et al., Anal. Bioanal. Chem., vol. 373, published Jun. 6, 2002, pp. 233-236.*
Gibson et al., Inorganic Chemistry, vol. 29, No. 25, pp. 5125-5129 (1990).*
Gibson, D. et al. "Multinuclear NMR Studies of the Reactions Between cis-Diaminequaplatinum(II) Complexes and Aminomalonate" *Inorg. Chem.* (1990) 29(25):5125-5129.
Patent Abstract of Japan, vol. 014, No. 232 (C-0719) May 17, 1990.

(Continued)

*Primary Examiner*—Porfirio Nazario-Gonzalez
(74) *Attorney, Agent, or Firm*—Foley & Lardner LLP

(57) ABSTRACT

The present invention relates to amidomalonate O,O'—Pt and N,O—Pt chelates and methods of preparing them in essentially pure form.

47 Claims, 11 Drawing Sheets

OTHER PUBLICATIONS

Patent Abstract, JP 02 056241 A (Tanabe Seiyaku Co. LTD.) Feb. 26, 1990.

Patent Abstract of Japan, vol. 014, No. 246 (c-0722) May 25, 1990.

Patent Abstract, JP 02 067217 A (Tanabe Seiyaku Co. LTD.) May 7, 1990.

Ohya, Y. et al. "Antitumor drug delivery by dextran derivatives immobilizing platinum complex (II) through coordinating bond" *ACS Symp. Ser.* (1998) pp. 266-278.

Gandolfi, O. et al. "Syntheses of cis-dichlorodiammineplatinum analogs having steroidal hormones bound to the metal atom via malonato bridges" *Inorg. Chim. Acta.* (1989) 161(1):113-123.

Talebian, A. et al. "Synthesis of Characterization of a Series of Water Soluble Amidomalonato-(1R,2R-Cyclohexanediamine)Platinum(II) Complexes" *J. Coord. Chem.* (1990) 22:165-173.

Talebian, A.H. et al. "Murine anti-tumor activity of new water soluble platinum(II) complexes with reduced toxicity" *Anticancer Drug Design* (1990) 5:371-380.

PCT International Search Report, PCT/US01/00284, 5 pgs. (2001).

* cited by examiner cisplatin carboplatin oxaliplatin

O,O-chelate of amidomalonate

N,O-chelate of amidomalonate

O,O'-AMIDOMALONATE AND N,O-AMIDOMALONATE PLATINUM COMPLEXES

RELATED APPLICATIONS

This application is a continuation-in-part of U.S. application Ser. No. 09/755,220, filed 4 Jan. 2001, now U.S. Pat. No. 6,692,734, issued Feb. 17, 2004, which claims priority from Provisional Application Ser. No. 60/174,435, filed 4 Jan. 2000, both of which are incorporated by reference, including any drawings, as if fully set forth herein.

BACKGROUND OF THE INVENTION

Cisplatin (cDDP or cis-diamminedichloroplatinum(II), FIG. 1) is the most widely used of the platinium chemotherapeutic compounds approved for use in humans and is currently indicated for the treatment of testicular, ovarian, and head and neck tumors and, in combination with other agents, for the treatment of squamous cell and small cell lung carcinomas. The anti-tumor activity of cisplatin is believed to result from the loss of the chlorine ligand(s) in vivo to form reactive mono- or di-aqua complexes, which, in turn, form intra- and inter-strand DNA cross-links in tumor cells, leading to cell death.

There are, however, significant limitations to the use of cisplatin due to its nephrotoxicity and ototoxicity. Many novel small molecule Pt complexes have been made and tested in hope of finding new compounds having improved therapeutic indices (the ratio of the maximum tolerated dose to the minimum effective dose). For example, at the Institute for Cancer Research in the U.K., it was demonstrated that replacing the chlorine atoms with other leaving groups could give compounds exhibiting lower nephrotoxicity. This led to the discovery of carboplatin (FIG. 1), a cisplatin analog in which the chloride ligands are replaced by a 1,1-cyclobutane-dicarboxylic acid chelate. The chelate is less labile than the chlorides of cisplatin so higher doses of carboplatin are required to achieve a tumorcidal effect similar to that of cisplatin. Carboplatin's higher therapeutic index and different toxicity profile, however, negates this potential disadvantage. The dose-limiting toxicity of carboplatin is myelosuppression.

Oxaliplatin (FIG. 1) is another Pt chelate approved for human use. Oxaliplatin was the result of research into the effect of replacing both the non-labile (ammine, ammonia) and the labile (chloride) ligands of cisplatin with other groups. In oxaliplatin, the ammonia ligands are replaced with a trans-1R,2R-diaminocyclohexane (1R,2R-DACH) chelate and the chloride ligands are replaced with an oxalic acid chelate. Oxaliplatin is indicated in the treatment of colorectal cancer. The dose-limiting toxicity of oxaliplatin is sensory neuropathy.

Many other small molecule Pt complexes have been made and tested but so far only slight improvements in efficacy and therapeutic index have been achieved. A number of attempts to improve the therapeutic index of the approved platinum complexes have involved either combination therapy, for example, the co-administration of cisplatin and paclitaxel, or formulation changes such as delivery in liposomes.

Another approach to improving the therapeutic index of Pt complexes would be to target the complexes to tumor cells. Conventional small molecule Pt complexes such as cisplatin, carboplatin, and oxaliplatin are not specifically targeted to tumor cells and, following intravenous administration, they diffuse into normal cells as readily as into tumor cells. One method of tumor targeting that has been extensively studied with regard to non-Pt chemotherapeutics involves the attachment of the chemotherapeutic compound to a polymer or other macromolecular structure such as a dendrimer, a serum protein or an antibody. It has been demonstrated that the concentration of polymers and nanoparticles in tumors exceeds their concentration in normal tissue following intravenous administration. The mechanism for this preferred tumor accumulation has been termed the "enhanced permeability and retention" (EPR) effect. Essentially, tumor endothelial cells layers tend to be more 'leaky' than normal endothelial cell layers so that large chemical entities such as polymers and nanoparticles more readily cross the endothelial cell layer of the tumor vasculature and enter the interstitial areas of the tumor ("enhanced permeability"). Furthermore, lymphatic drainage of extracellular fluid in tumors is much less efficient than that of normal cells, thus reducing the rate of efflux of polymers and nanoparticles from tumors compared to normal tissue ("enhanced retention").

Examples of constructs that provide passive targeting of chemo-therapeutic agents to tumors through the EPR effect include doxorubicin attached to a linear polyhydroxypropylmethacrylamide polymer (poly(HPMA)) through a tetrapeptide designed to be cleaved by lysosomal enzymes. This water-soluble conjugate, termed "PKI," has been the subject of numerous publications describing its chemistry, pre-clinical testing and clinical evaluation. Similarly, poly (HPMA) has been conjugated with paclitaxel and camptothecin for selective delivery of these chemotherapeutic molecules to tumors.

In addition to passive tumor targeting, it may also be possible to target Pt complexes to tumors using active mechanisms such as coupling of the Pt complex to a moiety that binds to a receptor which is up-regulated in tumor cells compared to normal cells. A wide variety of such up-regulated receptors are known (Heppeler, et al., 2000; Schlaeppi, et al., 1999; Sudimack, et al., 2000; Dubowchik, et al., 1999; Weiner, 1999; Buolamwini, 1999). Examples of receptor binding agents include monoclonal antibodies, peptides, somatostatin analogs, folic acid derivatives, lectins, vitamins, such as cobalamin and its derivatives, biotin and polyanionic polysaccharides. Studies of Pt conjugated with monoclonal antibodies (McIntosh, et al., 1997; Hata, et al., 1992), steroids (Gust, et al., 1995; DiZio, et al., 1992, Gibson, et al., 1990) and folic acid (Vitols, et al., 1987) have been reported but none have been evaluated in the clinic.

It is also possible to combine passive and active targeting. This is exemplified by PK2, a compound comprising poly (HPMA) to which doxorubicin is attached through an enzyme cleavable peptide and to which galactose, a carbohydrate with strong affinity for the asialoglycoprotein receptor, which is highly concentrated in the liver, is also conjugated.

What is needed is a means of preparing a pharmaceutically acceptable Pt-polymer complex, i.e., a complex of known and reproducible structure and purity that can be used to target tumors using active and passive targeting technologies. The present invention provides such a means and the Pt complexes prepared thereby.

SUMMARY OF THE INVENTION

Thus, in one aspect, the present invention relates to an amidomalonate N,O—Pt complex having the chemical structure:

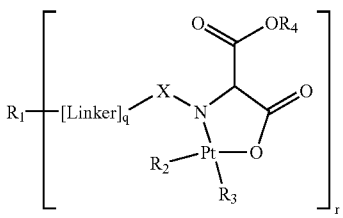

wherein:

X is C=O or $SO_2$;

$R_1$ is selected from the group consisting of hydrogen, an aliphatic group, a water-solubilizing group, a tumor-targeting group and a water-solubilizing group further comprising one or more tumor-targeting group(s);

q is 0 or 1;

r is 1–500;

[Linker] is selected from the group consisting of an alkyl group, an amino acid, a polyaminoacid, a polyethyleneglycol (PEG) and any combination thereof;

$R_2$ and $R_3$ are independently selected from the group consisting of $NH_3$, a primary amine, a secondary amine, a tertiary amine and a nitrogen-containing heterocyclic; or, $R_2$ and $R_3$ are independently primary, secondary or tertiary amino groups, both of which are covalently bonded to carbon atoms of an aliphatic, an alicyclic, an aromatic, an aralkyl or a heterocyclic group wherein, when the amino group nitrogen atoms form a chelate with the Pt atom, a 5–7 member ring results;

$R_4$ is selected from the group consisting of hydrogen, a cation and an ester-forming group, wherein, the complex is obtained essentially pure by a process comprising contacting a corresponding amidomalonate O,O'—Pt complex or a mixture of amidomalonate O,O'—Pt and N,O—Pt complexes with an aqueous solution having a pH of 6.0 to 10.0.

Another aspect of this invention is an amidomalonate O,O'—Pt complex having the chemical structure:

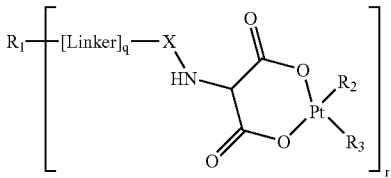

wherein:

X is C=O or $SO_2$;

$R_1$ is selected from the group consisting of hydrogen, an aliphatic group, a water-solubilizing group, a tumor-targeting group and a water-solubilizing group further comprising one or more tumor-targeting group(s);

q is 0 or 1;

r is 1–500;

[Linker] is selected from the group consisting of an alkyl group, an amino acid, a polyaminoacid, a polyethylene glycol (PEG) and any combination thereof;

$R_2$ and $R_3$ are independently selected from the group consisting of $NH_3$, a primary amine, a secondary amine, a tertiary amine and a nitrogen-containing heterocyclic; or, $R_2$ and $R_3$ are independently primary, secondary or tertiary amino groups, both of which are covalently bonded to carbon atoms of an aliphatic, an alicyclic, an aromatic, an alkaryl or a heterocyclic group wherein, when the amino nitrogen atoms form a chelate with the Pt atom, a 5–7 member ring results;

the complex is obtained essentially pure by a process comprising contacting a corresponding amidomalonate N,O—Pt complex or a mixture of amidomalonate N,O—Pt and O,O'—Pt complexes with an aqueous solution having a pH of 3.5 or less.

In an aspect of this invention, the pH used to prepare the essentially pure amidomalonate N,O—Pt complex is 7.0–8.0.

In an aspect of this invention, the pH used to prepare the essentially pure amidomalonate O,O'—Pt complex is 2.0–3.5.

In an aspect of this invention, the aqueous solution is at a temperature of 20° C. to 50° C.

In an aspect of this invention, the aqueous solution is at a temperature of 35° C. to 40° C.

In an aspect of this invention, the aqueous solution is maintained at the selected pH using a buffer.

In an aspect of this invention, the buffer is a phosphate buffer.

In an aspect of this invention, the pH is maintained in the selected range by pH stating.

In an aspect of this invention, the cation is selected from the group consisting of $Li^+$, $Na^+$, $K^+$, $Ca^{2+}$, $Mg^{2+}$ and quaternary ammonium.

In an aspect of this invention, the cation is $Na^+$.

In an aspect of this invention, $R_2$ and $R_3$ are $NH_3$.

In an aspect of this invention, $R_2$ and $R_3$, together, comprise 1,2-diaminocyclohexane,

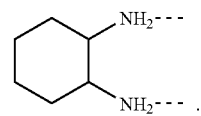

In an aspect of this invention, the 1,2-diaminocyclohexane is 1R, 2R-diaminocyclohexane.

In an aspect of this invention, [linker] comprises -Gly-$(W)_p$Gly-, wherein p is 0, 1, 2, 3, 4 or 5 and W is an amino acid or linear chain of amino acids, which may be the same or different.

In an aspect of this invention, p is 0.

In an aspect of this invention, p is 1 and W is Gly.

In an aspect of this invention, p is 2 and W is -Phe-Leu-.

In an aspect of this invention, p is 2 and W is Gly—Gly.

In an aspect of this invention, $R_1$ is a water-solubilizing group.

In an aspect of this invention, the water-solubilizing group is a copolymer of N-(2-(hydroxypropyl)methacrylamide and acroyl($CH_2$=CHC(O)—) or methacroyl ($CH_2$=C($CH_3$)C(O)—).

In an aspect of this invention, $R_1$ is a polyaminoacid.

In an aspect of this invention, the polyaminoacid is selected from the group consisting of polyglutamate, polyaspartate and polylysine.

In an aspect of this invention, $R_1$ is a polysaccharide.

In an aspect of this invention, $R_1$ is a water-solubilizing group further comprising a tumor-targeting group.

In an aspect of this invention, the tumor-targeting group is selected from the group consisting of folic acid, a folic acid derivative, a folic acid analog, vitamin $B_{12}$, a vitamin $B_{12}$ derivative, a vitamin $B_{12}$ analog, biotin, desthiobiotin and a biotin analog.

In an aspect of this invention, $R_1$ is a tumor-targeting group.

In an aspect of this invention, the tumor-targeting group is selected from the group consisting of folic acid, a folic acid derivative, a folic acid analog, vitamin $B_{12}$, a vitamin $B_{12}$ derivative, a vitamin $B_{12}$ analog, biotin, desthiobiotin and a biotin analog.

In an aspect of this invention, Pt is in the +2 oxidation state.

In an aspect of this invention, Pt is in the +4 oxidation state.

In an aspect of this invention, $R_1$ is a water-solubilizing random copolymer having the chemical structure:

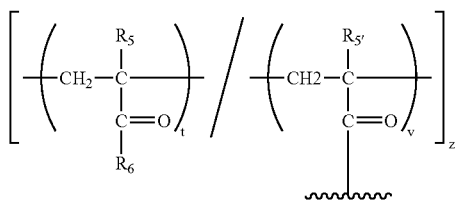

wherein:

t is 0.75–0.99;

v is 0.01–0.25;

t+v=1.00;

z represents the molecular weight of the polymer and is from 1 to 5000 kDaltons;

$R_5$ and $R_5$ are independently selected from the group consisting of hydrogen and $CH_3$; and, $R_6$ is a 2C–6C hydroxyalkyl group.

In an aspect of this invention, $R_6$ is 2-hydroxypropylamino ($CH_3CH(OH)CH_2NH-$).

In an aspect of this invention, obtaining an essentially pure complex further comprises ultrafiltration.

In an aspect of this invention, ultrafiltration comprises tangential flow filtration.

In an aspect of this invention, ultrafiltration comprises centrifugal ultrafiltration.

An aspect of this invention is a pharmaceutical composition comprising any of the above amidomalonate O,O'—Pt or N,O—Pt complexes and one or more pharmaceutically acceptable excipients.

An aspect of this invention is a method of treating a solid tumor comprising administering to a patient in need thereof a pharmaceutically effective amount of any of the above amidomalonate O,O'—Pt or N,O—Pt complexes.

In an aspect of this invention, the complex is administered parenterally.

An aspect of this invention is a method of preparing an essentially pure amidomalonate N,O—Pt chelate from an essentially pure amidomalonate O,O'—Pt chelate or a mixture of amidomalonate N,O—Pt and O,O'—Pt chelates, comprising contacting the amidomalonate O,O'—Pt chelate or the mixture of amidomalonate N,O—Pt and O,O'—Pt chelates with an aqueous solution having a pH of 6.0–10.0.

In an aspect of this invention, in the above method the pH is 7.0–8.0.

An aspect of this invention is a method of preparing an essentially pure amidomalonate O,O'—Pt chelate from an essentially pure amidomalonate N,O—Pt chelate or a mixture of amidomalonate N,O—Pt and O,O'—Pt chelates, comprising contacting the amidomalonate N,O—Pt chelate or the mixture of amidomalonate N,O—Pt and O,O'—Pt chelates with an aqueous solution having a pH of 3.5 and lower.

In an aspect of this invention, in the above method the pH is 2–3.5.

In an aspect of this invention, in the above methods, the aqueous solution is at a temperature of from 20° C. to 50° C.

In an aspect of this invention, in the above methods, the aqueous solution is at a temperature of from 35° C. to 40° C.

In an aspect of this invention, in the above methods, the aqueous solution is maintained in the selected pH range using a buffer.

In an aspect of this invention, in the above methods, the buffer is a phosphate buffer.

In an aspect of this invention, in the above methods, the aqueous solution is maintained in the selected pH range using pH stating.

DETAILED DESCRIPTION OF THE INVENTION

Brief Description of the Tables

Table 1 shows the effect of pH on the composition of a predominantly O,O-amidomalonate Pt complex at 38° C.

Table 2 shows the effect of pH on the composition of an 100% N,O—amidomalonate Pt complex at 38° C.

Table 3 shows the effect of two anions, chloride ($Cl^-$) and perchlorate ($ClO_4^-$) on the composition of an amidomalonate Pt complex at pH 5.0–5.5 starting with predominantly an O,O—Pt chelate and with a 100% N,O-amidomalonate.

Table 4 shows the percent Pt released versus pH over time for poly(HPMA)-GFLG-Ama-Pt($NH_3$)$_2$, 100% N,O-chelate.

Table 5 shows the $IC_{50}$ of various compounds of this invention compared to cisplatin and carboplatin.

Table 6 shows a comparison of the toleration level of mice to O,O'- and N,O-amidomalonate Pt complexes of this invention.

DEFINITIONS

Figure 1:
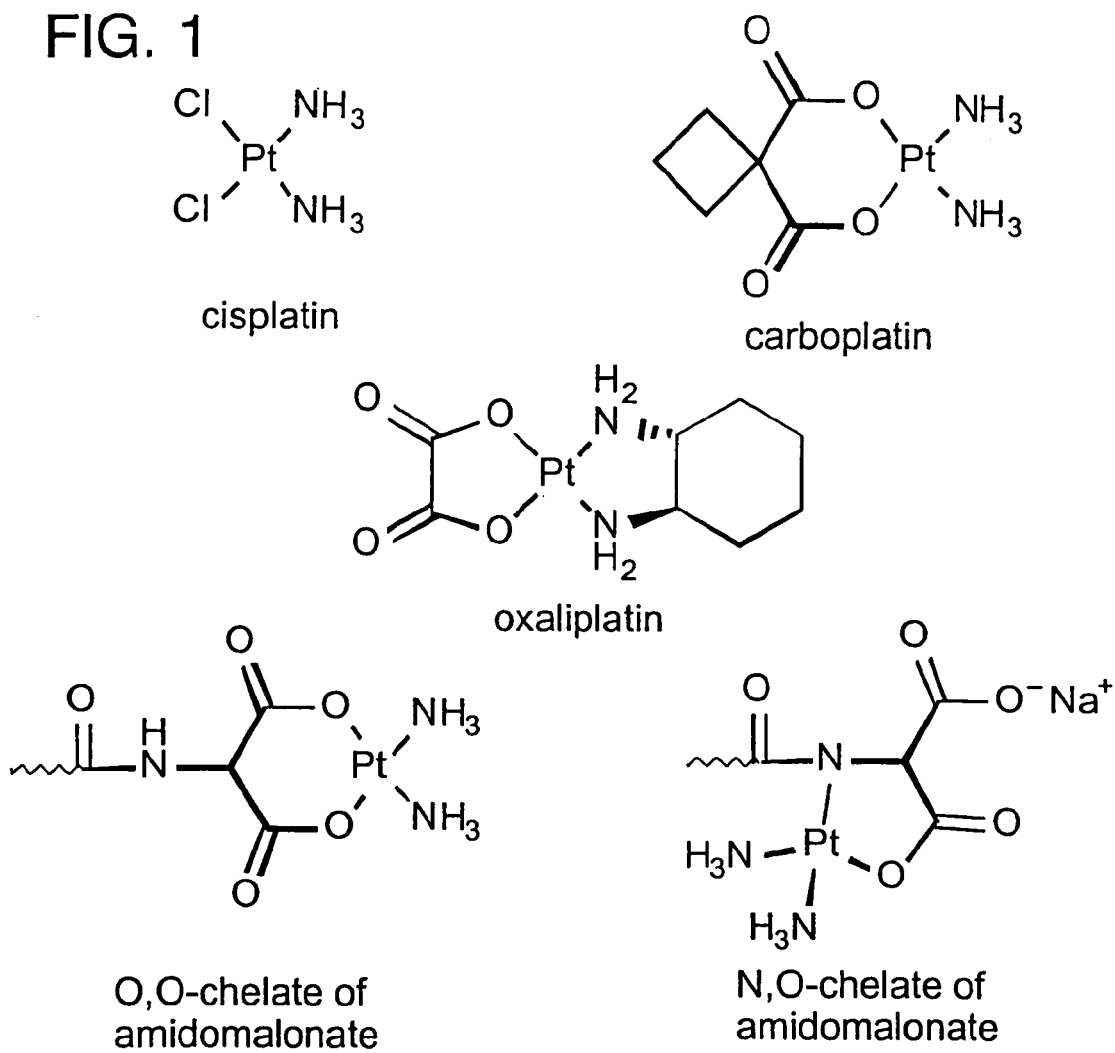
FIG. 1 shows the structures of cisplatin, carboplatin, oxaliplatin, and the basic structures of O,O'—Pt and N,O—Pt chelates of amidomalonate-cis-diammineplatinum(II).
Figure 2A:
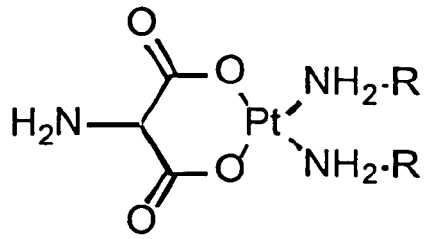
FIG. 2A shows the structure of an O,O'—Pt chelate of aminomalonate-cis-diamineplatinum(II).
Figure 2B:
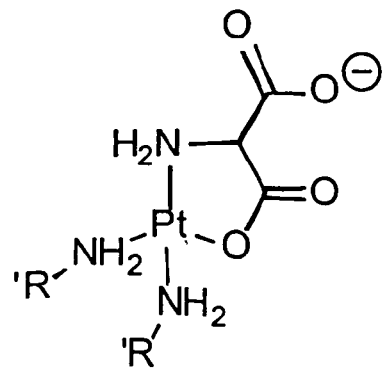
FIG. 2B shows the structure of an N,O—Pt chelate of aminomalonate-cis-diamineplatinum(II).

The phrase "essentially pure" refers to an amidomalonate Pt chelate (Ama=Pt) in which greater than 90%, preferably greater than 95% and most preferably greater than 99% of the Pt is chelated as one isomer, that is, either the O,O'—Pt or the N,O—Pt amidomalonate chelate.

A "therapeutically effective amount" is an amount the administration of which results in cessation of growth, decrease in the rate of growth, regression in size or a complete disappearance of a tumor or tumors in a patient. For the purposes of this invention, it is expected that a therapeutically effective amount of a compound herein will be in the range of about 1 mg Pt/kg to about 1 gm Pt/kg body weight.

As used herein, a "patient" refers to a mammal, in particular a human being.

An "acrylamide polymer" refers to polyacrylamides, polymethacrylamides and copolymers of the two.

The term "Pt complex" indicates a species in which a Pt atom is coordinated with 4, if Pt (II), or 6, if Pt (IV), ligands.

A "chelate" refers to a bidentate ligand that forms a ring with the Pt atom of a Pt complex.

The term "ammine" refers to ammonia, NH$_3$.

The term "primary amine" refers to a compound having the chemical formula R$_a$NH$_2$, wherein the R$_a$ group is selected from the group consisting of an aliphatic, alicyclic, aromatic or heterocyclic group.

The term "secondary amine" refers to a compound having the chemical formula R$_a$R$_b$NH, wherein R$_a$ and R$_b$ are independently selected from the group consisting of an aliphatic, alicyclic, aromatic or heterocyclic group.

The term "tertiary amine" refers to a compound having the chemical formula R$_a$R$_b$R$_c$N, wherein R$_a$, R$_b$ and R$_c$ are independently selected from the group consisting of an aliphatic, alicyclic, aromatic or heterocyclic group.

The term "quaternary ammonium" refers to a compound having the formula R$_a$R$_b$R$_c$R$_d$N$^+$, wherein R$_a$, R$_b$, R$_c$ and R$_d$ are independently selected from the group consisting of an aliphatic, alicyclic, aromatic or heterocyclic group. A quaternary ammonium group requires a counterion, for example, without limitation, chloride(Cl$^-$) or carboxyl (COO_) wherein the latter may be bonded to the molecule of which the quaternary ammonium group is a part (i.e., a zwitterion) or may be external to it, e.g., again without limitation, a physically separated F$_3$CCOO$^-$ group.

As used herein, the term "aliphatic" refers to a straight or branched chain, saturated or unsaturated (i.e., containing one or more double and/or triple bonds) hydrocarbon. Preferably, the aliphatic group consists of 1 to 10 carbon atoms (whenever a numerical range such as "1–10" or "1 to 10" is provided herein, it means that the group may consist of 1 carbon atom, 2 carbon atoms, 3 carbon atoms, etc., up to and including the maximum number of carbon atoms indicated). More preferably at present, it is a lower aliphatic group having 1 to 6 carbon atoms.

As used herein, the term "alicyclic" refers to an aliphatic group in which at least some of the carbons form a ring.

A "hydroxyalkyl" group refers to an aliphatic group that does not contain any double or triple bonds and that is substituted with one or more —OH groups.

As used herein, an "ester-forming moiety" refers to an aliphatic, alicyclic, aralkyl or heteroaralkyl R group that, when covalently bonded to the carboxylate oxygen, i.e., the —C(O)O oxygen, of a carboxyl group creates an ester, i.e, a —C(O)OR group.

As used herein, an "aromatic" group refers to an all-carbon monocyclic or fused-ring polycyclic (i.e., rings which share adjacent pairs of carbon atoms) group having a completely delocalized pi-electron system in the ring. Examples, without limitation, of aryl groups are phenyl, naphthalenyl and anthracenyl.

As used herein, an aralkyl group refers to an aryl group that has an aliphatic group covalently bonded to it, the aliphatic group being the attachment point of the aralkyl group to whatever other entity the group is bonded. Examples of aralkyl groups include, without limitation, benzyl, phenethyl, etc.

As used herein, a "heterocyclic" group refers to a monocyclic or fused-ring group in which one or more of the rings contains one or more atoms selected from the group consisting of nitrogen, oxygen and sulfur. The term includes heteroaromatic groups in which the rings have a fully delocalized pi-electron system that is aromatic by Huckel's rule. Examples, without limitation, of heteroaromatic groups are pyrrole, furan, thiophene, imidazole, oxazole, thiazole, pyrazole, isoxazole, isothiazole, pyridine, pyrimidine, quinoline, isoquinoline, purine and carbazole. The term also includes heteroalicyclic groups in which the rings, while they may include one or more double bonds, do not have a completely delocalized pi-electron system.

As used herein, a "tumor targeting group" refers to a group that delivers a therapeutic compound, e.g., a compound of this invention, selectively to a tumor compared to other tissues. Targeting may be passive, as when taking advantage of the EPR effect, or active, as in the case of conjugates with antibodies, lectins, folic acid, biotin, vitamin $B_{12}$, and analogs thereof such as methotrexate and desthiobiotin.

As used herein, a "water solubilizing group" refers to a group that provides or increases water solubility of molecules comprising O,O—Pt and N,O—Pt amidomalonate chelates, which, in and of themselves, generally have limited solubility in water. Examples of water solubilizing groups include, without limitation, polymers such as poly(hydroxyalkylacrylamide), poly(hydroxyalkyl-methacrylamide and copolymers thereof; polyethylene glycols (PEGs); polypropylene oxides (PEOs); polyvinyl alcohols; poly(vinylpyrolidine); water soluble dendrimers; sugars such as mannose and glucose; ascorbic acid; glycerol; aminoacids and polyaminoacids containing water solubilizing groups such as serine, threonine, glutamic acid, aspartic acid, tyrosine, arginine, citrulline and the like; polysaccharides such as dextrose, dextrin, hydroxypropyl cellulose and carboxymethylcellulose; glycosaminoglycans such as hyaluronic acid, dermatan sulfate, chrondiotin sulfate, heparin; sulfonic acids, sulfonates, quaternary ammonium salts and individual water-solubilizing functional groups such as hydroxy, methoxy, polyols, polyethers, amides and the like.

A "polymer-bound N,O-amidomalonatediamineplatinum (II) complex" refers to a compound in which a Pt(II) is chelated to the amide nitrogen and a carboxylate oxygen of Ama and one or more of such Ama=Pt moieties is/are covalently bonded to a polymeric backbone either directly or through a linker.

A "linker" refers to a group that spatially separates the Ama=Pt chelate from the polymeric backbone. The linker can be any sort of entity, such as, without limitation, a polyethylene glycol, an aminoacid or a polyaminoacid, one end of which is capable of forming a covalent bond with the polymer backbone and the other end of which is capable of forming a covalent bond with Ama.

As used herein, a "cation" refers to any pharmaceutically-acceptable positively charged species including, without limitation, alkali and alkaline earth metal cations and quaternary ammonium groups. In particular, a cation of this invention is selected from the group consisting of $H^+$, $Na^+$, $K^+$, $Li^+$, $Ca^{2+}$, $Mg^{2+}$ and a quaternary ammonium group.

As used herein, an "anion" refers to any pharmaceutically-acceptable negatively charged species including, without limitation, chloride, bromide, iodide, nitrate, sulfate, sulfonate, bicarbonate, carbonate, boron tetraflouride, tetraphenylboron, phosphorus hexafluoride, perchlorate, and the like.

As used herein, an "amino acid" refers to any organic acid having one or more $NH_2$ groups covalently bonded to non-carbonyl carbon atoms, e.g. without limitation, p-alanine, 4-aminobutyric acid, 6-aminocaproic acid, p-aminobenzoic acid and an amine and carboxyl group separated by a PEG spacer. "Amino acid" also refers to all natural and non-natural α-amino acids and to their N-alkyl derivatives.

As used herein, a "polyaminoacid" refers to a linear or branched chain of amino acids connected by peptide linkages. The amino acids that make up the polyaminoacid may be the same or different.

As used herein, "poly(Glu)-Ama-diEt" refers to a polymer in which only a fraction (i.e. 15%) of the carboxyl side chains have been substituted by Ama-diEt groups.

As used herein, "poly(Glu-Ama-diEt)" refers to a polymer where all the carboxyl side chains have been substituted with Ama-diEt groups.

As used herein, "poly(Glu)Ama=Pt(NH$_3$)$_2$" refers to a poly(Glu)-Ama-diEt group wherein the two Et groups have been replaced with a cis-diammine Pt group in which the Pt is also chelated to the two carboxyl groups (O,O'—Pt chelate) or to one of the carboxyl groups and to the nitrogen of the amide group (N,O—Pt chelate) of Ama.

As used herein, "poly(Glu-Ama)=Pt(NH$_3$)$_2$" refers to an Ama-Pt chelate in which only a portion (i.e. 10–15%) of the Ama groups are coordinated to a cis-diammineplatinum(II) species.

As used herein "-Ama=Pt=DACH" refers to a grouping wherein Pt is chelated with Ama either in the O,O'- or the N,O— configuration and is also chelated with the amino groups of 1,2-diaminocyclohexane (DACH).

As use herein "poly(HPMA)-GG-," "poly(HPMA)-GGG-," "poly(HPMA)-GGGG-," "poly(HPMA)-GFLG-," etc, refer to a copolymer of HPMA and acrylamide or methacrylamide to which GG, GGG, GGGG, GFLG, etc. are covalently bonded. That is, for the purposes of this invention, it is understood that GG, for example, actually refers to

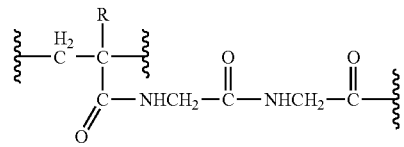

where R is hydrogen or methyl and the C-terminal end of the GG moiety is further substituted with ONp, Ama-diEt, etc. and, ultimately, in the claimed compounds of this invention, amidomalonate O,O'—Pt and/or N,O'—Pt chelates.

By "pH stating" is meant using a device that is capable of maintaining the pH of a solution within a selected range by either continuously or at specified intervals measuring pH of the solution and titering in acid or base as required to bring the pH back into the selected range.

The subscript "r" refers to the actual number of the moieties modified by the subscript; for example, if "r" is 100, it means that 100 of the moieties in the bracket are covalently bonded to $R_1$.

As used herein, the phrase "a water-solubilizing group further comprising one or more tumor-targeting group(s)" refers to both the situation in which the water-solublizing group, in and of itself, may also be a tumor-targeting group and the situation in which one or more tumor-targeting group(s) are appended to a water-solubilizing group. The phrase also refers to a combination of the preceding; that is, the water-solubilizing group may also be a tumor targeting group and, in addition, have one or more separate tumor-targeting groups appended to it.

As used herein, the term "corresponding," when referring to amidomalonate O,O'—Pt and N,O—Pt complexes, simply means that the "corresponding" complexes derive from the same molecule, the primarly difference being that in one case Pt is chelated to the amidomalonate through the two carboxylate oxygen atoms and in the other case Pt is chelated to the amidmalonate through one of the carboxylate oxygens and the amide nitrogen.

ABBREVIATIONS

Ama: amidomalonate
Ama-diEt: diethylamidomalonate
DACH: 1,2-diaminocyclohexane
1R,2R-DACH: 1R,2R-diaminocyclohexane
DCC: dicyclohexylcarbodiimide
DMAP: N,N-dimethylaminopyridine
DMF: dimethylformamide
EDC: 1-(3-dimethylaminopropyl)-3-ethylcarbodiimide hydrochloride
FID: free induction decay
E or Glu: glutamate
F or Phe: phenylalanine
G or gly: glycine
L or leu: leucine
HOBt: hydroxybenzotriazole HPA: 2-hydroxypropylamine
HPMA: N-(2-hydroxypropyl)methacrylamide
MA: methacroyl
MTD: maximum tolerated dose, the highest dose evaluated in which no deaths resulted from drug-induced toxicity.
N,O—Pt: Ama-Pt chelate in which the Pt is bound to the nitrogen of the amide group and to one of the carboxylate oxygens of the amidomalonate moiety O,O'—Pt: Ama-Pt chelate in which the Pt is bound to the two carboxylate oxygens of the amidomalonate moiety
ONp or ONp ester: nitrophenoxy group as in a p-nitrophenol ester
RCF: relative centrifugal force
TFF: tangential flow filtration

DISCUSSION

Figure 3A:
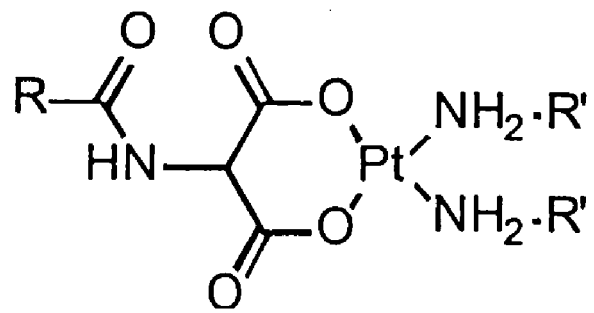
FIG. 3A shows the structure of an O,O'—Pt chelate of amidomalonate-cis-diamineplatinum(II).
Figure 3B:
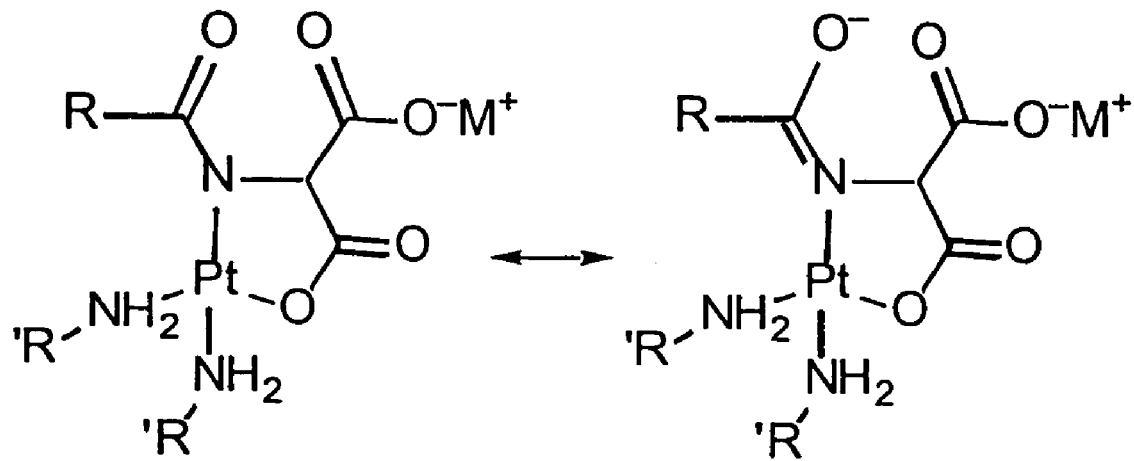
FIG. 3B shows the structure of an N,O—Pt chelate of amidomalonate-cis-diamineplatinum(II).
Figure 4:
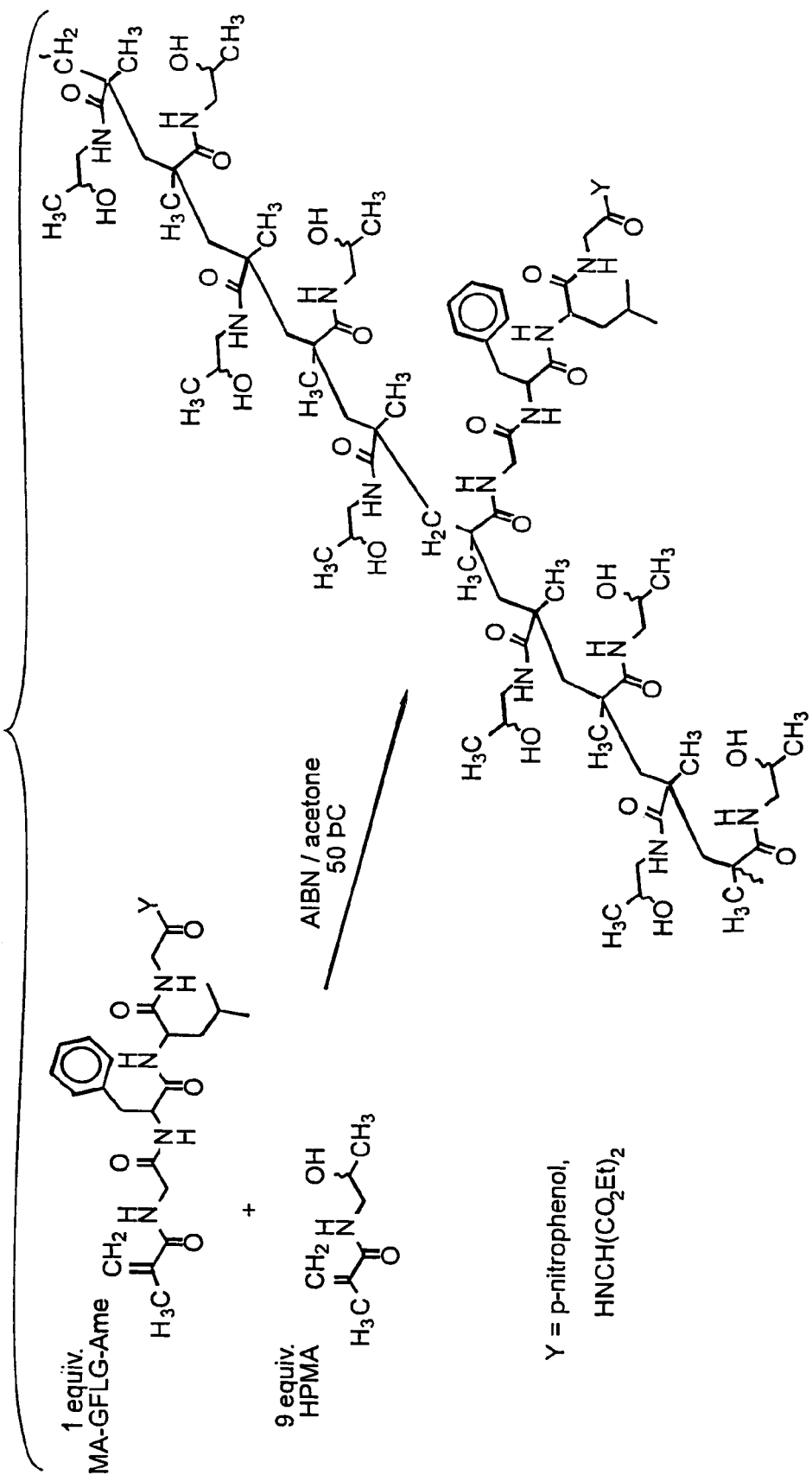
FIG. 4 shows the preparation and structure of poly (HPMA)-GFLG-Y where Y=ONp (ONp=p-nitrophenol ester) or Ama-diEt. When Y=ONp, lower molecular weight polymers with narrower polydispersities are formed. Without ONp groups or with added p-nitrophenol much higher molecular weight poly(HPMA) polymers are obtained. The 351 kDa material came from a reaction without any ONp esters and without any added p-nitrophenol. When p-nitrophenol is added to polymerization without ONp esters, smaller HPMA polymers are obtained with narrower and more uniform molecular weight distributions.
Figure 5:
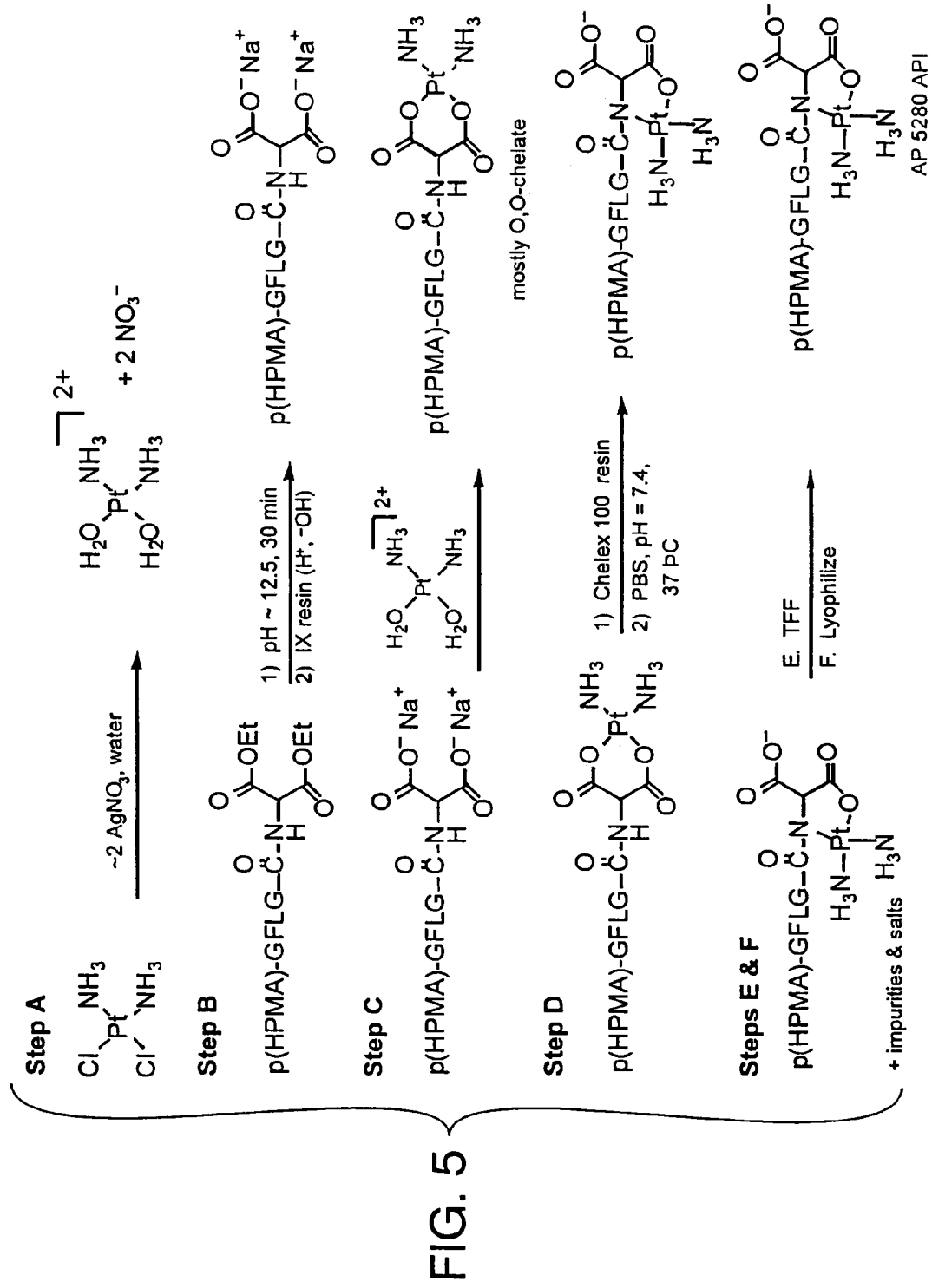
FIG. 5 shows the synthetic scheme for the preparation of poly(HPMA)-GFLG-Ama=Pt(NH$_3$)$_2$ N,O—Pt chelate.

The current invention relates to a method for selectively and reproducibly preparing essentially pure O,O'—Pt chelates (FIG. 3A) or N,O—Pt chelates (FIG. 3B) from the mixture of the two species that is normally obtained from the initial Ama-Pt chelate-forming reaction.

In U.S. Pat. No. 6,692,734, the parent of this application, it was demonstrated that treatment of the initially formed mixture of O,O'—Pt and N,O—Pt amidomalonate chelates with phosphate-buffered saline solution at pH of approximately 7.4 in which the sodium chloride concentration was 65 mM or greater gave the N,O—Pt chelate almost exclusively. Other anions gave similar results. Based on these results, it was postulated that a certain anionic concentration was necessary to effect the conversion of the O,O'—Pt chelate to the N,O—Pt chelate. It has now been discovered that, while anions may be beneficial to the conversion, it is in fact pH that appears to predominate in the determination of which isomer is obtained. In fact, depending on the pH to which the mixture of isomers is subjected, it is possible to completely control the structure of the chelate obtained. That is, at low pH, i.e. 3.5 or lower, the O,O'—Pt chelate predominates, even to the point of complete exclusion of the N,O—Pt chelate, while at a pH of from about 6.0 to about 10.0, the N,O—Pt chelate predominates, likewise to the essentially complete exclusion of the O,O'—Pt chelate. At intermediate pHs, varying ratios of the isomers are obtained with the N,O—Pt chelate becoming more dominant as the pH increases to 6 and above. This is demonstrated in the following tables.

In Table 1, an aqueous solution of predominantly O,O'—Pt chelate of p(HPMA)-GFLG-Ama=Pt(NH$_3$)$_2$ was subjected to various pH ranges at 38° C.

TABLE 1

Starting from 92% O,O-chelate, 8% N,O-chelate p(HPMA)-GFLG-Ama=Pt(NH$_3$)$_2$

| | pH 3.0–3.5 | | pH 4.0–4.5 | | pH 5.0–5.5 | | pH 6.0–6.5 | |
| --- | --- | --- | --- | --- | --- | --- | --- | --- |
| Time | O,O— | N,O— | O,O— | N,O— | O,O— | N,O— | O,O— | N,O— |
| 1 h | 100 | 0 | 75 | 25 | 67 | 33 | 57 | 43 |
| 5 h | 97 | 3 | 79 | 21 | 51 | 49 | 34 | 66 |
| 20 h | 98 | 2 | 72 | 28 | 35 | 65 | 9 | 91 |

As can be seen, at pH 3.0–3.5, the mixture becomes essentially completely the O,O'—Pt chelate while at the pH 6.0–6.5, the O,O'—Pt chelate converts essentially completely to the N,O—Pt chelate. At the intermediate pHs, 4.0–4.5 and 5.0–5.5, increasing amounts of the N,O—Pt chelate are obtained over time.

When 100% N,O—Pt chelate p(HPMA)-GFLG-Ama=Pt(NH$_3$)$_2$ was subjected to the same pH ranges and temperature, the results shown in Table 2 were obtained.

TABLE 2

| | Starting from 100% N,O-chelate p(HPMA)-GFLG-Ama=Pt(NH₃)₂ | | | | | | | |
|---|---|---|---|---|---|---|---|---|
| | pH 3.0–3.5 | | pH 4.0–4.5 | | pH 5.0–5.5 | | pH 6.0–6.5 | |
| Time | O,O— | N,O— | O,O— | N,O— | O,O— | N,O— | O,O— | N,O— |
| 1 h | 98 | 2 | 45 | 55 | 6 | 94 | 0 | 100 |
| 5 h | 100 | 0 | 56 | 44 | 15 | 85 | 0 | 100 |
| 20 h | 100 | 0 | 68 | 32 | 19 | 81 | 0 | 100 |

As can be seen, the N,O—Pt chelate remains essentially intact at the pH 6.0–6.5 and as the pH is lowered some conversion to the O,O'—Pt chelate occurs until at pH 3.0–3.5, conversion of the N,O—Pt chelate to the O,O'—Pt chelate is essentially complete.

To demonstate conclusively that added anions are not necessary to effect the conversion of one isomer to the other, experiments were performed at an intermediate pH range, 5.0–5.5 and 38° C., in the presence of added choride or perchlorate anion. As can be seen, the conversion percentage in the presence of added anion does not differ significantly from that obtained in the complete absence of added anion.

Initially, degassed water and an argon atmosphere were used in the chelate conversion experiments. Degassing and inert atmospheres, however, do not appear to be necessary. In fact, an alternative synthesis of O,O'—Pt chelates was devised in which the chelate mixture initially obtained is not isolated prior to conversion. Instead, after a 1 hour platination period, the pH of the chelate mixture was adjusted to pH 3.0–3.5 in an open atmosphere using non-degassed water to give essentiall pure O,O'—Pt chelate. If, however, an even purer O,O'—Pt chelate is desired, degassed water and an inert atmosphere may be used, although the effect is small.

TABLE 3

| | Starting from 92% O,O-chelate and 8% N,O-chelate at pH 5.0–5.5 | | | | Starting from 100% N,O-chelate at pH 5.0–5.5 | | | |
|---|---|---|---|---|---|---|---|---|
| | 100 mM Cl⁻ | | 100 mM ClO₄⁻ | | 100 mM Cl⁻ | | 100 mM ClO₄⁻ | |
| Time | O,O— | N,O— | O,O— | N,O— | O,O— | N,O— | O,O— | N,O— |
| 1 h | 69 | 31 | 69 | 31 | 9 | 91 | 10 | 90 |
| 5 h | 46 | 54 | 44 | 56 | 8 | 92 | 12 | 88 |
| 8 h | 32 | 68 | 33 | 67 | 11 | 89 | 23 | 77 |
| 22 h | 32 | 68 | 40 | 60 | 13 | 87 | 25 | 75 |

The above phenomenon appears to be general, similar results having been obtained with Pt=DACH analogs (data not shown). Whenever an N,O—Pt amidomalonate DACH chelate is subjected to pHs below 6.0, it rearranges to the O,O'—Pt amidomalonate DACH chelate, the conversion being more rapid and more complete as the pH is lowered. Similarly, when an O,O'—Pt amidomalonate DACH chelate is subjected to pHs above 3.5, it begins to convert to the N,O—Pt amidomalonate DACH chelate until, at pH 6.0 and above, the conversion to the N,O—Pt chelate is complete. A difference observed between DACH chelate and cis-diammine chelate conversion appears to be that the former, when in the N,O—Pt chelate form, does not convert to the O,O'—Pt chelate as completely as does the latter. On the other hand, DACH chelates convert more rapidly and fully from O,O'—Pt to N,O—Pt chelates than do the cis-diammines, the former being essentially completely converted in approximately 8 hours compared to at least 20 hours for the latter (data not shown).

There are at least two advantages to being able to essentially completely control which isomer of an Ama-Pt chelate of a compound of this invention is obtained. First, the method disclosed herein provides essentially pure compounds that should meet regulatory requirements for registration as chemotherapeutic agents. Second, the therapeutic index of the compound can be controlled to meet the needs of a particular treatment protocol. That is, it was previously shown (U.S. Pat. No. 6,692,734) that N,O—Pt chelates exhibit substantially higher MTDs and, by extension, better therapeutic indices, than the corresponding O,O'—Pt chelates. While not being held to any particulat theory, this is presently thought to be due to the fact that O,O'—Pt chelates release active small-molecule Pt compounds more rapidly than do N,O—Pt chelates. This is demonstrated by the experiment carried out in Example 31 wherein poly(HPMA)-GFLG-Ama-Pt(NH₃)₂, 100% N,O-chelate, approx. 20 kDa was subjected to various pH ranges. The results are shown in Table 4.

TABLE 4

| Time (h) | pH 3.4 | pH 4.4 | pH 5.4 | pH 6.4 | pH 7.4 | pH 8.2 |
|---|---|---|---|---|---|---|
| 1 | 2.0% | 0.9 ± 0.1% | 0.5% | 0.4% | 0.36 ± 0.01% | 0.39 ± 0.0% |
| 2 | 4.2 ± 0.1% | 1.9% | 0.9 ± 0.08% | 0.7 ± 0.07% | 0.5 ± 0.07% | 0.7 ± 0.08% |

TABLE 4-continued

| Time (h) | pH 3.4 | pH 4.4 | pH 5.4 | pH 6.4 | pH 7.4 | pH 8.2 |
|---|---|---|---|---|---|---|
| 4 | 6.6% | 3.3 ± 0.4% | 1.4 ± 0.2% | 0.9 ± 0.06% | 0.7 ± 0.04% | 0.7 ± 0.04% |
| 8 | 12.0 ± 0.1% | 5.1 ± 1.2% | 2.6 ± 0.4% | 1.3 ± 0.1% | 0.9 ± 0.02% | 0.8 ± 0.16% |
| 24 | 29.1 ± 3.9% | 17.0 ± 3.6% | 7.3% | 2.7 ± 0.1% | 1.6 ± 0.0% | 1.8 ± 0.02% |

As can be seen. at pHs above about 6.0, very little Pt is released even after 24 hours. On the other hand, 12% is released at 8 hours and 30% at 24 hours at pH 3.4. In Tables 1–3, it was demonstrated that N,O—Pt chelates convert to O,O'—Pt chelates at lower pHs while O,O—Pt chelates converts to N,O—Pt chelates at higher pHs and, furthermore. N,O—Pt chelates are relatively stable at pHs over 6.0. It would thus be expected that the 100% N,O—Pt chelate, when subjected to pH 6.4, 7.4 and 8.2 in Example 31, would remain intact as the N,O—Pt chelate. On the other hand, at pH 3.4, Table 1–3 demonstrate that a fairly rapid conversion of the N,O—Pt chelate to the O,O'—Pt chelate occurs. At intermediate pHs 5.0–5.5, Tables 1–3 indicate that the N,O'—Pt chelate loses some of its stability and begins to convert to the O,O'—Pt chelate. In Table 4, at pH 6.4, 7.5 and 8.2, very little Pt is released supporting the hypothesis that N,O—Pt chelates do not readily release Pt and at pH 3.4, a substantial amount of Pt is released supporting the hypothesis that O,O'—Pt chelates release Pt much more efficiently. At the intermediate pH of 5.4, Tables 1–3 show that N,O—Pt chelate is converting to O,O'—Pt chelate, but at a slower rate than at the lower pH and in Table 4, intermediate amounts of Pt are released.

In a physiological context, the above suggests the following: both neoplastic and normal cells contain lysosomes, organelles that contain enzymes that lyse various substrates. These enzymes require activation by exposure to an acidic environment. Lysosomes provide the requisite environment; their interior pH is around 5.0. The disclosures herein would predict that an N,O—Pt chelate entering a lysosome would convert in significant quantities to an O,O'—Pt chelate and the latter would then release active, small molecule Pt species. The polymer- or macromolecule-bound N,O'-chelates of this invention would be expected to preferentially accumulate in tumors and to encounter the lysosomes of the cells therein. The acidic environment would result in conversion of the compound to the O,O'—Pt chelates, which then would release active small molecule Pt species that, in turn, would kill the cells and eventually the tumor. On the other hand, the polymer-/macromolecule-bound N,O-chelates would have limited access to the cells (and lysosomes) of normal organs due to their greater structural integrity and would therefore be relegated to circulating through the vascular system, the physiological pH of which (approx 7.4) would result in the compound remaining in the relatively non-toxic N,O—Pt chelate form.

EXAMPLES

Chemicals

Cisplatin, pyridine, ethanol, ethyl acetate, diethyl ether, diethylamino-malonate HCl salt, diethyl N-acetamidomalonate, $AgNO_3$, NaOH, IR,2R-diaminocyclohexane, polyglutamate-Na salt, KI and PBS were supplied by Sigma-Aldrich USA. The solvents used were HPLC grade and the reagents were ACS grade or better. The ion exchange resins, AG 501-X8(D) H[+], HO[−] forms, AG 50W-X8H[+], and Chelex 100 Biotech grade, were supplied by Bio-Rad Laboratories. Class 1 water was obtained using a Milli-Q water system. $K_2PtCl_4$ was supplied by All-Chemie Ltd., Mt. Pleasant, S.C. Filter-aid 289 pulp was obtained from Schleicher and Schuell. Poly(HPMA)-GFLG-ONp, poly(HPMA)-GFLG-Ama-diEt (45 kDa), and poly(HPMA)-GFLG-Ama-diEt (351 kDa) were synthesized by Polymer Laboratories, Shropshire, UK. Aminoacid analysis and MALDI-TOF-MS were performed by Peptide Technologies Corp. Gaithersburg, Md.

Apparatus and Instrumentation

Depending on the scale, 0.2 μm sterile filtrations were performed with either a 25 mm Whatman GD/X PVDF syringe filter, a Steritop media bottle filter with a GP Express membrane from Millipore, or a Millipak inline filter with a PVDF membrane from Millipore. A laminar flow hood with UV light was used for sterile operations. pH was measured with a Beckman Phi-34 pH meter with a gel electrode calibrated at pH 4 for low pH measurements and at pH 10 for high ones. Static electricity in lyophilized solids was neutralized with a Zerostat gun (Aldrich), guided by an electrostatic field meter from SIMCO, Hatfield, Pa. Platinum was analyzed by ICP-OES using a Jobin Yvon JY24 spectrometer on samples and standards diluted to 1–60 ppm in 3% $HNO_3$. Water was determined by Karl Fisher titration using an Aquastar C2000 from EM Science. Elemental analysis for Na, Cl, and P were performed by Desert Analytics, Tucson, Ariz. $^1$H NMR spectra were obtained on a 400 MHz Unity/Inova system from Varian, Inc. [195]Pt NMR spectra were obtained on a 300 MHz Mercury system from Varian or a 300 MHz Avance Bruker system. Lyophilizations were performed using a Freezemobile 12EL from Virtus.

Aliquot Purification for Percent O,O'—Pt and N,O—Pt Chelates

The percent of O,O'- and N,O-chelate in timed aliquots of reactions mixtures were determined by removing enough of the reaction mixture (4–15 mL depending on concentration) to give greater than 100 mg of Pt-chelate if only [195]Pt NMR spectroscopy was to be done or about 200 mg if % Pt, and % $H_2O$ were also to be determined. The aliquots were purified by ultrafiltration using a Centricon Plus-20 centrifugal filter with a 5 kDa Biomax membrane from Millipore. The charged device was spun at the recommended RCF until less than 1 mL remained. The filtrate was discarded, the retentate was diluted with 15–18 mL water and the sample was centrifuged. This was repeated once more, and the retentate was lyophilized to give the sample for analysis.

Platinum Release from PBS

The percent of small platinum species released over time was measured by dissolving about 30 mg of the polymer-platinum conjugate in 15 mL of phosphate buffered saline (10 mM phosphate, 123 mM Cl[−]) and incubating the solution at 37° C. in a water bath. At indicated times, 2.0 mL aliquots were transferred to a centrifugal filter with a 3 kDa nominal molecular weight cutoff (Centricon YM-3 from Millipore) and spun until >1.5 mL of filtrate had accumulated. The timed filtrates and the original solution were analyzed for platinum by ICP-OES. The percent of small Pt species released was determined using the formula: ((ppm Pt in filtrate)/(ppm Pt in stock solution))×100.

Size Exclusion Chromatography

N,O—Pt chelates were analyzed on an SEC system consisting of an HPLC instrument equipped with two PL Aquagel-OH Mixed 8 μm columns (from Polymer Labs) in column ovens at 35° C. and an RI detector. The mobile phase, consisting of a 35/65 mixture of MeOH/H$^2$O with 10.0 mM LiClO$_4$, was pumped at 1.0 mL/min. The column was calibrated with PEO/PEG standards and results were fit to a $4^{th}$ order polynomial of log($M_p$) as a function of reciprocal retention time. The reported values for $M_w$, and $M_n$ represent the average of three determinations of 100 μL of a 2 mg/mL sample dissolved in the mobile phase.

Tangential Flow Filtration

At scales larger than about 2 grams, O,O'—Pt and N,O—Pt chelates of polymers were purified by tangential flow filtration (TFF) using membranes with areas of 0.05–0.1 m$^2$ made of Biomax polyethersulfone with a 5 kD nominal molecular weight cutoff. Prior to filtration the system was cleaned and sanitized by pumping 0.1 N NaOH for 30–60 minutes at the recommended flow rate. The caustic was removed and fresh Milli-Q water was circulated until the pH of the retentate and permeate was essentially neutral (pH <8). The permeate flow rate was measured at an inlet pressure of 2.0 bar and an outlet pressure of 0.35 bar. Milli-Q water was also used as the makeup water.

NMR Spectroscopy $^{195}$Pt NMR spectra were obtained from a filtered 0.70 mL solution in 93/7 H$_2$O/D$_2$O in a 5 mm tube. Enough sample (80–120 mg) was used to give a solution that was >50 mM in platinum. The probe was tuned for each sample. A pulse width of 90 degrees, an acquisition time of 10 msec, a spectral window of 100 kHz and no delay was used. The transmitter was tuned to approximately midway between the O,O'—Pt and N,O—Pt chelates shifts (−1896 ppm for cis-diammine Pt and at −2450 for DACH—Pt). Between 50,000 and 1 million transients were typically required to obtain a sufficient (>35:1) s/n ratio for the cis-diammine-Pt and DACH=Pt species, respectively. The resulting FID was increasingly left-shifted until a flat baseline was obtained, a 100 Hz line broadening was applied, and a Fourier fill of 2048 was applied before processing. Integral regions were set and the spectrum's baseline was subjected to a spline fit using VNMR software v6.1. The sample was referenced externally to a 100 mM sample of K$_2$PtCl$_4$ in 95/5H$_2$O/D$_2$O and 100 mM HCl at −1624 ppm. This was also used to determine the 90 degree pulse width and T1.

$^{13}$C NMR spectra were obtained using the same sample used for the $^{195}$Pt NMR. An acquisition time of 0.50 sec, a delay of 3.0 sec, about 70 degree pulse width and 5000–10000 transients were collected and a 3.5 Hz line broadening was applied. A s/n of >100 was typically obtained. Aqueous samples were referenced externally to 1,4-dioxane in 93/7H$_2$O/D$_2$O at 67.19 ppm. Other samples were referenced to the solvent peak.

$^1$H NMR spectra were referenced to TMS or TMSP and obtained using standard parameters. Pre-saturation of the HOD signal was often used. Coupling constants (J) are in Hertz.

The following examples, which further illustrate the invention herein, are not intended, nor are they to be construed, to limit the scope of this invention in any manner whatsoever.

Example 1

Preparation of poly(HPMA)-GFLG-Ama-diEt, about 25 kDa

An oven-dried 1 L round bottom flask with magnetic stir bar was fitted with a septum and cooled under vacuum. Once cooled, nitrogen was introduced, the septum was removed and 29.79 g (140.8 mmol) of diethylaminomalonate HCl salt was added. The septum was replaced and 800 mL of anhydrous pyridine was cannulated into the flask. One-third of 50 g of poly(HPMA)-GFLG-ONp (Compound I, FIG. 1A of U.S. Pat. No. 5,965,118) was added. When nearly dissolved, the next third of the ONp-polymer was added. When the second third was nearly dissolved, the last third of the ONp-polymer was added.

Figure 6:
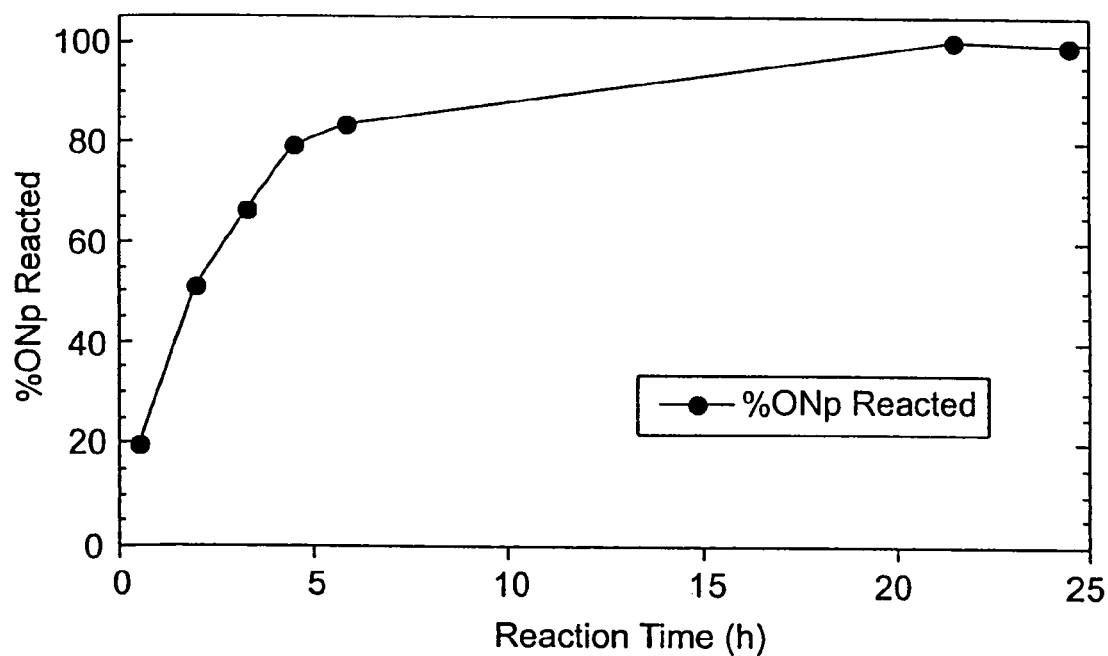
FIG. 6 shows the release of p-nitrophenol during preparation of poly(HPMA)-GFLG-AmadiEt. This is one way in which the substitution reaction can be monitored by the release of a small molecule.

The reaction was monitored by HPLC for free and total p-nitrophenol using a C18 column, a pH 4.5 MeCN mobile phase and UV detection at 316 nm. Aliquots were analyzed for free p-nitrophenol and for total p-nitrophenol after base hydrolysis (pH 12, 5 minutes). After stirring at about 23° C. for 20–24 hours, the reaction was essentially complete (FIG. 6).

The reaction mixture was heated at 40–45° C. in a water bath for 3 hours, cooled to ambient temperature, and pyridine was removed in vacuo at <40° C. The residue was dissolved in absolute EtOH to give a 25% wt/vol. solution. The crude product was precipitated with 2.5 L dry EtOAc and 0.5 L diethyl ether. The mixture was stirred for 3–5 hours and then filtered through a medium glass frit. The residue was washed three times with about 100 mL of ether and dried under a rubber dam to give 57–59 g. of a pale yellow solid which was dissolved in 500 mL EtOH after which 3.1 g AG 501-X8(D) IX resin (H$^+$ and OH$^-$ forms) per gram of filter cake was added. The mixture was stirred gently for 2.5 hours and then filtered to remove the resin. The volume of EtOH was reduced to a give a 25% wt/vol solution and the product was precipitated. The product was collected and washed to give 45–46 g of pale yellow solid. $^1$H NMR showed peaks characteristic of the Ama-diEt group and no small molecules except for <1% each of EtOH and EtOAc.

Amino acid analysis (molar ratio of gly:HIPA:leu:phe): 3.1:7.1:1.0:1.2; $^1$H NMR (D$_2$O) δ7.2–7.4 (br s, 5, ArH), 4.66 (br s, 1, α-H-phe), 4.31 (br s, 5, α-H-leu, and OCH$_2$CH$_3$), 4.1–3.8 (tall s and short m, ~13, —NHCH$_2$CH(OH)CH$_3$ and —NHCH$_2$CO$_2$$^-$) 3.3–2.9 (m, —NHCH$_2$CH(OH)CH$_3$ and phe-CH$_2$), 2.25–1.2 (m, —CH$_2$— of polymer backbone, CH$_2$ and CH of leu), 1.20 (br s, ~31, —NHCH$_2$CH(OH)CH$_3$, and —OCH$_2$CH$_3$), 0.99 (s, CH$_3$— of polymer backbone), 0.93 and 0.87 (sh and s, 6, leu-CH$_3$).

Example 2

Preparation of cis-diamminediaquaplatinum (II) dinitrate

A suspension of cisplatin(8.996 g, 29.98 mmol), AgNO$_3$ (9.959 g, 58.62 mmol), 3–5 drops of 5% HNO$_3$, and 190 mL of water were stirred overnight at ambient temperature in a foil-covered low actinic media bottle and then heated at 60–65° C. for 3.5 hours. After cooling to <30° C., the mixture was filtered through a 0.22 μm filter to give a clear solution having a pH of 2. Pt and Ag analyses (ICP-OES) were typically in the range of 15,000–25,000 ppm Pt and 4–14 ppm Ag. Each preparation was analyzed for Pt, and just prior to use was heated to 55° C. for 5 minutes and then cooled to ambient temperature.

A preparation of the di-$^{15}$N isotopomer of cis-diamminediaquaplatinum(II) dinitrate showed a $^{195}$Pt NMR triplet at −1582 ppm, which closely matches the literature value of −1580 ppm reported by Appleton, et al., 1989.

Example 3

Preparation of poly(HPMA)-GFLG-Ama=Pt(NH$_3$)$_2$ O,O'—Pt chelate

A. Hydrolysis of poly(HPMA)-GFLG-Ama-diEt

To 200 mL of water in a 1 L media bottle equipped wit a stir bar, 45 g of poly(HPMA)-GFLG-Ama-diEt (19.35 mmol Ama-diEt residues) was added. After vigorous stirring was established, 135 ml water was added to give a 12–13% (wt/v) mixture. After dissolution was achieved (1–2 hours), 27 mL (54 mmol) of 2 N NaOH was added to raise the pH to 12.5–12.7. The pH was maintained in this range for 30⁻ min. and then 45 g of AG 50i-X8(D) IX resin (H$^+$ and OH$^-$) were added. When the pH decreased to less than 7, the resin was removed by sterile filtration. The pH of the filtrate was raised to 7.6 with 2 N NaOH to give a solution of poly (HPMA)-GFLG-Ama-(CO$_2^-$Na$^+$)$_2$.

B. Preparation of poly(HPMA)-GFLG-Ama=Pt(NH$_3$)$_2$, O,O'—Pt chelate.

To the above pH 7.6 solution was added 199 mL of a 590.9 mM (22,940 ppm Pt) solution of cis-diamminediaquaplatinum(II) dinitrate to give a reaction mixture with a pH of 5.0±0.1. While stirring overnight, the pH dropped to about 4.2 and a small amount of precipitate formed. After 16–18 hours, 17 g of Chelex 100 resin was added and the mixture stirred for 1.5 hours. Before filtration, about 0.5 g filter aid pulp was added and dispersed. The mixture was filtered through a coarse glass frit. An aliquot of the filtrate containing about 125 mg of product was removed, filtered through a 0.2 μm membrane, and purified by centrifugal ultrafiltration. The retentate was lyophilized to give about 110 mg of product.

$^1$H NMR (D$_2$O) δ 7.6 and 7.55 (br s, exchanges, NH), 7.4 and 7.3 (br s, 5, ArH), 5.9 (br s, partially exchanges, 0.2, NH-Ama) 4.65 (br s, 1, α-H-phe), 4.37 (br s, I, α-H-leu), 4.05 (sh, NH$_3$ or CH$_2$ of gly), 4.1–3.8 (tall s and short m, ~13, —NHCH$_2$CH(OH)CH$_3$, —NHCH$_2$CO$_2$—), 3.35–2.9 (br m, —NHCH$_2$CH(OH)CH$_3$ and phe-CH$_2$), 2.25–1.2 (m, —CH$_2$— of polymer backbone, CH$_2$ and CH of leu), 1.20 and 1.19(s, ~27, —NHCH$_2$CH(OH)CH$_3$), 0.99 (s, CH$_3$— of polymer backbone), 0.9 (sh, 6, leu-CH$_3$); $^{13}$C NMR (93/7H$_2$O/D$_2$O) δ 180.1, 179.8, 179.6, 175.0, 174.2, 173.3, 171.5, 171.1, 170.7, 136.6, 129.8, 129.4, 127.8, 66.5, 66.3, 59.6, 55.6, 54.7, 53.0, 47.9, 46.7, 46.0, 45.6, 43.1, 40.5, 37.8, 24.9, 23.1, 21.6; $^{195}$Pt NMR (93/7H$_2$O/D$_2$O) δ −1587, −1733, −2020, and −2056 with area ratios of 1:38:1:4. Analysis shows this material to contain about 9% Pt, 5–10% water, and 0.02% Na.

Example 4

Preparation of poly(HPMA)-GFLG-Ama=Pt(NH$_3$)$_2$, N,O—Pt chelate

A. O,O'—Pt to N,O—Pt chelate Conversion.

Figure 7:
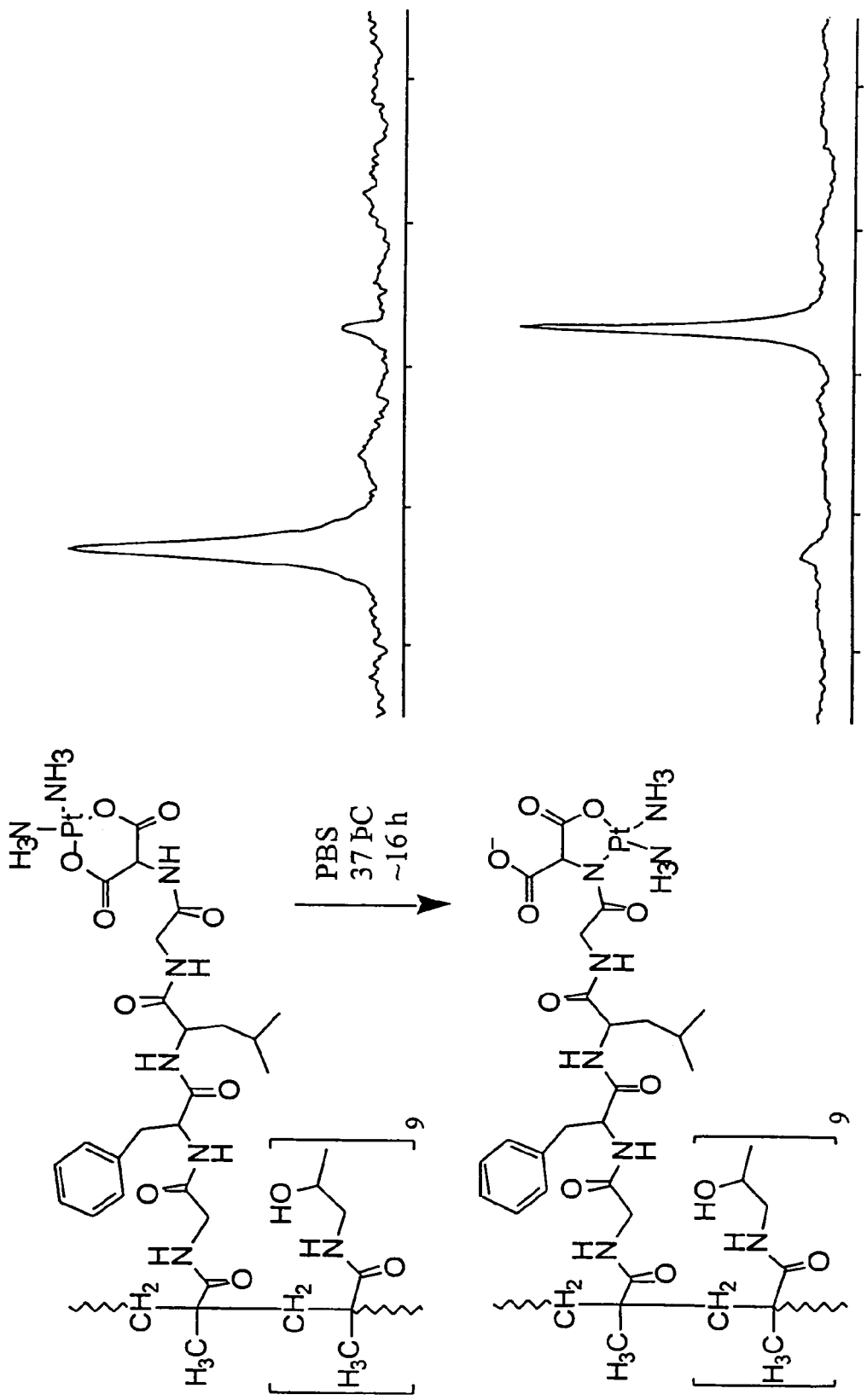
FIG. 7 shows the structures of the O,O'—Pt and N,O—Pt chelates of poly(HPMA)-GFLG-Ama=Pt(NH$_3$)$_2$ and their corresponding $^{195}$Pt NMR spectra. The spectra show the difference in the peak positions of the two chelates. The spectrum of the O,O'—Pt chelate shows it to consist of about 85% O,O'—Pt and 15% N,O—Pt chelate. The spectrum of the N,O—Pt chelate shows it to consist of about 10% O,O'—Pt and 90% N,O—Pt chelate.
Figure 8:
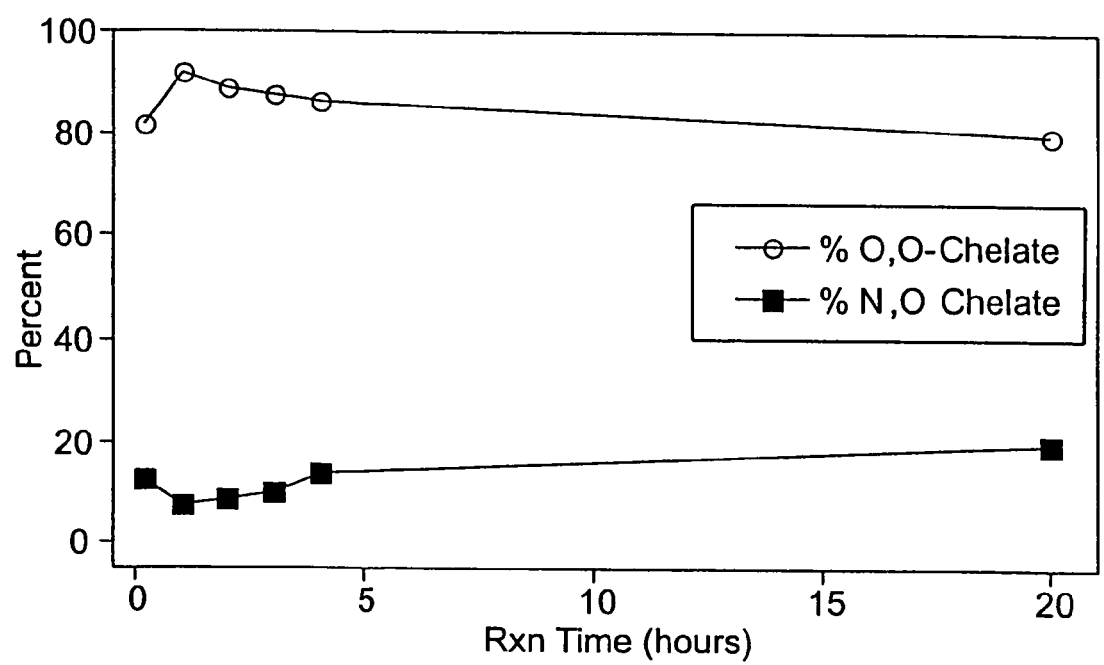
FIG. 8 shows a plot of the percent O,O'—Pt and N,O—Pt chelates during Step C in FIG. 5. This indicates that the O,O'—Pt chelate formation is complete within 1–2 hours.

After filtration of the Chelex 100 resin from Example 3 to give about 1 L of filtrate, the solution was made 100 mM in NaCl and 75 mM in phosphate (pH=7.4) by adding 5.85 g (100 mmol) of NaCl, 16.35 g (61 mmol) of Na$_2$HPO$_4$.7H$_2$O and 1.93 g (14 mmol) of NaH$_2$PO$_4$. The pH was adjusted to 7.4 with 1 N NaOH or 5% HNO$_3$, sterile filtered and washed with buffer of the same concentration into a sterile media bottle to give 1.2 L of solution and the bottle was capped with a 0.22 μm membrane screw-cap. The solution was warmed to 37–38° C. in a water bath and then placed in an oven at 37° C. for 22 hours. At this point $^{195}$Pt NMR spectroscopy of an aliquot purified by ultrafiltration showed the platinum chelate to be ≧95% N,O—Pt chelate and <5% O,O'—Pt chelate (FIG. 7).

B. TFF Purification and Lyophilization of the N,O—Pt chelate.

The 1.2 L of N,O—Pt chelate was purified by TFF as described elsewhere herein. The retentate, a clear dark-red solution, was sterile filtered and lyophilized to give 41.4 g of a red brown solid: % Pt=7.9±0.15, 5.6%, 1.07% Na, <0.05% P, 0.07% C!; $^1$H NMR (D$_2$O) δ 7.4 and 7.3 (br s, 5, ArH), 5.23 (br s, partially exchanged, CH of Ama), 4.65 (br s, 1, α-H-phe), 4.37 (br s,1, α-H-leu), 4.05 (sh, NH$_3$ or CH$_2$ of gly), 4.1–3.8 (tall s and short m, ~13, —NHCH$_2$CH(OH)CH$_3$, —NHCH$_2$CO$_2$—) 3.35–2.9 (m, —NHCH$_2$CH(OH)CH$_3$ and phe-CH$_2$), 2.25–1.2 (m, —CH$_2$— of polymer backbone, CH$_2$ amd CH of leu), 1.20 and 1.19 (s, ~27, —NHCH$_2$CH(OH)CH$_3$), 0.99 (s, CH$_3$— of polymer backbone), 0.93 and 0.87 (sh and s, 6, leu-CH$_3$); $^{13}$C NMR (93/7H$_2$O/D$_2$O) 6186.5, 185.0, 180.1, 179.9, 179.6, 176.3, 175.2, 175.0, 174.6, 174.4, 174.0, 173.9, 173.2, 171.4, 171.0, 136.6, 129.8, 129.4, 127.8, 71.0, 66.5, 66.3, 55.6, 54.7, 52.8, 47.9, 46.0, 45.6, 41.8, 40.5, 37.9, 24.8, 23.1, 21.5, 20.9, 20.7, 18.7, 17.3; $^{195}$Pt NMR (93/7H$_2$O/D$_2$O, 64.4 MHz) δ −1733 (v br s, O,O'-chelate), −2056 (s, N,O-chelate), ratio of O,O'— to N,O is <5:>95; SEC M$_p$=24.5, Mw=24.3 kDa, Mn=15.7 kDa, and Mw/Mn, =1.55; Pt release in PBS 37° C., 0.6% at 3 hours, 2.0% at 24 hours).

Example 5

Preparation of poly(HPMA)=GFLG-Ama=Pt=DACH, O,O'—Pt chelate

A. Preparation of cis-diaqua-1R,2R-DACH=Pt(II) dinitrate

A 125 mL Erlenmeyer flask containing 3.65 g (8.79 mmol) K$_2$PtCl$_4$ and 37 mL water was warmed to give a brown-red solution to which a solution of 5.84 g (35.2 mmol) KI in 6 mL water was added to give a dark red solution. After cooling to ambient temperature, 0.962 g of 1R,2R-diaminocyclohexane was added. A yellow precipitate immediately formed. After stirring for 3 hours at 25° C. the mixture was cooled to 4° C. and held overnight. The precipitate was collected and washed with cold water, EtOH and ether to give 4.98 g of cis-I$_2$Pt-1R,2R-DACH. Next, 1.00 g (1.776 mmol) of cis-I$_2$Pt-1R,2R-DACH, 0.5898 g (3.472 mmol) AgNO$_3$, and 16 mL of water were combined in a vessel protected from light and stirred at ambient temperature overnight and then at 60–65° C. for 3.5 hours. Upon cooling to ambient temperature, the AgCl was removed by filtration and washed once with a small amount of water. Analysis of the filtrate by ICP-OES showed that it contained 13,500 ppm Pt (69.1 mM) cis-(H$_2$O)Pt-1R,2R-DACH.

B. Preparation of poly(HPMA)-GFLG-Ama=Pt=DACH, O,O'—Pt chelate

Poly(HPMA)-GFLG-Ama-diEt (2.80 g, 1.232 mmol Ama-diEt groups) was hydrolyzed and neutralized to give a pH 7.6 solution of poly(HPMA)-GFLG-Ama-(CO$_2$Na)$_2$. To this was added an aqueous solution of 1.48 mmol cis-(H$_2$O)$_2$ Pt-1R,2R-DACH dinitrate salt and the mixture was stirred at ambient temperature overnight. A precipitate that formed was removed by sterile filtration after addition of 0.1 g of filter aid pulp. Next, one third of the reaction was treated with 0.3 g of Chelex resin for 90 minutes, sterile filtered and then purified by centrifugal ultrafiltration. The sample was lyophilized to give 0.71 grams of a red-brown solid: 8.7% Pt, 4.2% H$_2$O; $^1$H NMR (D$_2$O, 400 MHz) δ 7.7 and 7.6 (br s, ~5, NH), 7.4 and 7.3 (br s, 5, ArH), 5.86 (s, 1.6), 4.65 (br s, 1, αH-phe), 4.39 (br s,1, αH-leu), 4.1–3.8 (brm, 4, —NHCH$_2$CO$^{2-}$) 3.95 (br s, 9, NHCH$_2$CH(OH)CH$_3$,), 3.3 5–2.9 (m, 20, NHCH$_2$CH(OH)CH$_3$ and phe-CH$_2$), 2.6–2.3. (br s, N—CH-DACH), 2.25–1.2 (m, —CH2— of polymer backbone, CH$_2$ and CH of leu and DACH), 1.45–0.8 (br s and m, ~97, —NHCH$_2$CH(OH)CH$_3$, CH$_3$— of polymer backbone, leuCH$_3$, and DACH); $^{13}$C NMR(H$_2$O/D$_2$O 93/7) δ 180.0, 175.2, 174.1, 173.3, 171.8, 170.7, 136.8, 129.9, 129.5, 128.6, 128.0, 66.5, 66.3, 63.4, 5.5, 54.7, 52.8, 47.9, 46.7, 46.0, 45.6, 43.5, 40.5, 37.4, 32.4, 24.8, 23.2, 21.5, 20.9, 20.8, 18.6, 17.6, and 17.2; $^{195}$Pt NMR (H$_2$O/D$_2$O 93/7) δ −1900 (vbr s, barely perceptible, O,O'—Pt=DACH); Pt release in PBS, 37° C.: 6.0% at 3 h, 10.9% at 24 h.

Example 6

Preparation of poly(HPMA)-GFLG-Ama=Pt=DACH, N,O—Pt chelate

The remaining two thirds of the reaction mixture from Example 5 was stirred with 0.6 g Chelex resin for 90 minutes and then sterile filtered. The clear solution was made 110 mM in NaCl and 85 mM in phosphate (pH=7.4). The solution was held at 37–38° C. for 22 hours, then purified by centrifugal ultrafiltration and lyophilized to give 1.33 g of a red-brown solid: 8.1% Pt, 7.1% H$_2$O; $^1$H NMR (D$_2$O, 400 MHz) δ 7.4 and 7.3 (br s, 5, ArH), 5.17 (s, 0.3), 4.65 (br s, 1, αH-phe), 4.38 (br s,1, αH-leu), 4.1–3.8 (br m, 4, —NHCH$_2$CO$_2$$^-$) 3.95 (br s, 9, —NHCH$_2$CH(OH)CH$_3$,), 3.35–2.9 (m, 20, NHCH$_2$CH(OH)CH$_3$ and phe-CH$_2$), 2.6–2.2. (brm, N—CH-DACH), 2.25–1.2 (m, —CH$_2$— of polymer backbone, CH$_2$, CH of leu, and DACH), 1.45–0.8 (br s and m, ~100, —NHCH$_2$CH(OH)CH$_3$, CH$_3$— of polymer backbone, leuCH$_3$, and DACH); $^{13}$C NMR (H$_2$O/D$_2$O 93/7) δ 186.8, 185.3, 180.0, 175.1, 174.6, 174.1, 173.5, 171.5, 171.1, 136.7, 129.9, 129.5, 127.9, 70.2, 66.5, 66.3, 64.2, 63.3, 61.0, 55.6, 54.7, 52.9, 47.9, 56.7, 46.0, 45.6, 44.2, 43.3, 41.2, 40.5, 37.9, 32.7, 24.8, 24.6, 23.1, 21.5, 20.9, 20.7, 18.6, 17.3; $^{195}$Pt NMR (H$_2$O/D$_2$O 93/7) δ −2293, no peak at −1900, and no other peaks; Pt release in PBS, 37° C.: 2.0% at 3 hours, 2.1% at 24 hours.

Example 7

Preparation of poly(Glu)-Ama-diEt

To a bottle containing 0.5 g (3.29 mmol —CO$_2$ groups) of polyglutamate and a stir bar, 104 mg (0.493 mmol) of diethylaminomalonate HCl salt, 3 mg DMAP and 10 mL dry DMF (HPLC grade, >48 h over 4A sieves) was added in a dry box and the contents stirred to give a cloudy mixture. Next, 315 mg (1.36 mmol) DCC was added, a septum was inserted into the mouth of the bottle, 2 mL of 1.0 M HCl in ether was added and the mixture was stirred overnight at ambient temperature. About 15 mL of CHCl$_3$ was added and the cloudy mixture was centrifuged at 3850 RCF for 15 min. The supernatant was discarded and the white gel that remained was stirred with 2.5% NaHCO$_3$ for 30 minutes. The mixture was centrifuged and the supernatant was lyophilized to give 1.91 g of white solid, the $^1$H NMR spectrum of which showed the presence of DMF, EtOH, DCC/DCU and peaks for polyglutamate, diethylamidomalonate, and diethylaminomalonate (the peak areas at 4.3 ppm (α-CH of glu and —OCH$_2$CH$_3$) and 2.4 ppm (a CH$_2$ of glu) are at a ratio of about 1:1 whereas in polyglutamate the ration is 1:2). The material was dissolved in water and purified by centrifugal ultrafiltration to give 216 mg of a white solid, the $^1$H NMR spectrum of which indicated the presence of DCC/DCU. Also, addition of NaOD to a solution of the material in D$_2$O liberated EtOH corresponding to 0.67 mmol Ama-diEt groups per gram of poly(glu)-Ama-diEt. This was used in Example 8 without purification.

Example 8

Preparation of poly(Glu)-Ama=Pt(NH$_3$)$_2$, O,O'—Pt and N,O—Pt chelates

A. Preparation of poly(glu)-Ama=Pt(NH$_3$)$_2$O,O'—Pt chelate

To 4 mL of water in a 20 mL vial equipped with a stir bar, 188 mg (0.126 mmol Ama-diEt equiv.) of poly(glu)-Ama-diEt from Example 7 was added. Once dissolved, the pH was raised to 12.4–12.8 for 20 minutes and then 0.2 g of AG-50W-X8 H$^+$ IX resin was added. Within 2 minutes the pH fell to 6. The resin was removed by filtration through a coarse glass frit and the filtrate was sterile filtered. The pH of the filtrate was raised to 7.1 with fresh 2N NaOH and 1.3 mL of a 19,000 ppm Pt solution (0.126 mmol) of cis-diamminediaquaplatinum(II) dinitrate was added. This was stirred for 35 minutes and then purified by centrifugal ultrafiltration. After concentrating to 18 ml and washing three times with 15 mL water, the retentate was lyophilized to give 182 mg of a white solid whose $^{195}$Pt NMR spectrum showed two peaks: −1595 and −1732 ppm in about 1:4 ratio. The major peak at −1732 is the O,O'—Pt chelate of cisdiammineplatinum(II).

B. Preparation of poly(glutamate)-Ama=Pt(NH$_3$)$_2$ N,O—Pt chelate

The above poly(glutamate)-Ama=Pt(NH$_3$)$_2$, O,O'—Pt chelate was subjected to the O,O'—Pt to N,O—Pt chelate conversion conditions of Example 4: 110 mM NaCl, 85 mM phosphate, pH=7.4. After about 22 hours at 38° C., it was purified by centrifugal ultrafiltration and the retentate lyophilized to give 163 mg of a white solid that contained 15.5% Pt (0.77 mmol Pt/g polymer), 0.035% P; $^{13}$C NMR (93/3H$_2$O/D$_2$O) δ 186.9, 183.6, 182.8, 182.1 (p-glu), 180.0, 175.3, 174.2 (p-glu), 173.6, 172.5, 171.0, 170.7, 155.7, 72.1, 63.6, 62.7, 60.4, 25.4, 54.2 (p-glu), 53.5, 51.6, 34.2 (p-glu), 32.1, 31.4, 30.8, 28.6 (p-glu), 26.0, 25.5, 25.0; $^{195}$Pt NMR (93/3H$_2$O/D$_2$O) δ 1595 (v br s, 22%, (NH$_3$)$_2$Pt(RCO$_2$) and RCO$_2$, H$_2$O and/or OH) and −2053 (br s, 78%, N,O—Pt chelate of amidomalonate).

Example 9

Preparation of poly(glu-Ama-diEt)

To a bottle containing 0.5 g (3.29 mmol of —CO$_2$Na groups) of polyglutamate and a stir bar, 1.39 g (6.58 mmol) diethylaminomalonate HCl salt, 1.89 g (9.862 mmol) EDC, 0.503 g (3.287 mmol) HOBt, and 20–25 mL dry DMF (HPLC grade, >48 h over 4A sieves) was added in a dry box and stirred to give a cloudy mixture. After stirring overnight at ambient temperature the mixture was poured into 150 mL water to give a white precipitate. The material was suspended in water, filtered and washed with water. After drying in vacuo for 3 days, 0.79 g of solid was obtained: $^1$H NMR (CDCl$_3$) δ 8.25 (v br s, 1, NH-glu), 7.24 (br s, I, NH-Ama), 5.16 (d, 1, J=5.7, CH-Ama), 4.22 and 4.1 (m and br s, OCH$_2$CH$_3$ and CH-gly) 2.65, 2.33, and 2.18 (br s, 4, CH$_2$CH$_2$-glu), and 1.26 (br t, 6, OCH$_2$CH$_3$); $^{13}$C NMR (CDCl$_3$) 6175.9, 171.9, 166.5, 62.4, 56.8, 56.4, 32.5, 26.3, and 13.9 Without further purification, this material was used in Example 10.

Example 10

Preparation of poly(glu-Ama)=Pt(NH$_3$)$_2$, O,O'—Pt and N,O—Pt chelates

About 30 mL of an EtOH slurry of 0.79 g (2.75 mmol Ama-diEt groups) of poly(glu-AmadiEt) was made 40 mM in NaOH. The pH was held at 12.3–12.6 and the mixture was warmed and sonicated for 30 minutes to give a slightly hazy solution. The pH was reduced to 7.26 with 1.8 g of H$^+$ IX resin and sterile filtered to give a faint yellow solution. The volume was reduced to about 30 mL in vacuo and 4.2 mL of a 18,400 ppm Pt (0.39 mmol) solution of cis-diamminediaqua-platinum(II) dinitrate was added to give a solution with a pH of 5.97. The pH was reduced to 5.0 with 5% HNO$_3$ and stirred for 1 hour at ambient temperature.

After stirring for 1 hour, a sample of the above reaction mixture was lyophilized to give 90 mg of a white solid, the $^1$H NMR spectrum of which indicated that only 67% of the ethyl esters were hydrolyzed: 10.3% Pt; $^1$H NMR (D$_2$O) δ 5.93 (s, 0.1 exchanged, CH-ama), 4.4–4.1 (m, 3.4, CH-glu, OCH$_2$CH$_3$, and NH$_3$ (?)), 2.46 (br s, 2, CH$_2$CH$_2$), 2.07 (br s, 2, CH$_2$CH$_2$), and 1.25 (br q, 2, OCH$_2$CH$_3$); $^{13}$C NMR (H$_2$O/D$_2$O 93/7) 6175.1, 175.0, 174.8, 174.5, 173.8, 171.1, 171.0, 170.8, 170.5, 63.6, 60.7, 60.4, 60.0, 53.7, 31.9, 27.8, and 14.0; $^{195}$Pt NMR (H$_2$O/D$_2$O 93/7) δ –1734 (O,O'—Pt, 86%) and –2034 (N,O—Pt, 14%).

The remaining 32 mL of poly(glu-Ama)=Pt(NH$_3$)$_2$, O,O'—Pt chelate solution was made 110 mM in NaCl and 85 mM in phosphate by the addition of 207 mg NaCl, 76 mg NaH$_2$PO$_4$.H$_2$O and 588 mg Na$_2$HPO$_4$.7H$_2$O. The pH was adjusted to 7.4, the solution was sterile filtered and then incubated at 42° C. for 16 hours. The solution was slightly hazy at this point. It was re-filtered and then purified by centrifugal ultrafiltration. The retentates were lyophilized to give about 600 mg of a light yellow solid: 11.4% Pt; $^1$H NMR (D$_2$O) δ 5.2 (br s, 0.1 exchanged, CH-ama), 4.59 (br s, 0.2), 4.4–4.1 (m, 2.5, CH-glu, and OCH$_2$CH$_3$), 4.00 and 3.85 (br s, 0.25), 2.47 (br s, 2, CH$_2$CH$_2$), 2.06 (br s, 2, CH$_2$CH2), and 1.25 (br q, 2, OCH$_2$CH$_3$); $^{13}$C NMR (H$_2$O/ D$_2$O 93/7) δ 175.1, 174.8, 174.4, 173.7, 171.0, 170.8, 170.5, 63.5, 63.1, 62.7, 53.7, 32.2, 31.8, 27.9, 14.0; $^{195}$Pt NMR (H$_2$O/D$_2$O 93/7) δ–1730 (O,O'—Pt, 8%) and –2053 (N,O—Pt, 92%).

Example 11

Preparation of Ac-Ama=Pt(NH$_3$)$_2$O,O'—Pt and N,O—Pt chelates

In a 20 mL vial, 800 mg (3.68 mmol) N-acetamidomalonate was stirred with 8 mL water, and 2.0 mL 2N NaOH. Within 3 minutes a faint yellow solution at pH 12.6 was obtained. After 30 minutes, H$^+$ IX resin was added, and the pH dropped to 7.0. The resin was removed by filtration, the pH was raised to 7.5 and 2.53 mL of a 28,375 ppm Pt (3.68 mmol) solution of cis-diamminediaqua-platinum(II) dinitrate was added. The pH dropped to 4.4. Upon addition of 2 drops of 2N NaOH a white solid formed. The mixture was filtered and a sample was made 10% in D$_2$O and analyzed by $^{195}$Pt NMR. Only a peak at –1734 was apparent.

The filtrate was made 100 mM in KI and 50 mM in KHCO$_3$ (pH 7.7–7.9) and sterile filtered. It was warmed to 40° C. and held for 18 hours. An orange precipitate which formed was removed by filtration and the filtrate was stripped in vacuo. The residue was stirred with 20 mL of acetone for 1 hour. A portion was filtered, made 7% in D$_2$O and analyzed by $^{195}$Pt NMR spectroscopy. Only one peak at –2057 ppm, the N,O-AC-Ama-Pt(NH$_3$)$_2$ was apparent.

Example 12

Preparation of poly(HPMA)-GFLG-Ama-diEt, 45 kDa and 350 kDa

A. Preparation of MA-GFLG-Ama-diEt

About 25 g of MA-GFLG-ONp was treated with 1.2 equivalents diethylaminomalonate HCl salt, 3 equivalents TEA and 1 equivalent HOBt in DMF at 50° C. for about 16 hours. The DMF was removed in vacuo, and the residue slurried in diethyl ether and cooled to 4° C. overnight. The product was collected by filtration, washed with ether, and dried in vacuo to give MA-GFLG-Ama-diEt, the identity and purity of which was confirmed by $^1$H NMR spectroscopy and HPLC: $^1$H NMR (DMSO-d$_6$) δ 8.74 (d, 1, J=7.3, NH-Ama), 8.14 (t, 1, J=5.9, CH$_2$-gly), 8.11 (d, I, J=8.2, α-CH leu), 8.03 (t, 1, J=8.2, CH$_2$ gly), 8.01 (d, 1, J=8.2, NH-phe), 7.3–7.0 (m, 5, ArH), 5.70 (s, 1, —CH$_2$), 5.37 (t, 1, J=1.6, CH$_2$), 5.09 (d, 1, J=7.3, CH-Ama-diEt), 4.53 (m, 1, αCH of phe), 4.32 (m, 4, OCH$_2$CH$_3$), 3.9–3.7 (m, 3, CH$_2$-gly). 3.63 and 3.59 (dd, 1, J=16, 3, 5.8), 3.1–3.0 and 2.83–2.73 (m, 2, CH$_2$-phe), 2.51, (m, 3, J=1.7, CH$_3$CH$_2$), 1.59 (m, 1, J=6.5, CH$_2$CH(CH$_3$)$_2$), 1.49 (t, 2, J=7.5, CH$_2$CH (CH$_3$)$_2$), 1.216 and 1.214 (two t, 6, J=7.2, OCH$_2$CH$_3$), 0.88 (d, 3, 11=6.6, CH$_2$CH(CH$_3$)$_2$), and 0.84 (d, 3, J=6.5, CH$_2$CH (CH$_3$)$_2$).

B. Preparation of poly(HPMA)-GFLG-Ama-diEt, about 45 kD.

A flask with condenser was charged with 12.7 wt % HPMA and MA-GFLG-Ama-diEt monomers in a 90/10 ratio, 0.6 wt % pure AIBN, p-nitrophenol (10 mol % of total monomers), and 86 wt % acetone. The mixture was degassed for approximately 30 minutes with nitrogen and then heated at 50° C. for 65 hours. The poly(HPMA)-GFLG-Ama-diEt was collected by filtration and washed with ether. It was re-dissolved in absolute EtOH at about 25% wt/vol and then precipitated with 8 volumes of EtOAc. The resulting solid was collected by filtration, washed with ether and dried in vacuo to give about 20 g of off-white powder. Its $^1$H NMR spectrum was very similar to that of the 25 kDa compound: Mw=44.5 kDa, PDI=1.76, bimodal. Amino acid analysis: (μmol/mg polymer) 2.7:8.1:0.9:0.9 of gly: 2-hydroxypropylamine: leu:phe; MALDI-TOF-MS (NBA matrix) m/z M$^+$ 40–45 kDa, M$^{+2}$ 14–16 kDa.

C. Preparation of poly(HPMA)-GFLG-Ama-diEt, about 350 kD.

The procedure used for the 45 kD poly(HPMA)-GFLG-Ama-diEt was repeated except that p-nitrophenol was omitted. About 25 g of a white powder was obtained. Its $^1$H NMR spectrum was very similar to that of the 25 kDa compound thought the peaks were broader: Mw=351 kDa, PDI=3.95, trimodal.

Example 13

Preparation of poly(HPMA)-GFLG-Ama=Pt(NH$_3$)$_2$, N,O—Pt chelate 45 kDa

To a 250 media bottle containing a stir bar, 72 mL water and 15.5 g (6.82 mmol Ama-diEt groups) poly(HPMA)-GFLG-Ama-diEt were added. Once vigorous stirring was established, 48 mL of additional water was added and the mixture was stirred for about 1 hour to give a pale violet solution. To this solution 12 mL of fresh 2 M NaOH was added, which raised the pH to 12.6. The pH was maintained at 12.4–12.8 for 30 minutes and then 15.4 g of mixed bed IX resin (AG 501-X8(D) H$^+$, OH$^-$ forms) was added. The pH dropped to 5.0 after 3 minutes, after which the resin was removed by filtration through a sterile Steritop 1.50 mL filter. The pH of the filtrate was raised to 7.60 with fresh 2N NaOH, and 8.14 mmol (64 mL, 24,200 ppm Pt) of freshly prepared cis-diammineplatinum(II) solution was added in one portion. After the addition, the pH was 5.1. The mixture was then stirred overnight. The next day the pH was 4.42. and 5.10 g Chelex 100 resin was added. The pH rose to 5.33 and the mixture was stirred for 90 minutes. The resin was removed by filtration through a coarse glass frit to give 460 mL of solution. The filtrate was made 110 mM in NaCl and 80 mM in phosphate with 2.96 g NaCl, 1.08 g NaH$_2$PO$_4$.H$_2$O, and 7.66 g Na$_2$HPO$_4$.7H$_2$O. The pH was adjusted to 7.4 with 2N NaOH and 5% HNO$_3$ and then sterile filtered through a Steritop filter into a sterilized media bottle which was capped with a membrane cap in a biological safety hood. This was placed in a 39° C. water bath for 20 minutes and then in a 37–38° C. incubator oven for 22 hours.

After 22 hours at 37–38° C., the solution was purified by TFF. The solution was concentrated to 5% wt/vol, 7 volumes of permeate were collected, then the retentate was concentrated to 8–10%. The retentate was sterile filtered through a Millipak 20 filter into a sterilized lyophilization flask. After lyophilization, 11.2 g of off-white solid was obtained: 8.89% Pt, 5.4% H$_2$O, 1.03% Na, 0.05% Cl, <0.05% P; $^1$H NMR (D$_2$O) δ 67.4 and 7.3 (br s,5, ArH), 5.23 (br s, partially exchanged, CH of Ama), 4.66 (br s, 1, α-H-phe), 4.37 (br s,1, α-H-leu), 4.05 (sh, NH$_3$ or CH$_2$ of gly), 4.1–3.8 (tall s and short m, ~13, —NHCH$_2$CH(OH)CH$_3$, —NHCH$_2$CO$_2^-$) 3.35–2.9 (m, 18, —NHCH$_2$CH(OH)CH$_3$ and phe-CH$_2$), 2.25–1.2 (m, —CH$_2$— of polymer backbone, CH$_2$ and CH of leu), 1.20 and 1.19 (s, ~27, —NHCH$_2$CH(OH)CH$_3$), 0.99 (s, CH$_3$— of polymer backbone), 0.93 and 0.87 (sh and s, 6, leu-CH$_3$); $^{13}$C NMR (H$_2$O/D$_2$O 93/7) δ 186.7, 71.0, and all other peaks as reported for Example 4; $^{195}$Pt NMR (H$_2$O/D$_2$O 93/7) δ–2055 (100%).

Example 14

Preparation of poly(HPMA)-GFLG-Ama=Pt(NH$_3$)$_2$, N,O—Pt chelate, >351 kDa

To a 500 mL media bottle equipped with a stir bar, 120 mL water and 20 g (8.80 mmol Ama-diEt) poly(HPMA)-GFLG-Ama-diEt (351 kDa) were added. Once vigorous stirring was established, 100 mL water was added and the mixture was stirred for 2 hours to give a colorless solution. A pH electrode was inserted and 14 mL of fresh 2 N NaOH was added. The pH rose to 12.74 and was held between 12.4–12.8 for 30 minutes. Afterwards, 19.9 g of mixed bed (H$^+$, OH$^-$ forms) IX resin (AG 501-X8(D) was added and within 3 minutes the pH fell to 6. The mixture was sterile filtered through a Steritop bottle-top filter and its pH was adjusted to 7.63 with 2N NaOH and 5% HNO$_3$. In one portion, 85.5 mL of a 24,200 ppm Pt solution (10.6 mmol) of freshly prepared cis-diamminediaqua-platinum(II) dinitrate solution was added to give a solution with a pH of 5.02. The mixture, which was slightly cloudy due to the size of the particles, was stirred overnight at ambient temperature. During this time the pH fell to 4.25 and 6.77 g Chelex 100 resin was added. The pH rose to 5.33 and after stirring for 90 minutes 0.2 g of filter aid pulp was added. The mixture was sterile filtered through a coarse glass frit. The solution, 725 mL, was made 110 mM in NaCl and 85 mM in phosphate by addition of 4.661 g (79.8 mmol) NaCl, 12.24 g (45.7 mmol) Na$_2$HPO$_4$.12H$_2$O and 1.703 g (10.1 mmol) NaH$_2$PO$_4$.H$_2$O. The pH was adjusted to 7.4 and the mixture was passed through a Steritop filter into a 1 L media bottle. The bottle was sealed with a membrane cap and placed in a water bath at 40° C. for 20 minutes and then in an incubator oven at 37–38° C. After about 22 hours, the contents were purified by TFF. NMR spectra were obtained using about 50 mg of material because the more concentrated solution was too viscous. Lyophilization of the retentate gave 19.9 g of white solid: 7.95% Pt, 7.0% H$_2$O, 1.03% Na, 0.09% Cl, <0.05% P; $^1$H NMR (D$_2$O) δ 7.4 and 7.3 (br s, 5, ArH), 5.23 (br s, partially exchanged, CH of Ama), 4.65 (br s, 1, α-H-phe), 4.38 (br s,1, α-H-leu), 4.05 (sh, NH$_3$ or CH$_2$ of gly), 4.1–3.8 (tall s and short m, ~13, —NHCH$_2$CH(OH)CH$_3$, —NHCH$_2$CO$_2^-$) 3.35–2.9 (m, 18, —NHCH$_2$CH(OH)CH$_3$ and phe-CH$_2$), 2.25–1.2 (m, —CH$_2$— of polymer backbone, CH$_2$ and CH of leu), 1.20 and 1.19 (s, ~27, —NHCH$_2$CH(OH)CH$_3$), 0.99 (s, CH$_3$— of polymer backbone), 0.93 and 0.87 (sh and s,6, leu-CH$_3$); $^{13}$C NMR (H$_2$O/D$_2$O 93/7) δ 186.7, 71.0, and all other peaks as reported for Example 4; $^{195}$Pt NMR (H$_2$O/D$_2$O 93/7) δ –2055 (100% N,O—); SEC trimodal, Mp=468 kDa, 147 kDa Mn=66.3 kDa, PDI=13.8; Pt release: 0.68% at 3 h, 2.28% at 24 hours.

a. Example 15

Preparation of poly(HPMA)-GG-ONp, 23 kDa

A dry 5 L media bottle covered in aluminum foil and equipped with a tight-fitting 3-valve cap from Omnifit, a sparge tube and a stir bar was charged with HPMA (245.5 g, 1.7146 mol, 11 equiv.), MA-GlyGly-ONp (50.0 g, 0.1556 mol, 1 eq.), and dry HPLC grade acetone (1970 g). The heterogeneous mixture was vigorously stirred and sparged with Argon for 90 minutes to give a cloudy colorless mixture. AIBN (14.2 g, 0.8647 mol recrystallized from CH$_2$Cl$_2$) was dissolved in 75 mL acetone in a 250 mL media bottle. After sparging with Argon for 90 min, this solution was poured into the media bottle while vigorously sparging with Argon. The 250 mL media bottle was rinsed with 30 mL of acetone and the rinse transferred to the reaction vessel. After 90 minutes the sparging was stopped, and the reaction vessel was placed in a 50° C. water bath for 48 hours. Afterwards, the reaction mixture, with a white precipitate on the bottom, was allowed to cool to ambient temperature and the vessel was vented. The reaction mixture was transferred to four 750 mL centrifuge bottles. Each bottle was spun at 2600 RCF (3800 rpm) for 10 minutes at 5° C. The supernatant was decanted, and the process repeated until the polymer had all been collected. The crude polymer precipitate was washed three times with 1–2 bed volumes (approx. 200 mL) of acetone and three times with 1–2 bed volumes (approx. 150 mL) of diethyl ether. For each washing, the solvent was introduced, the bottle shaken for 1 minute and then centrifuged as before. After the final wash the polymer was dried in vacuo to constant weight to yield 228.8 g of poly(HPMA)-GlyGly-ONp: $^1$H NMR (DMSO-$d_6$): δ 8.7 (s-amide NH), 8.3 (d, ONp aromatic H), 7.4 (d-ONp aromatic H), 4.8 (s, $CH_2CHOHCH_3$), 4.3 (s, $CH_2$ of glycine), 3.7 (s, $CH_2CHOHCH_3$), 3 (s, $CH_2CHOHCH_3$), 1.5 (br, m, $CH_2$ of polymer backbone), 1.0 (s, $CH_3$ of polymer backbone), 0.9 (d, $CH_2CHOHCH_3$); 0.433 mmol ONp/g polymer. No small molecules except for <1% each of EtOH and EtOAc.

b. Example 16

Preparation of poly(HPMA)-GG-Ama-diEt

An oven-dried 500 mL media bottle equipped with a stir bar and septum cap was charged with 6.0 g poly(HPMA)-GG-ONp (3.162 mmol of ONp) and 2.673 g (12.6 mmol) diethyl aminomalonate HCl (Ama-diEt HCl). Dry pyridine (87 mL) was cannulated into the flask and the mixture was stirred at 40° C. until a solution was obtained. The extent of the reaction was determined by measuring the free and total HONp until they were equal, then the product was precipitated by addition of 800 mL of dry ethyl acetate and stirred for 1 hour. The mixture was collected by centrifugation at 3840 RCF for 10 min then washed three times with 100 mL of $Et_2O$. The sediment was dissolved in 70 mL of EtOH and gently stirred with 18 g of AG 501-X8(D) IX resin ($H^+$ & $OH^−$ forms) for 1 hour. The resin was filtered and the polymer precipitated and purified by centrifugal sedimentation. After drying in vacuo, 6.25 g of a white powder of poly(HPMA)-GG-Ama-diEt was obtained: $^1$H NMR (DMSO-$d_6$): δ 7.3 (m, amide NH), 5.1 (d, NHC), 4.6 (s, $CH_2CHOHCH_3$), 4.2 (q, NHC), 3.6 (s, $CH_2CHOHCH_3$), 3.1 (s, $CH_2CHOHCH_3$), 1.7 (br.m., $CH_2$ of polymer backbone), 1.2 (q, NHC), 1.1 (s, $CH_3$ of polymer backbone), 0.9 (s, $CH_2CHOHCH_3$), and no small molecules except for <1% each of EtOH and EtOAc.

c. Example 17

Preparation of poly(HPMA)-GG-Ama=Pt($NH_3$) chelates, approx. 22 kDa

A. Hydrolysis of poly(HPMA)-GG-Ama-diEt, approx. 25 kDa

A 50 mL centrifuge tube equipped with a stir bar was charged with 0.5 g p(HPMA)-GG-Ama-diEt (0.2635 mmol Ama residues), and 4.2 mL Milli-Q $H_2O$. After dissolution, 0.347 mL (0.694 mmol NaOH) 2 M NaOH was added and the pH maintained at 12.6 for 90 minutes. The solution was then stirred with 0.71 g Bio-Rex MSZ 501D resin. When the pH fell to 7.84 the resin was removed by filtration. The pH of the filtrate was then adjusted to 7.31 with 2 M NaOH.

B. Preparation of poly(HPMA)-GG-Ama=Pt($NH_3$)$_2$O,O'-Chelate

To the above pH 7.3 solution, 2.40 mL (0.316 mmol Pt) of a 30, 149 ppm solution of cis-diamminediaquaplatinum (II) dinitrate was added. The pH was quickly adjusted to 5.6 with 2 M NaOH. While stirring overnight the pH dropped to 3.31. It was raised to 5.4 and 0.192 g of Chelex resin was added. After gently stirring for 90 minutes, the resin was removed by sterile filtration to give 9 mL of a slightly colored solution of the title compound.

C. Preparation of poly(HPMA)-GG-Ama=Pt($NH_3$)$_2$ N,O Chelate

The above 9 mL of filtrate was made 110 mM in NaCl and 80 mM in phosphate (pH=7.4) with 0.069 g (0.89 mmol) NaCl, 0.019 g (0.142 mmol) $NaH_2PO_4.H_2O$, and 0.153 g (0.57 mmol) $Na_2HPO_4.7H_2O$. The pH was adjusted to 7.4, the solution warmed to 38° C. in a water bath and then transferred to a 38° C. oven for 24 hours. The solution was purified by centrifugal ultrafiltration and lyophilized to yield 0.413 g of the title compound as an off-white solid: 10.5% Pt, 7.31% $H_2O$; % Pt Release at 3 & 24 h, 1.4%, 4.6%. $^{195}$Pt NMR (93:7$H_2O$: $D_2O$): δ −2060 (br s, N,O—Pt chelate). SEC: $M_p$=24.6 kDa, $M_w$=25.4 kDa, $M_n$=17.6 kDa, $M_w/M_n$=1.44.

d. Example 18

Preparation of poly(HPMA)-GG-Ama=Pt=DACH chelates, approx. 24 kDa

A. Hydrolysis of poly(HPMA)-GG-Ama-diEt (~24 kDa) (53b)

A 250 mL media bottle equipped with a stir bar was charged with 5.0 g p(HPMA)-GG-Ama-diEt (2.635 mmol Ama-diEt) and 42 mL Milli-Q $H_2O$. After dissolution, 3.47 mL 2 M NaOH (6.94 mmol NaOH) was added and the pH maintained at 12.6 for 90 minutes. Next, 5 g of Bio-Rex MSZ 501 D resin was added and the mixture gently stirred until the pH fell to 7.41 at which time the resin was removed by filtration. The pH of the filtrate was then adjusted to 7.49 with 2 M NaOH.

B. Preparation of poly(HPMA)-GG-Ama=Pt=DACH O,O' Chelate

To the above pH 7.5 filtrate, 25.9 mL of a 23,808 ppm solution of cis-diaqua-1R,2R-DACH=Pt(II) dinitrate (3.16 mmol Pt) was added. The pH was adjusted to 5.23. After stirring overnight, the pH fell to 4.11. The pH was re-adjusted to 5.4 with 2 M NaOH and 1.92 g of Chelex resin was added after which the mixture gently stirred for 90 minutes and then sterile filtered to give 100 mL of filtrate containing the title compound.

C. Preparation of poly(HPMA)-GG-Ama=Pt=DACH N,O-Chelate

The above filtrate was made 110 mM in NaCl and 80 mM in phosphate by addition of 0.648 g (11 mmol) NaCl, 0.221 g (1.6 mmol) $NaH_2PO_4$—$H_2O$, and 1.71 g (6.4 mmol) $Na_2HPO_4.7H_2O$. The pH was adjusted to 7.4, the mixture was warmed to 38° C. in a $H_2O$ bath and then it was transferred to a 38° C. oven for 24 hours. The solution was subjected to TFF purification and lyophilized to yield 4.31 g of an off-white solid: 9.7% Pt, 7.62% $H_2O$; % Pt Release at 3 & 24 hours, 1.3%, 5.5%; $^1$H NMR ($D_2O$): δ 6.3 (s, amide protons) 4.8 (s, HOD), 4.2 (s), 4.0 (s), 3.2 (d, $CH_2$ of HPMA side chain), 1.8 (d, $CH_2$ of polymer backbone), 1.2 (s, $CH_3$ of HPMA side chain), 0.9 (s, $CH_3$ of polymer backbone); $^{195}$Pt NMR (93:7$H_2O$: $D_2O$): δ −2269 and −2295 (N,O-chelate, >93%), −2590 (N,N-chelate, <7% of all chelates); SEC $M_p$=24.1 kDa, $M_w$=24.4 kDa, $M_n$=15.7 kDa, $M_w/M_n$=1.56.

e. Example 19

Preparation of poly(HPMA)-GGG-Ama-diEt

A. Preparation of Gly-Ama-diEt, TFA Salt

A mixture of $NaHCO_3$ (324.98 g, 3.87 mol) and 1.5 L of water was added slowly to diethylaminomalonate HCl (740.78 g, 3.50 mol) in a 4 L Erlenmeyer flask. $CH_2Cl_2$ (1

L) was added and the resulting two-phase mixture vigorously stirred for 15 minutes. The $CH_2Cl_2$ layer was collected, 0.5 L $CH_2Cl_2$ was added to the aqueous layer, the mixture was stirred for 15 minutes and the $CH_2Cl_2$ layer collected. The pH of the aqueous layer was 7.8. The $CH_2Cl_2$ layers were combined, dried over anhydrous $Na_2SO_4$ and filtered. The $CH_2Cl_2$ was removed in vacuo until the volume was reduced to about 0.6 L. This solution was placed into a 2 L, 3-neck round-bottom flask, and t-BOC-Gly-OH (569.34 g, 3.25 mol) was added. The mixture was stirred and cooled to 10° C. DCC (670.57 g, 3.25 mol) dissolved in 400 mL $CH_2Cl_2$ was added over 2.5 hours to the vigorously stirred diethylaminomalonate/t-BOC-Gly-Ame mixture with the temperature being maintained below 25° C. After addition of the DCC was complete, the mixture was stirred for 45 minutes in a ice bath to lower the temperature to approx. 5° C. The cooling bath was removed, the reaction mixture was stirred for an additional 4 hrs at ambient temperature and then it was allowed to sit overnight. The white precipitate that formed was removed by filtration and washed with 100 mL of $CH_2Cl_2$. The filtrate and $CH_2Cl_2$ wash were combined and the solvent was removed in vacuo to give a yellow crystalline material, which after drying under vacuum gave 881.8 g of t-BOC-Gly-Ama-diEt: $^1$H NMR ($CDCl_3$): δ 7.44 (d, 1H, NH), 5.69 (t, 1H, NH), 5.19 (d, 1H, CH), 4.27 (m, 4H, $CH_2$), 3.90 (d, 2H, $CH_2$), 1.46 (s, 9H, $CH_3$), 1.29 (t, 6H, $CH_3$).

To a solution of t-BOC-Gly-Ama-diEt (985.2 g, 2.96 mol) in 770 mL $CH_2Cl_2$, 770 mL trifluoroacetic acid (TFA) was added. The resulting mixture was stirred and after 6 hour a precipitate formed, which was collected after 8 hours. Recrystallization from $CHCl_3$ gave 1025.1 g of TFA-Gly-Ama-diEt as a white solid: $^1$H NMR (DMSO-$d_6$): δ 9.34 (d, 1H, NH), 8.13 (b.s., 3H, $NH_2$ TFA salt), 5.17 (d, 1H, CH), 4.20 (m, 4H, $CH_2$), 3.71 (d, 2H, $CH_2$), 1.22 (t, 6H, $CH_3$).

B. Preparation of poly(HPMA)-GGG-Ama-diEt, approx. 23 kD

An oven-dried 5 L media bottle equipped with a septum cap, a stir bar, and Argon inlet was charged with TFA-Gly-Ame (104.28 g, 0.3012 mol), pyridine (2.1516 kg) and TEA (45.01 g, 0.4448 mol). Once a solution was obtained, poly(HPMA)-GlyGly-ONp (225 g, 0.10316 mol ONp) was added in 4–5 portions over 30 minutes. After 2.5 hours, when all or nearly all the polymer had dissolved, an aliquot was taken for determination of percent free and total HONp. During the analyses the reaction continued to stir. When analysis indicated that the reaction was 100% complete (3.5 to 4 hours at ambient temperature), the reaction vessel was capped, heated to 40° C. and held there for 2 hours. Five 500–550 mL portions of the clear yellow reaction mixture were transferred into five 5 L media bottles each containing a magnetic stir bar. With vigorous stirring, the crude product was precipitated from each 5 L media bottle by steady addition of six 580 mL portions of EtOAc/diethyl ether (500 mL/80 mL). The cloudy yellow mixture was stirred for 1 hour, the precipitate was collected by centrifugation and washed once with 1–2 bed volumes of EtOAc and twice with 1–2 bed volumes of diethyl ether. The product was dried in vacuo and then added slowly to approx. 2 L of vigorously stirred EtOH (10–15% wt/vol) in a 5 L media bottle. Upon dissolution, 1008 g of Bio-Rex MSZ 501 D indicating IX resin (EtOH washed) was added. The mixture was gently stirred for 2.5 hours then examined every 30 minutes to see if any of the indicating blue beads remained. If no blue beads were apparent, 150–200 g more of the IX resin was added. When blue beads remained after 30 minutes, the resin was removed by filtration through a Whatman GF/B glass microfiber filter. The polymer from the EtOH solution was precipitated, collected, washed as above and then dried in vacuo for approx. 72 hours to give 204.14 g of poly (HPMA)-GlyGlyGly-Ame as a fine yellow powder. SEC (MeOH/$H_2O$) $M_p$=24 kDa, $M_w$=24 kDa, $M_n$=15 kDa, PDI=1.6; $^1$H NMR (300 MHz, DMSO-$d_6$) δ 0.83 (br s, 6, $RCH_2C(CH_3)R$), 1.04 (br d, 3, $RCH(OH)CH_3$), 1.22, (br t, 3, $RC(O)OCH_2CH_3$), 1.40–2.30 $RCH_2C(CH_3)C(O)R$ (2 br s, 4, $RCH_2C(CH_3)C(O)R$), 2.93 (br s, 2, $RNHCH_2CH(OH)CH_3$), 3.69 $RNHCH_2CH(OH)CH_3$ (br s, 1, $RNHCH_2CH(OH)CH_3$), 3.86 (br s, 6, $RNHCH_2C(O)R$), 4.05–4.30 (br m, 4, $ROCH_2CH_3$), 4.71 $RCH(OH)CH_3$, (br s, 1, $RCH(OH)CH_3$), 5.08 (d, 2, $RNHCH(C(O))_2$), 6.60–7.70, (br m, 1, $RNHCH_2CH(OH)CH_3$), 7.98–8.47 (br m, 3, linker NH), and 8.83 (br, 1 $RNHCH(C(O))_2$).

f. Example 20

Preparation of poly(HPMA)-GGGG-Ama-diEt, 22 kDa

A. Preparation of t-BOC-GlyGly-OH

An oven-dried 20 mL vial equipped with septum and stir bar was charged with 6 mL dioxane, Gly—Gly (1.325 g, 10.0 mmol), BOC—ON (2.714 g, 11.0 mmol), and $Et_3N$ (2.10 mL, 15 mmol). The mixture was stirred for 2 hours during which time a clear yellow solution formed. The mixture was extracted with EtOAc (20 mL) and $H_2O$ (15 mL). The aqueous layer was collected, washed with EtOAc and added to 50 mL 5% citric acid. The t-BOC-GlyGlyOH was extracted with EtOAc (200 ml) and dried over anhydrous $Na_2SO_4$. The EtOAc was removed in vacuo and triturated with hot $Et_2O$. White crystals were collected, washed with $Et_2O$ and dried to give 1.309 g of the title compound: $^1$H NMR (300 MHz, DMSO-$d_6$): δ 12.3 (bs 1H, $CO_2H$), 8.04 (t, 1, NH), 6.98 (t, 1H, NH), 3.75 (d, 2H, $CH_2$), 3.56 (d, 2H, $CH_2$), and 1.38 (s, 9H, $C(CH_3)_3$).

B. Preparation of t-BOC-GlyGly-Ama-diEt

A 100 mL media bottle was charged with t-BOC-GlyGly-OH (10.02 g, 43.15 mmol), diethylaminomalonate HCl (9.13 g, 43.15 mmol), EDC (12.66 g, 66.04 mmol), HOBt (0.66 g, 4.315 mmol), and 200 mL pyridine. After stirring at ambient temperature for 21 hours, the pyridine was removed in vacuo and the residue was extracted with 3×300 mL $CHCl_3$. The $CHCl_3$ layer was dried over anhydrous $MgSO_4$, the $CH_2Cl_2$ removed in vacuo and the residue recrystallized from hexane:ether (7:3) at 4° C. The t-BOC-GlyGly-Ama-diEt was collected as 12.32 g of white crystals: $^1$H NMR ($CDCl_3$) δ 7.07 (br d, 1, J=6.7 Hz, $NHCH$), 6.85 (br t, 1, $NHCH_2$), 5.21 (br t, 1,$NHCH_2$), 5.15 (d, 1, J=6.7 Hz, CH-Ama-diEt), 4.22–4.33 (m, 4H, $OCH_2CH_3$), 4.08 (br d, 2,$CH_2$-Gly), 3.86 (br d, 2, $CH_2$-Gly), 1.45 (tall s, 9,t-butyl), 1.31 (t, 6, $OCH2CH_3$).

C. Preparation of TFA-GlyGly-Ama-diEt Salt

A 100 mL media bottle equipped with a septum cap and stir bar was charged with of t-BOC-GlyGly-Ama-diEt (5.12 g, 13.14 mmol) and $CH_2Cl_2$(15 mL). With vigorous stirring, TFA (25 mL in 25 mL $CH_2Cl_2$) was added dropwise. After 1 hour the reaction was complete, the TFA was removed in vacuo and the trifluoroacetate salt precipitated with $Et_2O$. The TFA-GlyGly-Ama-diEt salt was collected by filteration, washed with $Et_2O$ and recrystallized from absolute EtOH: ether (7:3 v/v). The white crystals were dried in vacuo to give 5.21 g of product: $^1$H NMR (DMSO-$d_6$) δ 8.96 (br d, 1, —NHCH—), 8.63 (br t, 1, —$NHCH_2$—), 8.02 (v br s, 3, $NH_3CH_2$), 5.09 (d, 1, $CH(CO_2Et)$, 4.12–4.24 (m, 4, $OCH_2CH_3$), 3.94 (br d, 2, —$NHCH_2$—), 3.59 (br s, 2, —NHCH$_2$—), 1.21 (t, 6, OCH$_2$CH$_3$). $^{13}$C NMR (CDCl$_3$) δ 168.8, 166.4, 158.3, 158.0, 119.3, 115.4, 61.9, 56.3, 41.5, 13.9.

D. Preparation of poly(HPMA)-GGGG-Ama-diEt, approx. 22 kDa

An oven-dried 250-mL round bottomed flask equipped with stir bar and septum was charged with 5.724 g (14.19 mmol) of TFA GG-Ama-diEt and the mixture was purged with N$_2$. Then, 70 mL dry pyridine was added and upon dissolution 7.015 g poly(HPMA)-GG-ONp was added in three portions, each portion being added after dissolution of the previous one. The mixture was warmed to 40° C. and the extent of reaction monitored by HPLC. After 23 hours the reaction was complete. Next, 700 mL of dry EtOAc and 100 mL of dry Et$_2$O were added at ambient temperature and the mixture was stirred for 1 hour to precipitate the polymer. The precipitate was collected by centrifugation. The resulting sediment was dissolved in 60 mL absolute EtOH and stirred with 22.0 g of AG 501-X8 (D) IX resin (H$^+$ & OH$^-$ forms) for 2.5 hours. The resin was removed by filtration and the polymer precipitated with 800 mL of EtOAc. After stirring for 1 hour, the precipitate was isolated by centrifugation, washed successively with EtOAc and ether and dried in vacuo to give 5.77 g of the title compound as an off-white powder: $^1$H NMR (DMSO-d$_6$): δ 4.30 (br m, 4, —OCH$_2$CH$_3$), 4.15 (EtOAc), 4.05–3.95 (m, 8, linker CH$_2$), 3.89 (s, 1, —CH$_2$CHOHCH$_3$), 3.65 (EtOH), 3.20 (br d, 2, —CH$_2$CHOHCH$_3$), 2.09 (EtOAc), 2.00–1.60 9br m, polymer backbone CH$_2$), 1.60–1.20 (m, 6, OCH$_2$CH$_3$), 1.19 (br m, 3, —CH$_2$CHOHCH$_3$), 1.00 (br s, polymer backbone CH$_3$).

g. Example 21

Preparation of poly(HPMA)-GGGG-Ama=Pt=1R,2R-DACH, Approx. 22 kDa

A. Hydrolysis of poly(HPMA)-GGGG-Ama-diEt

A 250 mL bottle containing a stir bar, 5.5 g (2.895 mmol Ama residues) poly(HPMA)-GGGG-Ama-diEt and 46 mL Milli-Q H$_2$O was stirred until dissolved. The pH was raised to 12.6 with 3.81 mL (7.62 mmol) 2M NaOH and held there for 90 minutes. The mixture was adjusted to pH 7.51 with 5.5 g of Bio-Rex MSZ 501D resin after which the resin was removed by filtration. The pH of the filtrate was adjusted to 6.93 with 2M NaOH to give a solution of poly(HPMA)-GGGG-Ama(CO$_2$Na)$_2$.

B. Preparation of poly(HPMA)-GGGG-Ama=Pt=1R,2R-DACH O,O'-Chelate

To the above solution of poly(HPMA)-GGGG-Ama (CO$_2$Na)$_2$ was added 27.5 mL (3.47 mmol Pt) of a solution of cis-diaqua-1R,2R-DACH=Pt(II) dinitrate. The pH, which fell to 4.41, was adjusted to 5.14 with 2 M NaOH. While stirring overnight, the pH fell to 2.44. The pH was readjusted to 5.4 with 2 N NaOH, 2.114 g of Chelex 100 resin was added and the mixture gently stirred. After 90 minutes, the resin was removed by sterile filtration to give 100 mL of filtrate.

C. Preparation of poly(HPMA)-GGGG-Ama=Pt=1R,2R-DACH N,O-Chelate

The above 100 mL of filtrate was made 110 mM in NaCl and 80 mM in phosphate with 0.648 g (11 mmol) NaCl, 0.221 g (1.6 mmol) NaH$_2$PO$_4$.H$_2$O and 1.71 g (6.4 mmol) Na$_2$HPO$_4$.7H$_2$O and the pH adjusted to 7.4 with 2 M NaOH. The solution was warmed to 38° C. in a H$_2$O bath and transferred to a 38° C. oven for 24 hours. The solution was purified by TFF and lyophilized to yield 4.31 g of an off-white solid: 8.86% Pt, 9.35% H$_2$O; % Pt Release at 3 & 24 hours, 0.972%, 3.173%; $^{195}$Pt NMR (93:7H$_2$O: D$_2$O): δ −2270 and −2295 (N,O-chelates). SEC (MeOH/H$_2$O) M$_w$ 19.3 kDa, M$_n$=10.1.

h. Example 22

Preparation of 3-aminopropylsulfonamidomalonate, diethyl ester, HCl Salt

A. 3-Chloropropanesulfonamidomalonate diethyl ester (Cl(CH$_2$)$_3$SO$_2$Ama-diEt)

To a solution of diethylaminomalonate HCl (Ama-diEt HCl, 24.34 g, 0.115 mol) in 400 mL of CHCl$_3$ and Et$_3$N (50 mL), 3-chloropropanesulfonyl chloride (21.25 g, 0.12 mol) in 100 mL of CHCl$_3$ was added in a steady stream in an inert atmosphere. The resulting mixture was refluxed for 3 hours, allowed to cool to ambient temperature, and extracted with 1 N HCl (2×300 mL) and with water (2×300 mL). The organic phase was collected, dried over anhydrous Na$_2$SO$_4$ and the CHCl$_3$ removed in vacuo to give 29.05 g of Cl—(CH$_2$)$_3$—SO$_2$-Ama-diEt: $^1$H NMR (CDCl$_3$): δ 1.31 (t, 6, OCH$_2$CH$_3$), 2.33 (m, 2, CH$_2$), 3.28 (t, 2, CH$_2$), 3.68 (t, 2, CH$_2$), 4.26 (m, 4, OCH$_2$CH$_3$), 4.84 (d, 1, CH), 5.59 (d, 1, NH). $^{13}$C NMR (CDCl$_3$) δ 13.6, 26.3, 42.5, 51.2, 58.5, 62.7, 165.9.

B. 3-Iodopropanesulfonamidomalonate diethyl ester

To a solution of NaI (34.47 g, 0.23 mol) in 400 mL of acetone was added Cl—(CH$_2$)$_3$—SO$_2$-Ama-diEt (29.05 g, 0.092 mol). The reaction mixture was refluxed for 6 hours, then cooled to ambient temperature. NaCl was removed by filtration, the filtrate was stripped in vacuo and the residue was dissolved in 300 mL of CH$_2$Cl$_2$. This solution was washed with aqueous Na$_2$S$_2$O$_3$ (3×250 mL) and water (3×250 mL). The organic layer was dried over anhydrous Na$_2$SO$_4$ and the solvent was removed in vacuo to give 29.07 g of the title compound: $^1$H NMR (CDCl$_3$) δ 1.31 (t, 6, OCH$_2$CH$_3$), 2.36 (m, 2, CH$_2$), 3.24 (t, 2, CH$_2$), 3.31 (t, 2, CH$_2$), 4.26 (m, 4, OCH$_2$CH$_3$), 4.85 (d, 1, CH), 5.98 (d, 1, NH). $^{13}$C NMR (CDCl$_3$) δ 3.00, 13.7, 27.1, 54.5, 58.6, 62.7, 165.9.

C. Preparation of 3-Azidopropanesulfonamidomalonate diethyl ester N$_3$—(CH$_2$)$_3$—SO$_2$-AmadiEt Method A: (Caution: NaN$_3$ may react with halogenated solvents to form alkyl diazides which may explode if isolated). To a solution of 3-iodopropane-sulfonylamidomalonate diethyl ester (29.00 g, 0.071 mol) in 300 mL of CCl$_4$, a solution of NaN$_3$ (11.38 g, 0.175 mol) in 50 mL of water containing 10 mol % trioctylmethyl-ammonium chloride were added. The resulting mixture was stirred at 80° C. for 16 hours. The reaction mixture was allowed to cool to ambient temperature. The aqueous layer was separated and washed with dichloromethane (100 mL). The organic layers were combined and washed with water (3×100 mL), then dried over anhydrous Na$_2$SO$_4$. The solvent was removed in vacuo to give 18.94 g of the title compound.

Method B: to a solution of 3-chloropropanesulfonylaminomalonate diethyl ester (44.21 g, 0.14 mol) in 200 mL of DMF was added NaN$_3$ (29.25 g, 0.45 mol). The reaction mixture was stirred at 90° C. for 16 hours and then cooled to ambient temperature. The mixture was poured into ice water and extracted with dichloromethane. The combined organic layers were washed with brine and dried over anhydrous Na$_2$SO$_4$. The solvent was removed in vacuo to give 28.02 g of the title compound: $^1$H NMR (CDCl$_3$): δ 1.31 (t, 6H, CH$_3$), 2.13 (m, 2H, CH$_2$), 3.21 (t, 2H, CH$_2$), 3.50

(t, 2H, CH$_2$), 4.22–4.35 (m, 5H, CH$_2$ and CH), 6.17 (d, 1H, NH). $^{13}$C NMR (CDCl$_3$) δ 13.7, 22.9, 50.9, 53.3, 58.4, 62.4, 165.8.

D. Preparation of 3-Aminopropanesulfonamidomalonate diethyl ester

A solution of 3-azidopropanesulfonamidomalonate diethyl ester (27.60 g, 0.086 mol,) in ethanol (70 mL) and 1 g of Pd/C (10%) were placed in a Parr hydrogenation apparatus under 60 psi H$_2$ for 8 hours. The hydrogen was replenished every 2 hours. The mixture was filtered through a pad of Celite and a solution of 1 N HCl in ethanol (10 mL) was added to the filtrate. The solvent was removed in vacuo and the residue was purified by column chromatography on Al$_2$O$_3$ using CH$_2$Cl$_2$/MeOH (4/1, v/v) to give 26.84 g of the title compound as the hydrochloride salt: $^1$H NMR (CDCl$_3$) δ 1.30 (t, 6, CH$_3$), 2.12 (m, 2, OCH$_2$CH$_3$), 3.21 (t, 2, CH$_2$), 3.50 (t, 2, CH$_2$), 4.26 (m, 4, OCH$_2$CH$_3$), 4.84 (d,1, CH), 6.09 (d, 1, NH), 8.29 (br.s, 2, NH$_3$). $^{13}$C NMR (CDCl$_3$) 613.6, 26.3, 42.5, 51.2, 58.5, 62.7, 165.9.

i. Example 23

Preparation of poly(HPMA)-GG-NH(CH$_2$)$_3$ SO$_2$Ama-diEt, Approx. 22 kDa

A 100 mL media bottle was charged with 3-aminopropanesulfonyl-aminomalonate diethyl ester (2.81 g, 8.46 mmol) and pyridine (80 mL) was added with stirring. p(HPMA)-GG-ONp (8.00 g, 4.22 mmol) and HOBt (0.0968 g, 0.6321 mmol) were added, the mixture was stirred for 21 hours and then placed in a 40° C. water bath. After a total of 44 hours, the reaction was complete as indicated by the free HONp equaling the total HONp by HPLC analysis. The mixture was transferred to a 1 L media bottle and the polymer was precipitated by addition of EtOAc (900 mL) with constant stirring. The solid was isolated by centrifugation (4800 rpm, 5 minutes, 5° C.). The supernatant liquid was decanted and the solid dissolved in absolute EtOH (10% solution). Bio-Rex MSZ 501 D resin (30.0 g) was added and the mixture stirred for 2.5 hours. The resin was removed by filtration and the filtrate was concentrated to an approx. 25% solution. EtOAc (900 mL) was added and the mixture stirred for 1 hour. The polymer was isolated by centrifugation, washed with EtOAc and Et$_2$O and then dried in vacuo to give 6.00 g (75%) of an off-white powder: $^1$H NMR (D$_2$O): δ 3.90 (s, 1, —CH$_2$CHOHCH$_3$), 3.20 (br d, 2, —CH$_2$CHOHCH$_3$), 2.30–1.60 (polymer backbone CH$_2$, propyl CH$_2$), 1.20 (br m, 3, —CH$_2$CHOHCH$_3$), 1.00 (br s, polymer backbone CH$_3$).

j. Example 24

Preparation of poly(HPMA)-GG-NH(CH$_2$)$_3$ SO$_2$Ama=Pt(NH$_3$)$_2$, Aprox. 22 kDa A. Preparation of poly(HPMA)-GG-NH(CH$_2$)$_3$SO$_2$Ama (CO$_2$Na)$_2$ Hydrolysis of poly(HPMA)-GG-C$_3$-Sulf-Ama-diEt was performed under the same conditions as those used for the carboxamido compounds above using poly(HPMA)-GGNH (CH$_2$)$_3$SO$_2$Ama-diEt (0.50 g, 0.2635 mmol Ama-diEt residues), 4.2 mL H$_2$O, 2 N NaOH (0.35 m, 0.70 mmol). After 30 minutes at pH 12.4–12.6, the solution was adjusted to pH <7 with Bio-Rex MSZ 501(D) resin (0.50 g).

B. Preparation of poly(HPMA)-GG-NH (CH$_2$)$_3$SO$_2$Ama=Pt(NH$_3$)$_2$O,O'-chelate (Predominantly)

The material obtained in Step A was treated with 2.05 mL of a 30,060 ppm Pt solution of cis-diamminediaquaplatinum (II) dinitrate. The pH was maintained at 5.0–5.4 for 90 minutes and then the mixture was gently stirred with Chelex resin (0.1923 g) for an additional 90 minutes after which the resin was removed by filtration.

C. Preparation of poly(HPMA)-GG-C$_3$-Sulf-Ama=Pt (NH$_3$)$_2$ N,O-chelate

The mostly O,O'-chelate from B was treated with 0.077 g (1.3175 mmol) NaCl, 0.0265 g (0.1920 mmol) NaH$_2$PO$_4$.H$_2$O and 0.2059 g (0.7681 mmol) Na$_2$HPO$_4$. The pH was adjusted to 7.4, the mixture was placed in a 38° C. water bath for 1 hour and then in a 38° C. oven for 20 hours. After centrifugal ultrafiltration and lyophilization, 0.134 g of a brown solid was obtained: $^{195}$Pt NMR (H$_2$O:D$_2$O, 93:7)δ –2018 (br s), N,O-chelate 100%; SEC M$_p$=20.3 kD, M$_w$=21.6 kD, M$_n$=14.5 kD, and PDI=1.49.

k. Example 25

Preparation of poly(HPMA)-GG-NH(CH$_2$)$_3$ SO$_2$Ama=Pt=DACH, Approx. 22 kDa

A 100 mL media bottle was charged with poly(HPMA)-GG-NH(CH$_2$)$_3$SO$_2$-Ama-diEt (6.0 g, 3.162 mmol Ama-diEt groups) and 50 mL H$_2$O. The polymer was hydrolyzed with 2N NaOH (4.2 mL) at pH 12.4–12.6 for 2 hours and then neutralized with IX resin. The pH was adjusted to 7.4 with 2N NaOH and 5% HNO$_3$ and 30.3 mL of cis-diaquo-1R, 2R-DACH—Pt(II) dinitrate (24,484 ppm Pt, 1.2 equiv/Ama-diEt) was added. The pH was increased to 5.4 and the mixture stirred overnight. Chelex resin (1.92 g) was added and the mixture was gently stirred for 90 minutes. After removal of the resin, the solution volume was adjusted to 100 mL and NaCl (0.6431 g), NaH$_2$PO$_4$.H$_2$O (0.221 g), and Na$_2$HPO$_4$.7H$_2$O (1.71 g) were added. Once the salts dissolved, the solution was filtered, held at 38° C. for 24 hours and then purified by TFF to give 5.13 g of a brown solid after lyophilization: % Pt 6.25; % H$_2$O, 9.37 %; % Pt released at 3 and 24 h, 1.0% and 1.93%, respectively; and $^{195}$Pt NMR (H$_2$O:D$_2$O, 93:7) δ–2257, approx. –2280, and –2432.

l. Example 26

Preparation of GG-NH(CH$_2$)$_3$SO$_2$Ama, diethyl ester, TFA salt

To a stirred solution of t-BOC-Gly-Gly-OH (9.29 g, 0.0400 mol) and HOBt (6.1260 g, 0.0400 mol) in DMF (18 mL) at 0° C. was added DCC (8.25 g, 0.0400 mol). While the mixture stirred at 0° C. for 45 minutes, TEA (5.0595 g, 0.0500 mol) was added to a mixture of 3-aminopropanesulfonamidomalonate diethyl ester HCl salt (13.3136 g, 0.0400 mol) in 10 mL DMF in a separate flask. This mixture was stirred at room temperature for 10 minutes, filtered and the filtrate placed under high vacuum in a 50 mL flask for 5 minutes. The DMF solution of 3-aminopropanesulfonamidomalonate diethyl ester was added to the stirring t-BOC-Gly-Gly-OH/HOBt/DCC mixture. The resulting mixture was stirred at 0° C. for 2 hours, allowed to come to ambient temperature and stirred for an additional 6 hours. The mixture was filtered and the filtrate was poured into 300 mL of water and extracted with CH$_2$Cl$_2$ (3×400 mL). The combined organic layers were washed with brine (3×300 mL) and water (3×300 mL), dried over anhydrous Na$_2$SO$_4$ and filtered. The solvent was removed in vacuo. The residue was purified on Si-gel with $CH_2Cl_2$/Acetone, 99/1 to 0/100 to give 9.10 g of product as a white solid: $^1H$ NMR ($CDCl_3$): δ 7.47 (t, 1H, NH), 7.35 (t, 1H, NH), 6.24 (d, 1H, NH), 5.83 (d, 1H, NH), 4.83 (d, 1H, CH), 4.20–4.27 (m, 4H, $OCH_2CH_3$), 3.91 (d, 2H, Gly-$CH_2$), 3.83 (d, 2H, Gly-$CH_2$), 3.37 (m, 2H, $CH_2$), 3.16 (t, 2H, $CH_2$), 2.28 (m, 2H, $CH_2$), 1.44 (s, 9H, t-butyl), 1.32 (t, 6H, $CH_3$).

A solution of t-BOC-Gly-Gly-3-aminopropylsulfonamidomalonate diethyl ester (7.7880 g, 0.0200 mol), in 40 mL of TFA/DCM 1/1 was stirred under an Argon atmosphere. After 2 hours, TLC analysis ($CH_2Cl_2$/MeOH, 9/1, v/v) indicated the reaction was complete and the solvent was removed in vacuo. The residue was triturated with 5 mL diethyl ether, filtered, and the precipitate dried in vacuo to give 7.66 g of the title compound: $^1H$ NMR ($CDCl_3$): δ 8.53 (t, 3H, $NH_2$ TFA salt), 7.66 (t, 1H, NH), 7.61 (t, 1H, NH), 6.44 (d, 1H, NH), 4.36 (d, 1H, CH), 4.19–4.26 (m, 4H, $CH_2$), 3.91 (d, 2H, $CH_2$), 3.80 (d, 2H, $CH_2$), 3.37 (m, 2H, $CH_2$), 3.16 (t, 2H, $CH_2$), 2.33 (q, 2H, $CH_2$), 1.29 (t, 6H, $CH_3$).

m. Example 27

Preparation of poly(HPMA)-GFLG-NH($CH_2$)$_3SO_2$-Ama-diEt, Approx. 24 kDa

An oven-dried 100 mL media bottle equipped with a stir bar and septum cap was charged with 2.24 g (6.74 mmol) $NH_2(CH_2)_3SO_2$-Ama-diEt HCl and 80 mL anhydrous pyridine and the mixture stirred. 8.03 g of poly(HPMA)-GFLG-ONp was added, the mixture stirred until it dissolved and then held at 40–45° C. for 44.5 hours. During this time aliquots were analyzed for free and total HONp. After 43 hours, the reaction was complete. The crude product was precipitated with 0.6 L dry EtOAc and 0.2 L diethyl ether. After stirring at ambient temperature for 1.5 hours, the precipitate was isolated by centrifugation. The supernatant was discarded and the pellet was washed, centrifuged and decanted three times with 30 mL of diethyl ether. After drying, the solid was dissolved in 80 mL absolute EtOH and gently stirred with 25.0 g of AG 501-X8 (D) IX resin ($H^+$ & $^-OH$ forms). After 2.5 hours, the resin was removed by filtration and the polymer was precipitated with 0.9 L EtOAc and 0.2 L diethyl ether. After stirring for 1 hour, the polymer was isolated and washed as before. The product was dried in vacuo to give 7.08 g of the title compound as an off-white powder: $^1H$ NMR ($CD_3OD$): δ 7.48 and 7.28 (br.s., NH & ArH), 4.7 (br.s. 1H, α-H-phe), 4.44 (br s 1H, αH-leu), 4.11 (br.m., 4H, $OCH_2CH_3$), 3.63 (br.s., $NHCH_2CH(OH)CH_3$ and $CH_2$-gly), 3.18 and 3.00 (br.m., $NHCH_2CH(OH)CH_3$), 2.1–1.2 (m, —$CH_2CCH_3$, $CH_2$-leu, CH-leu), 1.19 (brs, $NHCH_2CH(OH)CH_3$), 0.94 (br s, —$CH_2CCH_3$), 0.8 (br s, $CH_3$-leu).

n. Example 28

Preparation of poly(HPMA)-GFLG-NH($CH_2$)$_3SO_2$-Ama=Pt($NH_3$)$_2$

A. Hydrolysis of poly(HPMA)-GFLG-NH($CH_2$)$_3SO_2$-Ama-diEt

The hydrolysis was performed in the same manner as as before using poly(HPMA)-GFLG-$NH_2(CH_2)_3SO_2$-Ama-diEt (0.50 g, 0.2110 mmol Ame-diEt residues), 4.2 mL $H_2O$ (to form a 12% solution) and 2 N NaOH (0.295 mL, 0.590 mmol). After 30 minutes at pH 12.4–12.6, Bio-Rex MSZ 501 (D) resin (0.50 g) was added to reduce the pH to <7.

B. Preparation of poly(HPMA)-GFLG-$C_3$-Sulf-Ama=Pt($NH_3$)$_2$O,O'-chelate

The platination was performed as above using 1.60 mL (0.253 mmol) cis-diamminediaquaplatinum(II) dinitrate and 0.1540 g of Chelex resin.

C. Preparation of poly(HPMA)-GFLG-$C_3$-Sulf-Ama=Pt($NH_3$)$_2$ N,O-chelate

This chelate conversion and purification was performed as above using 0.0482 g (0.8248 mmol) NaCl, 0.0166 g (0.1203 mmol) $NaH_2PO_4.H_2O$, and 0.1287 g (0.4801 mmol) $Na_2HPO_4.7H_2O$. After centrifugal ultrafiltration and lyophilization, 0.219 g of the title compound was obtained as a brown solid: $^1H$ NMR ($D_2O$): δ 7.38 (br d, 5, Ar), 4.68 (br s, 1, α-H-phe), 4.40 (br s, 1, α-H-leu), 3.95 (br s, H, —$CH_2CHOHCH_3$), 3.80–3.50 (m, propyl), 3.20 (br d, $CH_2CHOHCH_3$), 2.40–1.47 (br m, $CH_2$ of polymer backbone), 1.47–1.05 (br s, $CH_2CHOHCH_3$), 1.05–0.50 (br s, $CH_3$ of polymer backbone); $^{195}Pt$ NMR ($H_2O/D_2O$, 93/7):δ −2015 (br s), N,O-chelate 100%; SEC: $M_p$=21.1 kD, $M_w$=24.0 kD, $M_n$=7.6 kD, and PDI=3.18. Pt release in PBS at 37° C., 3.02% at 3 h, 5.44% at 24 hours.

o. Example 29

Preparation of poly(HPMA)-GFLG-NH($CH_2$)$_3SO_2$-Ama=Pt=DACH

A. Hydrolysis of poly(HPMA)-GFLG-$C_3$—NH($CH_2$)$_3SO_2$-Ama-diEt

The hydrolysis of poly(HPMA)-GFLG-$C_3$-sulf-Ama-diEt was performed under the same conditions as those employed above using poly(HPMA)-GFLG-NH($CH_2$)$_3SO_2$ AmadiEt (5.50 g, 2.321 mmol Ame-diEt residues), 46 mL $H_2O$ (to form a 12% solution), 2 N NaOH (3.241 mL, 6.48 mmol) and Bio-Rex MSZ 501(D) resin (5.50 g).

B. Preparation of poly(HPMA)-GFLG-NH($CH_2$)$_3SO_2$-Ama=Pt=DACH O,O'-chelate

This compound was prepared under the same conditions as previously described using 20.50 mL of a 26,487 ppm Pt solution of cis-diaqua-1R,2R-DACH platinum(II) dinitrate and Chelex resin (1.6943 g).

C. Preparation of poly(HPMA)-GFLG-NH($CH_2$)$_3SO_2$-Ama=Pt=DACH N,O-chelate

This preparation was performed under the same conditions as those described above for similar conversions. Quantities of reagents used were 0.6428 g (11 mmol) NaCl, 0.2208 g (1.60 mmol) $NaH_2PO_4$, and 1.7156 g (6.40 mmol) $Na_2HPO_4$ for the PBS solution. After purification by tangential flow filtration, the product was obtained as 4.10 g of a brown solid: % Pt=6.58: $^1H$ NMR ($D_2O$): δ 7.38 (br d, 5, Ar), 5.8 (CH of Ama, N,O-chelate), 4.68 (br s, 1, α-H-phe), 4.40 (br s, 1, α-H-leu), 3.95 (br s, H, —$CH_2CHOHCH_3$), 3.80–3.50 3.80–3.50 (m, propyl), 3.20 (br d, $CH_2CHOHCH_3$), 2.60–2.20 (br m, DACH—$CH_2$), 2.20–1.47 (br m, $CH_2$ of polymer backbone), 1.47–1.10 (br s, $CH_2CHOHCH_3$), 1.10–0.50 (br s, $CH_3$ of polymer backbone); Pt release in PBS at 37° C., 2.12% at 3 hr, 4.54% at 24 hr.

Example 30

Dependence on pH of the isomer ratio of O,O'—Pt to N,O—Pt chelate

Four 50 mL Centrifuge tubes were each charged with 1.00 g of p(HPMA)-GFLG-Ama=Pt(NH$_3$)$_2$ (either 100% N,O-chelate) or a 92% O,O-chelate, 8% N,O-chelate mixture. These materials were dissolved in 27 mL Milli-Q water (approx a 4 wt % solution) and adjusted to the pH ranges desired using 1 M NaOH or 5% HClO$_4$ as appropriate. The samples were then heated, with stirring, in a 38° C. water bath and maintained within their specified pH ranges. Timed aliquots were taken and frozen until a suitable time at which point the solutions were concentrated by centrifugal ultrafiltration (one spin down at 4800 rpm, 30° C.) and then transferred to an NMR tube. A small amount of D$_2$O was added to each tube and the $^{195}$Pt NMR spectra were recorded. The data are presented in Tables 1–3.

Example 31

Percent Pt released versus pH over time for poly (HPMA)-GFLG-Ama-Pt(NH$_3$)$_2$, N,O-chelate, approx. 20 kDa.

A stock solution of citrate PBS that was 10 mM in citrate, 20 mM in phosphate, and 100 mM in NaCl was prepared and split into bottles which were then adjusted to the desired pH. The bottles were warmed to 37° C. in an oven and poly (HPMA)-GFLG-Ama=Pt(NH$_3$)$_2$, N,O-chelate, ~20 kDa, was added to give a concentration of approximately 2 mg of polymer platinum conjugate per mL buffer. The mixtures were well mixed to give colorless solutions. At the indicated times, three approximately 2.5 mL aliquots were removed from the solution at each pH and transferred to previously washed YM-3 ultracentrifuge devices (Amicon) and spun at 5000 RCF and 37° C. for 50 min. Once all samples for all time points have been collected and prepared, the filtrates and stock solutions are analyzed against Pt standards (0–10 ppm) by ICP-OES at the platinum emission line of 214.42 nm. For each time point and at each pH, three samples were prepared and analyzed.

Example 32

In vitro activity of O,O'—Pt and N,O—Pt chelate

The relative cytotoxic activity of various O,O'—Pt chelate analogs were evaluated in vitro by means of a clonogenic (colony-formation) assay employing a tissue culture of B16F10 melanoma cells. In this way, the activity of the analogs was compared to that of cisplatin and carboplatin. The effect of conversion to an N,O—Pt chelate was also evaluated. Briefly, cells were seeded into culture dishes and allowed to attach. The cultures were incubated for 7 days in medium containing the desired concentration of the test agent. After fixation, the number of cell clusters containing >50 cells was scored as a colony. Each concentration of test agent was assayed in triplicate. The mean number of colonies in each of the triplicate dishes was divided by the mean number of colonies in the control (no test agent) dishes to obtain a percent survival value for each concentration of test agent. The IC$_{50}$ (concentration resulting in 50% inhibition of growth) of each of the agents was determined by linear regression analysis using the data values directly above and below the 50% survival point. The results are shown in Table 8.

TABLE 5

Cytotoxicity results from Clonogenic assays for O,O'—Pt and N,O—Pt chelates of amidomalonates.

| CHELATE | IC$_{50}$ (µM) |
| --- | --- |
| Control | >300 |
| p(HPMA)-GFLG-Ama, 90 kDa, O,O'—Na | >100 |
| p(HPMA)-GFLG-Ama=Pt=(NH$_3$)$_2$, 25 kDa, N,O—Pt | 3.4 |
| p(HPMA)-GFLG-Ama=Pt=(NH$_3$)$_2$, 25 kDa, O,O'—Pt | 0.8–1.1 |
| p(HPMA)-GFLG-Ama=Pt=(NH$_3$)$_2$, 45 kDa, O,O'—Pt | 1.0 |
| p(HPMA)-GFLG-Ama=Pt=(NH$_3$)$_2$, 90 kDa, O,O'—Pt | 0.9 |
| p(HPMA)-GFLG-Ama, 45 kDa, O,O'—Na | >100 |
| p(HPMA)-GFLG-Ama=Pt=DACH, 25 kDa, O,O'—Pt | 1.0 |
| p(HPMA)-GFLG-Ama=Pt=DACH, 25 kDa, N,O—Pt | <4 |
| Cisplatin | 0.5 |
| Carboplatin | 2.4 |

Example 33

Toleration and Maximum Tolerated Dose Studies

Single-dose IV studies comparing the O,O'—Pt chelate to the N,O—Pt chelate forms of poly(HPMA)-GFLG-Ama-Pt (NH$_3$)$_2$, M$_w$ ~20 kD show that the maximum tolerated doses (MTD) in mice are 80–100 and 400 mg P/kg for the O,O'—Pt chelate and the N,O—Pt chelate, demonstrating the greater safety margin afforded by the polymer bound N,O—Pt chelate. For these studies, the MTD was defined as the highest dose evaluated in which no mouse deaths resulted from drug-induced toxicity.

The toleration of multiple doses of both chelates, as expressed by the maximum mean body weight loss of groups of 10 mice bearing B16 melanoma tumors given five daily doses of either chelate, is shown in Table 9. The data also indicate the lack of toxicity of the N,O—Pt chelate at an equivalent dose to that of the O,O'—Pt chelate and the substantially higher dose of the N,O—Pt chelate necessary to produce an equivalent mean weight loss.

TABLE 6

Toleration Expressed as Mean Percent Body Weight Reduction for Daily dosing × 5 of poly(HPMA)-GFLG-Ama=Pt(NH$_3$)$_2$, O,O'—Pt and N,O—Pt chelates, 25 kDa.

| O,O'—Pt Chelate | | N,O—Pt Chelate | |
| --- | --- | --- | --- |
| Dose (mg Pt/kg) | % Weight loss | Dose (mg Pt/kg) | % Weight loss |
| 7.5 | −10.3 | 10 | +5.6 |
| 20 | −29.9 | 20 | −2.5 |
|  |  | 40 | −4.8 |
|  |  | 80 | −7.7 |
|  |  | 200 | −19.9 |
|  |  | 240 | −26.0 |

Example 34

Tumor Growth Inhibition in a Subcutaneous (s.c.) B16 Melanoma Model: N,O—Pt chelate Tumor growth inhibition of poly(HPMA)-GFLG-Ama=Pt (NH$_3$)$_2$, N,O—Pt chelate, 25 kDa versus cisplatin and saline control was evaluated in female C57BL/6 mice. The N,O—Pt chelate and chelate and cisplatin were dosed at 7.5 mg Pt/kg and 3 mg Pt/kg on a qd×5 schedule. The N,O—Pt chelate dose is well below its MTD, while the cisplatin dose is near its MTD. Ten animals per treatment group were inoculated s.c. in the right rear flank with 106 B16F10 murine melanoma cells. Beginning at day 6 post-implantation, tumor size was measured daily using calipers under light Methiurane anesthesia. The mass of the resulting tumor (in mg) was estimated using the formula $(W^2 \times L)/2$ where W is the length of the shorter tumor dimension, and L is the length of the longer dimension in mm. Treatment commenced in each animal when the tumor was 50 mg or larger in size.

Figure 9:
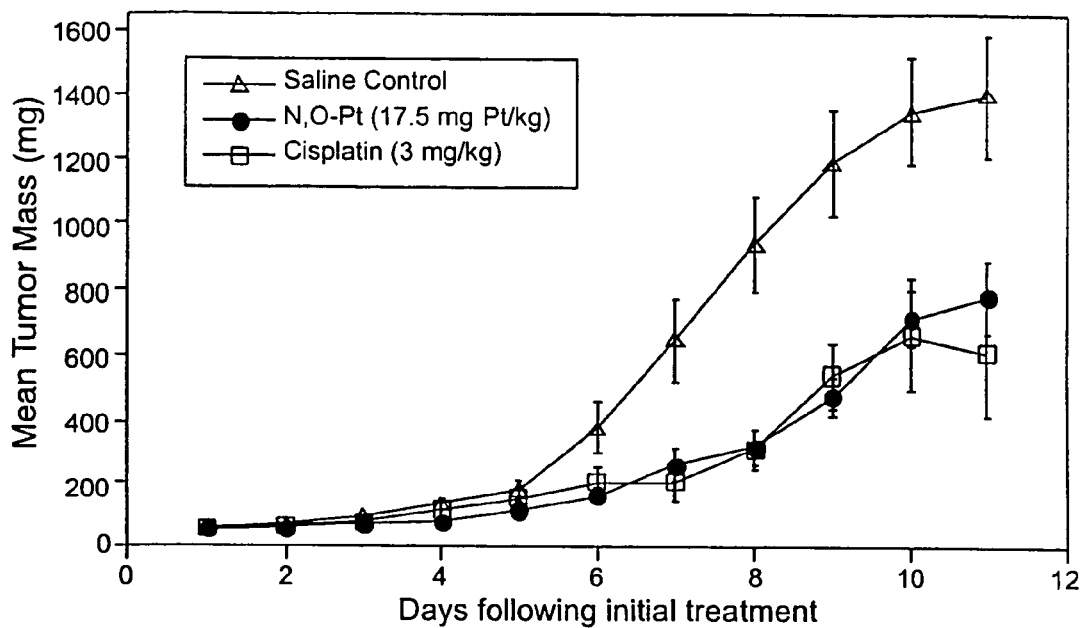
FIG. 9 shows a plot from the B16 melanoma tumor growth inhibition study of Example 35 in which saline was used as a control, cisplatin was dosed near its MTD (Maximum Tolerated Dose), and the N,O—Pt chelate of poly (HPMA)-GFLG-Ama=Pt(NH$_3$)$_2$ was dosed well below its MTD.

Each study animal was followed individually, such that Day 1 of treatment for each animal corresponded to the day on which the size of the tumor indicated commencement of dosing. All test compounds were dosed IV via the tail vein, and administered in a volume of 0.2–0.3 mL per 20 g body weight. Animals were observed and weighed daily prior to dosing for establishment of dosing volumes and daily thereafter until the termination of the study. The results are shown in FIG. 9.

Example 35

Tumor Growth Inhibition in a s.c. B16 Melanoma Model: O,O'—Pt Chelate

Figure 10:
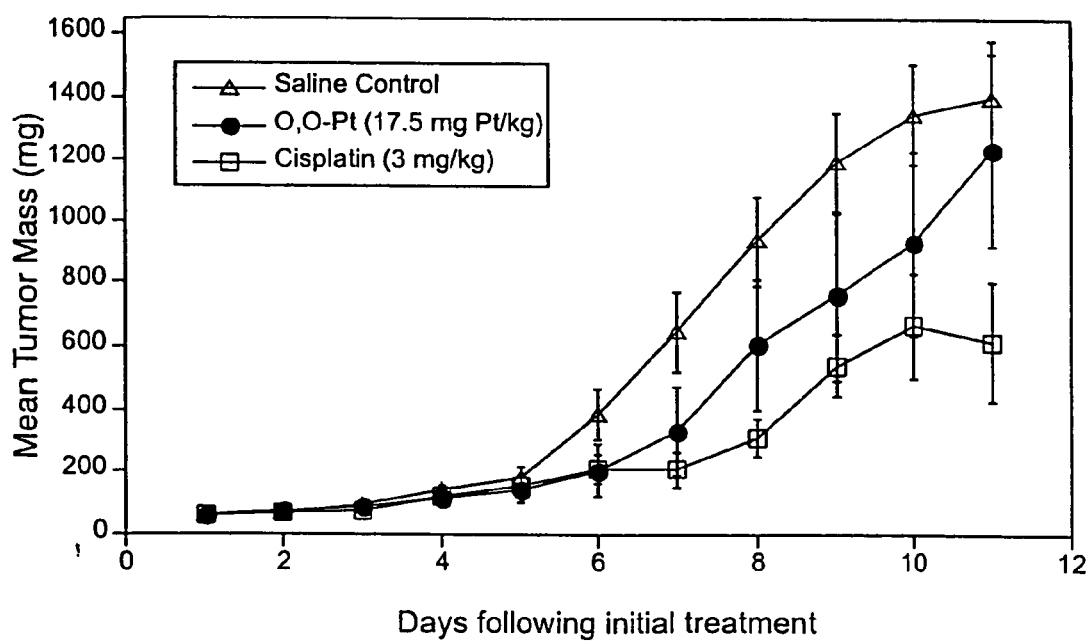
FIG. 10 shows a plot from the B16 melanoma tumor growth inhibition study of Example 36 where saline was used as a control, cisplatin was dosed near its MTD, and the O,O'—Pt chelate of poly(HPMA)-GFLG-Ama=Pt(NH$_3$)$_2$ was also dosed near its MTD.

Tumor growth inhibition of poly(HPMA)-GFLG-Ama=Pt$(NH_3)_2$, O,O'—Pt chelate, 25 kDa (O,O'—Pt), versus cisplatin and saline control was evaluated in female C57BL/6 mice. The O,O'—Pt chelate and cisplatin were dosed at 17.5 mg Pt/kg and 3 mg/kg on a qd×5 schedule. The O,O'—Pt chelate dose is near its MTD as is the cisplatin dose. Results are shown in FIG. 10.

Example 36

Tumor Growth Inhibition in a s.c B16 Melanoma Model: N,O—Pt Chelate

Figure 11:
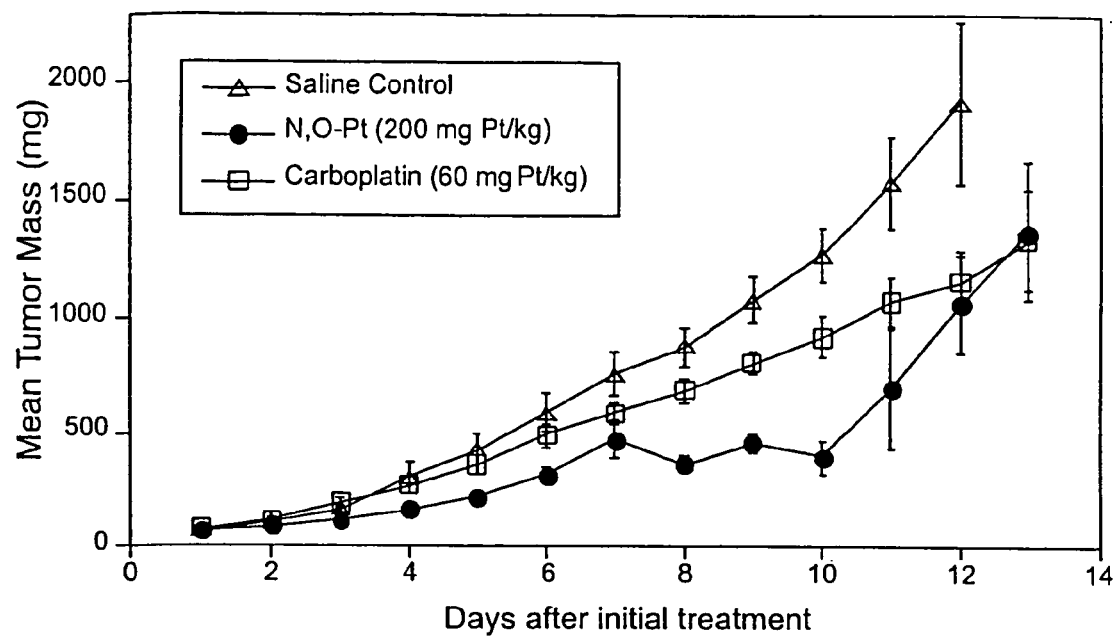
FIG. 11 shows a plot from the B16 melanoma tumor growth inhibition study of Example 37 where saline was used as a control, carboplatin was dosed near its MTD, and the N,O—Pt chelate of poly(HPMA)-GFLG-Ama=Pt(NH$_3$)$_2$ was dosed near its MTD.

Tumor growth inhibition of poly(HPMA)-GFLG-Ama=Pt$(NH_3)_2$ N,O—Pt chelate, 25 kDa (N,OPt), versus carboplatin and saline control was evaluated in female C57BL/6 mice. The N,O—Pt chelate and carboplatin were dosed at 200 mg Pt/kg and 65 mg/kg on a qd×5 schedule. This N,O—Pt chelate dose is near its MTD as is the carboplatin dose. Results are shown in FIG. 11.

Example 47

Tumor Growth Inhibition in a s.c. Squamous Cell Xenograft Model: N,O—Pt Chelate

Figure 12:
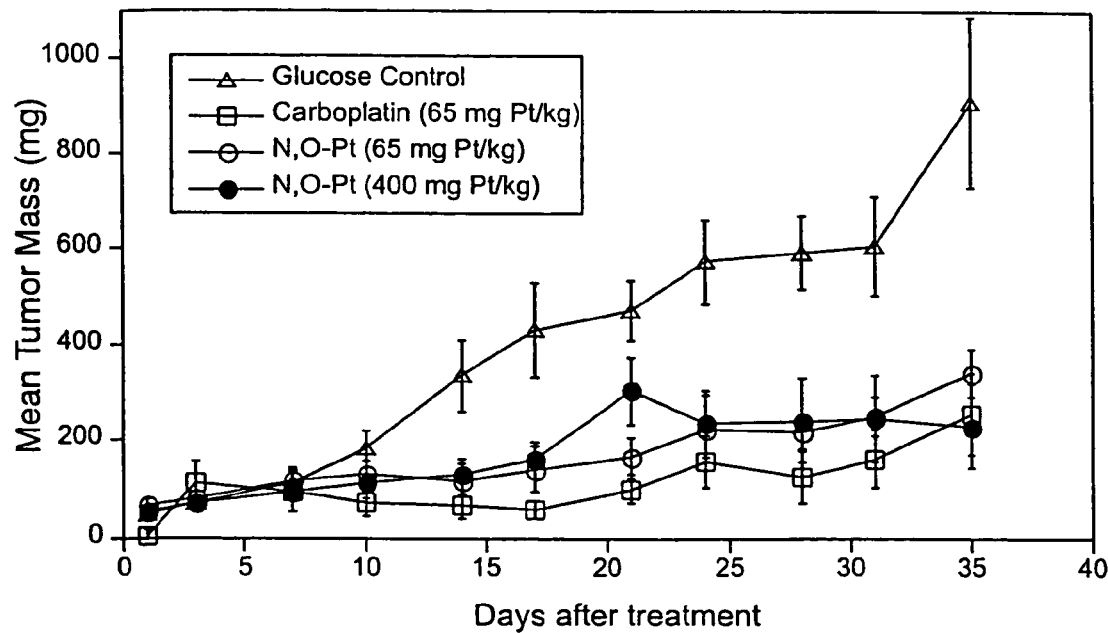
FIG. 12 shows a plot from the human xenograft tumor growth inhibition study where isotonic glucose was used as a control, carboplatin was dosed near its MTD, and the N,O—Pt chelate of poly(HPMA)-GFLG-AmaPt(NH$_3$)$_2$ was dosed well below and near its MTD.
Figure 13:
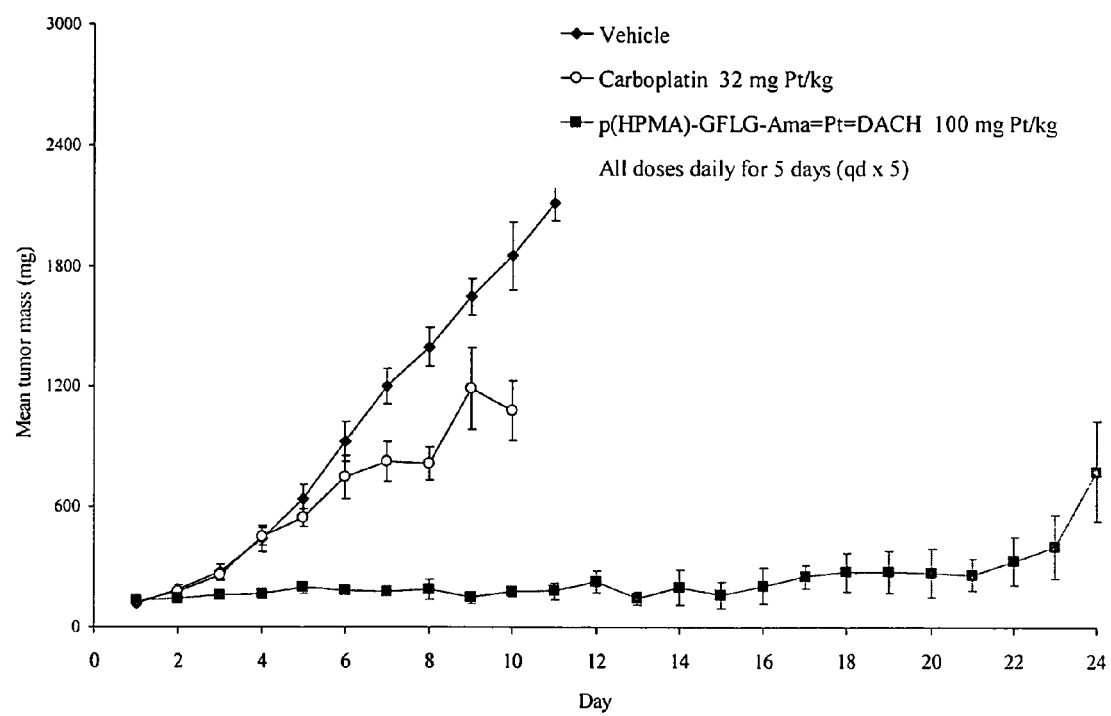
FIG. 13 is a graphic representation of the results obtained from the experiment described in Example 38, which is a comparison of the antitumor activity of p(HPMA)-GFLG-Ama=Pt=DACH and of carboplatin in the B16 melanoma tumor model.
Figure 14:
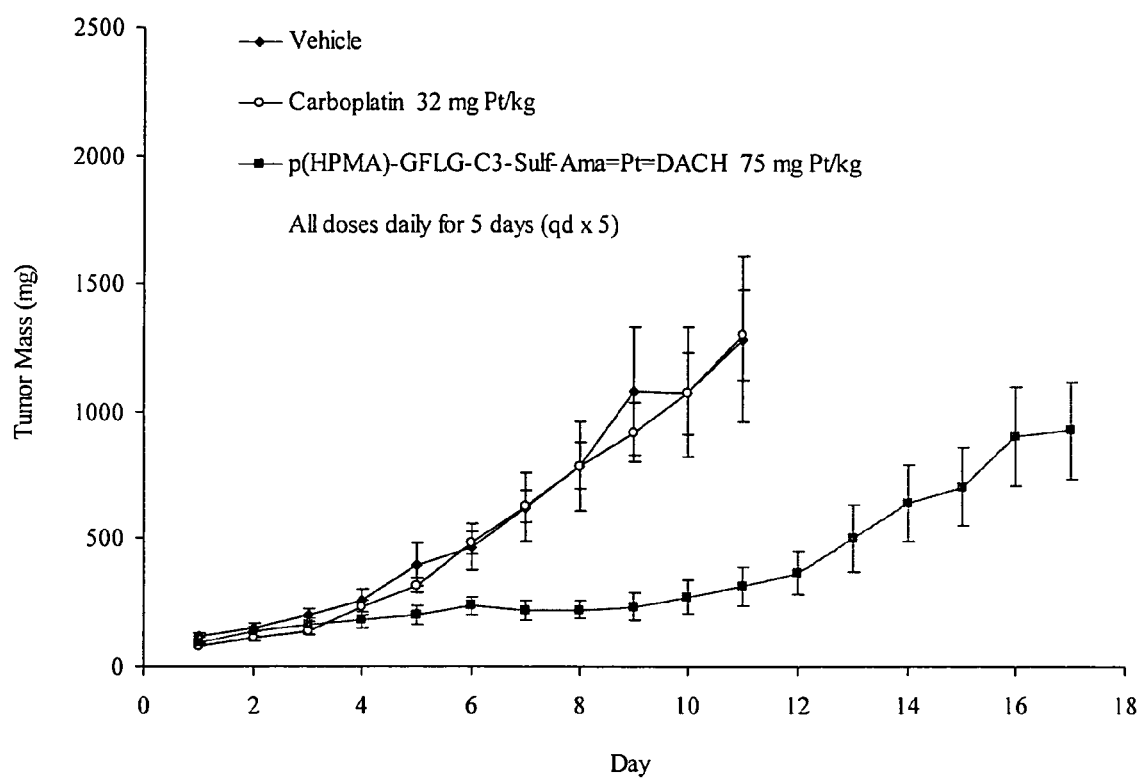
FIG. 14 is a graphic representation of the results obtained from the experiment described in Example 39, which is a comparison of the antitumor activity of p(HPMA)-GFLG-C3-Sulf-Ama=Pt=DACH and of carboplatin in the B16 melanoma tumor model.

Tumor growth inhibition of poly (HPMA)-GFLG-AmaPt$(NH_3)_2$, N,O—Pt chelate, 25 kDa, versus carboplatin and vehicle control (isotonic glucose) was evaluated in groups of 7 BALB/c nu/nu mice per treatment group. Human squamous tumor cells (UMSCC10b) were implanted ($10^6$ cells per site) at four sites (left and right shoulder and left and right flank). The N,O—Pt chelate and carboplatin were dosed at 400 mg Pt/kg and 65 mg/kg as a single IP injection. The N,O—Pt chelate dose is near its MTD as is the carboplatin dose. When the tumors reached a group mean of 50 mg, all of the mice were administered the test regimen. Results are shown in FIG. 12.

2. Example 38

Antitumor Activity of p(HPMA)-GFLG-Ama=Pt=DACH in the B16 Melanoma Model Using a Multi-Dose Protocol A study was conducted to compare the antitumor activity of poly(HPMA)-GFLG-Ama=Pt=DACH with that of carboplatin in the B16 melanoma model when each agent was administered as an IP injection daily for 5 days (qd×5). The poly(HPMA)-GFLG-Ama=Pt=DACH material was also given at days 15, 16, and 17. Both compounds were given at their respective maximum tolerated (equitoxic) doses on this regimen.

Female C57BL/6 mice weighing 18–20 g were implanted s.c. with $10^6$ B16F10 tumor cells harvested from tissue culture. The size of the resulting tumor was followed individually throughout the study. Tumor mass (in mg) was calculated as $(W^2 \times L)/2$, where W is the shorter tumor dimension and L is the longer tumor dimension. Individual treatments were administered when the tumor was 75–100 mg in size. The injection volume was 0.04 mL per gram of body weight, and the drug was administered intraperitoneally. Tumor mass and body weight were measured daily. Data are expressed as the mean±SEM of the tumor mass and are plotted until 50% of the animals in each treatment group have died or been sacrificed due to excessive tumor mass, tumor ulceration, or morbidity. For comparison of the activity of different agents, each administered at its respective maximum tolerated doses (MTD), the MTD is defined as that dose which reproducibly induces no more than 10% (1 out of each 10 animals per group) early toxic deaths not attributable to tumor burden, and which results in a mean maximum body weight loss (i.e., the group mean of the nadir in each individual mouse weight, regardless of the day on which it occurred) of 10–15%, followed by recovery in lost weight.

The maximum tolerated dose of p(HPMA)-GFLG-Ama=Pt=DACH on a qd×5 schedule in this model is 100 mg Pt/kg, and the corresponding maximum tolerated dose of carboplatin is 60 mg/kg (equivalent to 32 mg Pt/kg). Plots of the mean tumor growth in each treatment group are shown in Figure A. These results show that carboplatin produced a modest inhibition of tumor growth. By contrast, tumor growth was substantially slowed and prolonged following the p(HPMA)-GFLG-Ama=Pt=DACH treatment regimen.

3. Example 39

Antitumor Activity of p(HPMA)-GFLG-C3-Sulf-Ama=Pt=DACH in the B16 Melanoma Model using a multi-dose protocol A study was conducted to compare the antitumor activity of p(HPMA)-GFLG-C3-Sulf-Ama=Pt=DACH with that of carboplatin in the B16 melanoma model when each agent was administered as an IP injection daily for 5 days (qd×5). Both compounds were given at their respective maximum tolerated (equitoxic) doses on this regimen.

The methods utilized in this study were identical to those utilized for the p(HPMA)-GFLG-C3-Sulf-Ama=Pt=DACH study of Example 38.

The maximum tolerated dose of p(HPMA)-GFLG-C3-Sulf-Ama=Pt=DACH on a qd×5 schedule in this model is 75 mg Pt/kg, and the corresponding maximum tolerated dose of carboplatin is 60 mg/kg (equivalent to 32 mg Pt/kg). Plots of the mean tumor growth in each treatment group are shown in Figure B. These results show that carboplatin produced very little inhibition of tumor growth in this study. By contrast, a more marked inhibition in tumor growth was observed following the p(HPMA)-GFLG-C3-Sulf-Ama=Pt=DACH treatment regimen.

CONCLUSION

Thus, the present invention provides means for selectively preparing essentially pure amidomalonate O,O'—Pt and N,O—Pt chelates. It also provides the essentially pure amidomalonate O,O'—Pt and N,O—Pt chelates prepared using the methods. The N,O— chelates are shown to be relatively stable at pHs of about 6.0 and above and to release small Pt species at pHs below that pH with the result that the active small Pt species are selectively released in structures such as tumors and liposomes where lower pHs are found.

It will be apparent to those skilled in the art that changes and variations may be made in the method disclosed herein. Such changes and variations are within the scope of this invention. For example, without limitation, it will be recognized by those with skill in the the art that other polymers other than poly(HPMA) and poly(glu) that have carboxyl, sulfonate, or sulfate groups (including but not limited to glycosaminoglycans such as hyaluronic acid, dermantan sulfate, heparin, chondroitin sulfate and the like) could be coupled to Ama-diEt, directly or through spacers such as aminoacids or polyaminoacids under aqueous or nonaqueous conditions with conventional coupling agents. These polymer-amidomalonate conjugates could then be hydrolyzed and platinated as described herein to give O,O'—Pt chelates, which, in turn, could be converted to give the corresponding N,O—Pt chelates. Likewise, one skilled in the art would recognize based on the disclosures herein that N,O—Pt chelates could be made of the half ester or monoalkyl amidomalonate. For example, the monoester could be prepared by partial hydrolysis of the dialkyl ester with 1 equiv of NaOH or KOH or by treatment with malonic acid or hydrolyzed N-acylamidomalonatic acid to generate the half ester of both. After purification, the monoester could be platinated at pH 4–5. Then, the pH would be raised to approximately 6 or higher to give the N,O—Pt complex. All such permutations of the compounds herein are within the scope of this invention.

REFERENCES

1. Appleton, T. G., Hall, J. R., Neale, D. W., and Thompson, C. S. M., "Reactions of the cis-Diamminediaquaplatinum (II) Cation with 2-Aminomalonic Acid and Its Homologues, Aspartic and Glutamic Acids. Rearrangements of Metastable Complexes with Carboxylate-Bound Ligands to N,O-Chelates and Formation of Di- and Trinuclear Complexes.sup.1", Inorg Chem, 29,3985–3990 (1990n385).
2. Bogdanov, Jr., A. A., et al., Bioconjugate Chem. 7:144–149 (1996).
3. Duncan, et al., U.S. Pat. No. 5,965,118 issued Oct. 12, 1999 and assigned to Access Pharmaceuticals, Inc., Dallas, Tex.
4. Duncan, R., et al., Brit. J Cancer 55:165–174 (1987).
5. Duncan, R., et al., Anti-Cancer Drugs 3:175–210 (1992).
6. Fiebig, H. H., et al., Proc. Am. Asso. for Cancer Res. 37:297, Abstract No. 2021(1996).
7. Filipova-Voprsalova, M., et al., J. Controlled Release 17(89–98) (1991).
8. Freise, J., et al., Arch. Int. Pharmacodyn. 258:180–192 (1982).
9. Fuji, K., et al., Proc. Intern. Symp. Control. Rel. Bioact. Mater. 23:639–640 (1996).
10. Gandolfi, O., "Novel Organoplatinum(II) Complexes and Method for the Preparation Thereof", U.S. Pat. No. 4,614,811.
11. Gandolfi, O., Apfelbaum, H. C., and Blum, J., "Aminomalonato(1,2-diaminocyclohexane)platinum(II): A Competitive Antitumor Compound Within a New Class of Neutral, Chemically Stable, Water Soluble, Functionalized Platinum(II) Complexes", Inorganic Chimica Acta, 135, 27–31 (1987).
12. Gianasi, E., Wasil, M., Evagorou, E. G., Keddle, A., Wilson, G., and Duncan, R., "HPMA copolymer platinates as novel antitumour agents: in vitro properties, pharmacokinetics and antitumour activity in vivo", Eur J Cancer, 35, 994–1002 (1999).
13. Gibson, D., Rosenfeld, A., Apfelbaum, H., and Blum, J., "Multinuclear (.sup.195 Pt, .sup.15 N, .sup.13 C) NMR Studies of the Reactions between cis-Diaminediaquaplatinum(II) Complexes and Aminomalonate", lnorg Chem, 29, 5125–5129 (1990).
14. Han, M. J., et al., J. Bioact. and Biocompat. Polymers 9:142 (1994).
15. Johnsson, A., and Cavallin-St.ang.hl, E., Anti-Cancer Drugs 7:70–77 (1996).
16. Neuse, E. W., et al., J. Inorganic and Organometallic Polymer 5(3):195–207 (1995).
17. Prestayko, A. W., Cancer and Chemo. Vol III (Crooke, et al., Eds.) Academic Press, NY, 133–154 (1981).
18. Schechter, B., et al., J. Controlled Release 10:75–87 (1989).
19. Seymour, L. W., et al., J. of Biomed. Mat. Res. 21:1341–1358 (1987).
20. Steerenberg, P. A., et al, International Journal of Pharmaceutics 40:51–62 (1987).
21. Sur, B., et al, Oncology 40:372–376(1983).
22. Talebian, A., et al. (a), "Synthesis and Characterization of a Series of Water Soluble Amidomalonato-(1R,2R-Cyclohexanediamine)Platinum(II) Complexes", J. Coor. Chem, 22,165–173 (1990).
23. Talebian, A., et al. (b), "Murine anti-tumor activity of new water soluble platinum (II) complexes with reduced toxicity", Anti-Cancer Drug Design, 5, 371–380 (1990).
24. Weiss, R. B., et al., Drugs 46(3):360–377 (1993).
25. Bogdanov et al., "Graft Co-Polymer Adducts of Platinum (II) Compounds", U.S. Pat. No. 5,871,710.
26. Bancroft et al., ".sup.195 Pt NMR Kinetic and Mechanistic Studies of cis- and trans-Diamminedichloroplatinum(II) Binding to DNA", J. Am Chem. Soc. 112: 6860–6871(1990).
27. Kopecek, et al. "Synthetic Polymeric Prodrugs", U.S. Pat. No. 5,037,883.
28. Matsumura et al. "A new concept for macromoleculear therapeutics in cancer therapy: mechanism of tumoritropic accumulation of proteins and the antitumor agent SMANCS", Cancer Res. 46: 6378–6392 (1986).
29. Yoguchi, et al. "Early phase tumor accumulation of macromolecules: a great difference in clearance rate between tumor and normal tissues, Jpn. J. Cncer Res. 89: 307–314 (1998).
30. Song, et al. "Synthesis and hydrolytic properties of polyphosphazene/(diamine) platinum/saccharide conjugates" J. Controlled Release 55: 161–170 (1998).
31. Sohn et al. "Synthesis and antitumor activity of novel polyphosphazene(diamine)platinum(II) conjugates" Inter. J. of Pharmaceutics 153: 79–91 (1997).
32. Li, et al. "Complete Regression of Well-established Tumors Using a Novel Water-soluble Poly(L-Glutamic Acid)-Paclitaxel Conjugate" Cancer Research 58: 2404–2409 (1998).
33. Mendichi, R. et al. "Molecular Characterization of Polymeric Antitumor Drug Carriers by Size Exclusion Chromatography and Universal Calibration" J. Liq. Chrom. and Rel Tech. 19:1591–1605 (1996).

34. Pinciroli, et al. ".sup.1H NMR Characterization of Methacrylamide Polymer Conjugates with the Anti-Cancer Drug Doxorubicin" Magn. Reson. Chem. 35: 2–8 (1997).
35. Gandolfi et al. Inorg. Chim Acta 135: 27–31 (1987).
36. Appleton et al. "Reaction of cis-Diamminediaquaplatinum(II) cation with N-Acetylglycine" Inorg. Chem. 28: 815–819 (1989).
37. Danishefsky et al. "Conversion of Carboxyl Groups of Mucopolysaccharides into Amides of Amino Acid Esters" Carbohyd. Res. 16: 199–205 (1971).
38. Tsujihara et al, "Novel Organic Platinum Complex and Process for the Preparation Thereof" U.S. Pat. No. 4,882,447.
39. Chao, et al. "Interaction of Cis Platinum(II) Compounds with Poly(1-glutamate). A Doubly Anchored Spin-Label and a Doubly Anchored Chromophore-Label" J. Am. Chem. Soc. 99: 8024–8032 (1977).
40. Criado, et al. "Structural Characterization, Kinetic Studies, and in Vitro Biological Activity of New cis-Diamminebis-cholylglycinate(O,O') Pt(II) and cis Diannminebisursodeoxycholate(O,O') Pt(II) Complexes" Bioconj. Chem. 11:167–174 (2000).
41. Rosenberg et al. "Platinum Compounds: A New Class of Potent Antitumour Agents" Nature (London) 222: 385 (1969).
42. Sur et al. "Effect of liposomal Encapsulation of Cisplatinum diamminodichloride in the Treatment of Ehrlich Ascites Carcinoma" Oncology 40: 372–6 (1983).
43. Talebian, et al. "Aspartato(1,2-cyclohexanediamine) platinum(II) complexes: synthesis and characterization; effects of minor impurities on antitumor activity" Inorg. Chim. Acta 179: 281–287 (1991).
44. Gibson, D., Rosenfeld, "Multinuclear(.sup.195 Pt, .sup.15 N, .sup.13 C) NMR Studies of the Reactions between cis-Diaminediaquaplatinum(II) Complexes and Aminomalonate", Inorg Chem, 29: 5125–5129 (1990).
45. Harrap, "Preclinical Studies Identifying Carboplatin as a Viable Cisplatin Alternative" Cancer Treat. Rev. 21(Suppl. A): 21–33 (1985).
46. Posner et al, "The Role of Induction Chemotherapy in the Curative Treatment of Squamous Cell Cancer of the Head and Neck" Semin Oncol, 27(4 Suppl 8):13–24 (2000).
47. Steerenberg et al, "Liposomes as Drug Carrier System for Cis-diamminedichloroplatinum(II). II. Antitumor Activity in vivo, Induction of Drug Resistance, Nephrotoxicity and Pt Distribution" Cancer Chemother Pharmacol. 21:299–307 (1988).
48. K. D. Paull et al, "Display and Analysis of Patterns of Differential Activity of Drugs against Human Tumor Cell Lines: Development of Mean Graph and COMPARE Algorithm" J. Natl. Cancer Inst. 81: 1088 (1989).
49. Physician's Desk Reference 51th ed, Medical Economics:Montvale, N.J., 1997 Devita et al. CANCER Principles & Practice of Onology 4.sup.th ed, J. B. Lippincott Company: Philadelphia, Pa. 1993, p395.
50. Seymour, "Passive Tumor Targeting of Soluble Macromolecules and Drug Conjugates" Crit Rev Ther Drug Carrier Syst 9(2):135–87 (1992).
51. Veronese et al. "Bioconjugation in Pharmaceutical Chemistry" Farmaco 54(8):497–516 (1999).
52. Seymour et al. "Influence of Molecular Weight on Passive Tumour Accumulation of a Soluble Macromolecular Drug Carrier" 31A: 766–770 (1995).
53. Seymour et al, "The Pharmacokinetics of Polymer-bound Adriamycin" Biochem Pharmacol. 39: 1125–31 (1990).
54. Pimm et al, "Gamma Scintigraphy of the Biodistribution of 123I-labelled N-(2-hydroxypropyl)methacrylamide Copolymer-doxorubicin Conjugates in Mice with Transplanted Melanoma and Mammary Carcinoma" J Drug Target. 3: 375–83 (1996).
55. Duncan et al, "Preclinical Toxicology of a Novel Polymeric Antitumour Agent: HPMA Copolymer-doxorubicin (PK1)" Hum Exp Toxicol. 17: 93–104 (1998).
56. Thomson et al, "Population pharmacokinetics in phase I drug development: a phase I study of PK1 in patients with solid tumours" Br J Cancer. 81: 99–107 (1999).
57. Minko et al, "Efficacy of the Chemotherapeutic Action of HPMA Copolymer-bound Doxorubicin in a Solid Tumor Model of Ovarian Carcinoma" Int J Cancer. 86: 108–17 (2000).
58. Fraier et al, "Determination of a new polymer-bound paclitaxel derivative (PNU 166945), free paclitaxel and 7-epipaclitaxel in dog plasma and urine by reversed-phase high-performance liquid chromatography with UV detection" J Chromatogr A 797: 295–303 (1998).
59. Caiolfa et al, "Polymer-bound Camptothecin: Initial Biodistribution and Antitumor Activity Studies" J Control Release. 65: 105–19 (2000).
60. Li et al, "Biodistribution of paclitaxel and poly(L-glutamic acid)-paclitaxel conjugate in mice with ovarian OCa-1 tumor" Cancer Chemother Pharmacol., 46: 416–22 (2000).
61. Conover et al, "Camptothecin Delivery Systems: enhanced efficacy and tumor accumulation of camptothecin following its conjugation to polyethylene glycol via a glycine linker" Cancer Chemother Pharmacol, 42: 407–14 (1998).
62. Duncan, "Drug-polymer conjugates: Potential for improved chemotherapy" Anti-Cancer Drugs, 3: 175–210 (1992).
63. Gianasi, et al. "HPMA Copolymer Platinates as Novel Antitumour Agents: In Vitro Properties, Pharmacokinetics and Antitumour Activity In Vivo" European J. Cancer 35: 994–1002 (1999).
64. Schechter et al, "Increased therapeutic efficacy of cis-platinum complexes of poly-L-glutamic acid against a murine carcinoma" Int J Cancer 1987 Mar. 15;39(3): 409–13.
65. Bogdanov, Jr. et al., "An adduct of cis-diamminedichloroplatinum(II) and poly(ethylene glycol)poly(L-lysine)-succinate: synthesis and cytotoxic properties" Bioconjug Chem. 1996 January–February;7(1): 144–9.
66. Han, et al., "Synthesis and Antitumor Activity of Polyanion-Pt-complexes containing Alicyclic Amines as Ligands" J. Bioactive and Compatible Polymers 9: 142–151 (1994).
67. Johnsson et al. "A topographic study on the distribution of cisplatin in xenografted tumors on nude mice" Anti-Cancer Drugs 7: 70–77 (1996).
68. Fiebig, et al., "GB-21, a novel platinum polymer with antitumor activity in human renal and mammary xenografts" Proc. American Association for Cancer Research, 37:297 abs# 2021 (1996).
69. Filipova-Voprsalova et. al., "Biodistribution of trans-1, 2-diaminocyclohexane-trimellitoplatinum(II) attached to macromolecular carriers" J. Controlled Release 17:89–98 (1991).

70. Fuji et al, "Control of Pharmacokinetics and Nephrotoxicity of cis-DDP by Alginate" Proc. Int. Symp. Controlled Rel. Bioact. Matr., 23: 639–40 (1996).
71. Neuse, et al. "cis-Diaminedichloroplatinum(II) complexes reversibly bound to water-soluble polyasparatamide carrier for chemotherapeutic applications. I. Platinum coordination to carrier-attached ethylenediamine ligands" J. Inorg. Organomet Polym., 1(2): 147–165 (1995).
72. Schechter, et al., "Soluble polymers as carriers of cis-platinum" J. Controlled Release 10: 75–87 (1989).
73. Heppeler et al, "Receptor targeting for tumor localisation and therapy with radiopeptides" Curr Med Chem 2000 September;7(9):971–94.
74. Schlaeppi et al. "Targeting vascular endothelial growth factor (VEGF) for anti-tumor therapy, by anti-VEGF neutralizing monoclonal antibodies or by VEGF receptor tyrosine-kinase inhibitors" Cancer Metastasis Rev. 18: 473–81 (1999).
75. Sudimack et al. "Targeted drug delivery via the folate receptor" Adv Drug Deliv Rev. 41: 147–62 (2000).
76. Dubowchik et al. "Receptor-mediated and enzyme-dependent targeting of cytotoxic anticancer drugs" Pharmacol Ther 83:67–123 (1999).
77. Weiner, "An overview of monoclonal antibody therapy of cancer" Semin Oncol 26, Suppl 12: 41–50 (1999).
78. Buolamwini, "Novel anticancer drug discovery" Curr Opin Chem Biol 3:500–9 (1999).
79. McIntosh et al, "Pharmacokinetics and tissue distribution of cisplatin and conjugates of cisplatin with carboxymethyldextran and A5B7 monoclonal antibody in CD1 mice" J Pharm Sci. 86:1478–83 (1997).
80. Hata et al, "Immunotargeting chemotherapy for AFP-producing pediatric liver cancer using the conjugates of anti-AFP antibody and anti-tumor agents" J Pediatr Surg. 27: 724–7 (1992).
81. Gust et al, "Investigation of the configurational and conformational influences on the hormonal activity of 1,2-bis(2,6-dichloro-4-hydroxyphenyl)ethylenediamines and of their platinum(II) complexes. 1. Synthesis, estradiol receptor affinity, and estrogenic activity of diastereomeric [N-alkyl- and N,N'-dialkyl-1,2-bis(2,6-dichloro-4-hydroxyphenyl)ethylenediamine]dichloroplatinum(II) complexes" J Med Chem. 38: 2070–9 (1995).
82. DiZio et al, "Estrogen platinum-diamine complexes: preparation of a non-steroidal estrogen platinum-diamine complex labeled with platinum-191 and a study of its binding to the estrogen receptor in vitro and its tissue distribution in vivo" J Steroid Biochem Mol Biol 42: 363–73 (1992).
83. Vitols et al, "Platinum-folate compounds: synthesis, properties and biological activity" Adv Enzyme Regul. 26: 17–27 (1987).
84. Julyan et al, "Preliminary clinical study of the distribution of HPMA copolymers bearing doxorubicin and galactosamine" J Control Release 57: 281–90 (1999).
85. Appleton et al. "Reactions of the cis-Diamminediaquaplatinum(II) Cation with 2-Aminomalonic Acid and Its Homologues, Aspartic and Glutamic Acids. Rearrangements of Metastable Complexes with Carboxylate-Bound Ligands to N,O-Chelates and Formation of Di- and Trinuclear Complexes", Inorg Chem, 29: 3985–3990 (1990).
86. Talebian, et al. "Synthesis and Characterization of a Series of Water Soluble Amidomalonato-(1R,2R-Cyclohexanediamine)Platinum(II) Complekes", J Coor. Chem, 22,165–173 (1990).
87. Appleton et al. "The Chemistry of Cisplatin in Aqueous Solution" in Platinum-Based Drugs in Cancer Therapy, Kelland and Farrell eds, Humana Press Totowa, N.J., 2000.
88. Sohn, et al. "Synthesis and antitumor activity of novel polyphosphazene(diamine)platinum(II) conjugates" Inter. J. Pharmaceutics 153: 79–91 (1997).

What is claimed is:

1. An amidomalonate N,O—Pt complex having the chemical structure:

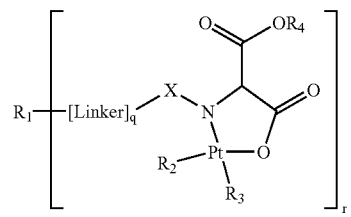

wherein:

X is C=O or $SO_2$;

$R_1$ is selected from the group consisting of an aliphatic group, a water-solubilizing group, a tumor-targeting group and a water-solubilizing group further comprising one or more tumor-targeting group(s);

q is 0 or 1;

r is 2–500;

[Linker] is selected from the group consisting of an alkyl group, an amino acid, a polyaminoacid, a polyethyleneglycol (PEG) and any combination of thereof;

$R_2$ and $R_3$ are independently selected from the group consisting of $NH_3$, a primary amine, a secondary amine, a tertiary amine and a nitrogen-containing heteroalicyclic; or, $R_2$ and $R_3$ are independently primary, secondary or tertiary amino groups, both of which are covalently bonded to carbon atoms of an aliphatic, an alicyclic, an aromatic, an aralkyl or a heterocyclic group wherein, when the amino group nitrogen atoms form a chelate with the Pt atom, a 5–7 member ring results;

$R_4$ is selected from the group consisting of hydrogen, a cation and an ester-forming group, wherein, the complex is obtained essentially pure by a process comprising contacting a corresponding amidomalonate O,O'—Pt complex or a mixture of amidomalonate O,O'—Pt and N,O—Pt complexes with an aqueous solution having a pH of 6.0 to 10.0.

2. An amidomalonate O,O'—Pt complex having the chemical structure:

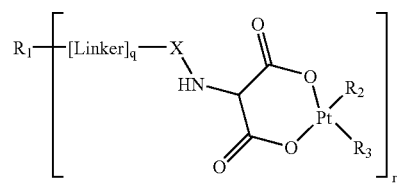

wherein:

X is C=O or $SO_2$;

$R_1$ is selected from the groups consisting of an aliphatic group, a water-solubilizing group, a tumor-targeting group and a water-solubilizing group further comprising one or more tumor-targeting group(s);
q is 0 or 1;
r is 2–500;
[Linker] is selected from the group consisting of an alkyl group, an amino acid, a polyaminoacid, a polyethylene glycol (PEG) and any combination of thereof;
$R_2$ and $R_3$ are independently selected from the group consisting of $NH_3$, a primary amine, a secondary amine, a tertiary amine and a nitrogen-containing heterocyclic; or,
$R_2$ and $R_3$ are independently primary, secondary or tertiary amino groups, both of which are covalently bonded to carbon atoms of an aliphatic, an alicyclic, an aromatic, an alkaryl or a heterocyclic group wherein, when the amino nitrogen atoms form a chelate with the Pt atom, a 5–7 member ring results;
the complex is obtained essentially pure by a process comprising contacting a corresponding amidomalonate N,O'—Pt complex or a mixture of amidomalonate N,O—Pt and O,O'—Pt complexes with an aqueous solution having a pH of 3.5 or less.

3. The complex of claim 1, wherein the pH is 7.0–8.0.
4. The complex of claim 2, wherein the pH is 2.0–3.5.
5. The complex of either claim 1 or claim 2, wherein the aqueous solution is at a temperature of 20° C. to 50° C.
6. The complex of either claim 1 or claim 2, wherein the aqueous solution is at a temperature of 35° C. to 40° C.
7. The complex of either claim 1 or claim 2, wherein the aqueous solution is maintained at the selected pH using a buffer.
8. The complex of claim 7, wherein the buffer is a phosphate buffer.
9. The complex of either claim 1 or claim 2, wherein the pH is maintained in the selected range by pH stating.
10. The complex of claim 1, wherein the cation is selected from the group consisting of $Li^+$, $Na^+$, $K^+$, $Ca^{2+}$, $Mg^{2+}$ and quaternary ammonium.
11. The complex of claim 10, wherein the cation is $Na^+$.
12. The complex of either claim 1 or claim 2, wherein $R_2$ and $R_3$ are $NH_3$.
13. The complex of either claim 1 or claim 2, wherein $R_2$ and $R_3$, together, comprise 1,2-diaminocyclohexane,

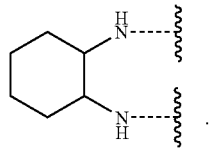

14. The complex of claim 13, wherein the 1,2-diaminocyclohexane is 1R, 2R-diaminocyclohexane.
15. The complex of either claim 1 or claim 2, wherein [Linker] comprises:

Gly-(W)$_p$Gly-wherein:
p is 0, 1, 2, 3, 4 or 5; and,
W is an amino acid or linear chain of amino acids, which may be the same or different.
16. The complex of claim 15, wherein p is 0.
17. The complex of claim 15, wherein p is 1 and W is Gly.
18. The complex of claim 15, wherein p is 2 and W is -Phe-Leu-.

19. The complex of claim 15, wherein p is 2 and W is Gly-Gly.
20. The complex of either claim 1 or claim 2, wherein $R_1$ is a water-solubilizing group.
21. The complex of claim 20, wherein the water-solubilizing group is a copolymer of N-(2-(hydroxypropyl)methacrylamide and acroyl($CH_2$=CHC(O)—) or methacroyl ($CH_2$=C($CH_3$)C(O)—).
22. The complex of claim 20, wherein $R_1$ is a polyaminoacid.
23. The complex of claim 22, wherein the polyaminoacid is selected from the group consisting of polyglutamate, polyaspartate and polylysine.
24. The complex of claim 20, wherein $R_1$ is a polysaccharide.
25. The complex of either claim 1 or claim 2, wherein $R_1$ is a water-solubilizing group further comprising a tumor-targeting group.
26. The complex of claim 25, wherein the tumor-targeting group is selected from the group consisting of folic acid, a folic acid derivative, a folic acid analog, vitamin $B^{12}$, a vitamin $B^{12}$ derivative, a vitamin $B_{12}$ analog, biotin, desthiobiotin and a biotin analog.
27. The complex of either claim 1 or claim 2, wherein $R_1$ is a tumor-targeting group.
28. The complex of claim 27, wherein the tumor-targeting group is selected from the group consisting of folic acid, a folic acid derivative, a folic acid analog, vitamin $B_{12}$, a vitamin $B_{12}$ derivative, a vitamin $B_{12}$ analog, biotin, desthiobiotin and a biotin analog.
29. The complex of either claim 1 or claim 2, wherein Pt is in the +2 oxidation state.
30. The complex of either claim 1 or claim 2, wherein Pt is in the +4 oxidation state.
31. The complex of either claim 1 or claim 2, wherein:
$R_1$ is a water-solubilizing random copolymer having the chemical structure:

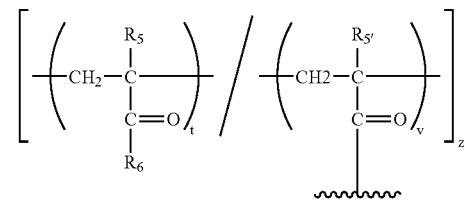

wherein:
t is 0.75–0.99;
v is 0.01–0.25;
t+v=11.00;
z represents the molecular weight of the polymer and is from 1 to 5000 kDaltons;
$R_5$ and $R_{5'}$ are independently selected from the group consisting of hydrogen and $CH_3$; and,
$R_6$ is a 2C–6C hydroxyalkyl group.
32. The complex of claim 31, wherein $R_6$ is 2-hydroxypropylamino ($CH_3CH(OH)CH_2NH$—).
33. The complex of either claim 1 or claim 2, wherein obtaining an essentially pure complex further comprises ultrafiltration.
34. The complex of claim 33, wherein ultrafiltration comprises tangential flow filtration.
35. The complex of claim 33, wherein ultrafiltration comprises centrifugal ultrafiltration.

36. A pharmaceutical composition comprising:
the complex of any one of claims 1, 2 or 31; and,
one or more pharmaceutically acceptable excipients.

37. A method of treating a solid tumor comprising administering to a patient in need thereof a pharmaceutically effective amount of a platinum complex of any one of claims 1, 2 or 31.

38. The method of claim 37, wherein the complex is administered parenterally.

39. A method of preparing an essentially pure amidomalonate N,O—Pt chelate from an essentially pure amidomalonate O,O'—Pt chelate or a mixture of amidomalonate N,O—Pt and O,O'—Pt chelates, comprising contacting the amidomalonate O,O'—Pt chelate or the mixture of amidomalonate N,O—Pt and O,O'—Pt chelates with an aqueous solution having a pH of 6.0–10.0.

40. The method of claim 39, wherein the pH is 7.0–8.0.

41. A method of preparing an essentially pure amidomalonate O,O'—Pt chelate from an essentially pure amidomalonate N,O—Pt chelate or a mixture of amidomalonate N,O—Pt and O,O'—Pt chelates, comprising contacting the amidomalonate N,O—Pt chelate or the mixture of amidomalonate N,O—Pt and O,O'—Pt chelates with an aqueous solution having a pH of 3.5 and lower.

42. The method of claim 41, wherein the pH is 2–3.5.

43. The method of either claim 39 or claim 41, wherein the aqueous solution is at a temperature of from 20° C. to 50° C.

44. The method of either claim 39 or claim 41, wherein the aqueous solution is at a temperature of from 35° C. to 40° C.

45. The method of either claim 39 or claim 41, wherein the aqueous solution is maintained in the selected pH range using a buffer.

46. The method of claim 45, wherein the buffer is a phosphate buffer.

47. The method of either claim 39 or claim 41, wherein the aqueous solution is maintained in the selected pH range using pH stating.

* * * * *

UNITED STATES PATENT AND TRADEMARK OFFICE
CERTIFICATE OF CORRECTION

PATENT NO. : 7,166,733 B2  
APPLICATION NO. : 10/779186  
DATED : January 23, 2007  
INVENTOR(S) : Paul Sood et al.

Page 1 of 1

It is certified that error appears in the above-identified patent and that said Letters Patent is hereby corrected as shown below:

On title page item (75)

Replace the current order of inventors by --Paul Sood; Donald R. Stewart; David. P. Nowotnik; Sergiy Victorovych Shevchuk; Kenneth Bruce Thurmond II.--

On title page item (12) should read: --Sood et. al.--

Signed and Sealed this

Sixth Day of March, 2007

JON W. DUDAS  
*Director of the United States Patent and Trademark Office*